(12) United States Patent
Gelvin et al.

(10) Patent No.: US 7,279,336 B2
(45) Date of Patent: *Oct. 9, 2007

(54) METHODS AND COMPOSITIONS FOR ENHANCED PLANT CELL TRANSFORMATION

(76) Inventors: Stanton B. Gelvin, 5726 Acre La., West Lafayette, IN (US) 47906; Kirankumar S. Mysore, # 6 Rock Island, Ardmore, OK (US) 74301; Kan Wang, 3203 Valley View Rd., Ames, IA (US) 50014; Bronwyn R. Frame, 2117 Northwestern Ave., Ames, IA (US) 50010

( * ) Notice: Subject to any disclaimer, the term of this patent is extended or adjusted under 35 U.S.C. 154(b) by 306 days.

This patent is subject to a terminal disclaimer.

(21) Appl. No.: 10/664,658

(22) Filed: Sep. 18, 2003

(65) Prior Publication Data

US 2004/0152197 A1    Aug. 5, 2004

Related U.S. Application Data

(63) Continuation-in-part of application No. 10/098,161, filed on Mar. 14, 2002, now Pat. No. 7,122,716.

(51) Int. Cl.
*C12N 15/84* (2006.01)
*C12N 15/82* (2006.01)
*C12N 5/04* (2006.01)

(52) U.S. Cl. ............... 435/469; 435/468; 435/418; 435/419; 800/278

(58) Field of Classification Search .......... None
See application file for complete search history.

(56) References Cited

U.S. PATENT DOCUMENTS 5,187,073 A * 2/1993 Goldman et al. .......... 800/294
6,215,051 B1 * 4/2001 Yu et al. .................. 800/320.2

FOREIGN PATENT DOCUMENTS

| DE | 43 09 203 C1 | 3/1993 |
| EP | 1 033 405 A2 | 9/2000 |
| WO | WO 97/12046 | 4/1997 |
| WO | WO 99/61619 | 12/1999 |
| WO | WO 00/17364 | 3/2000 |
| WO | PCT/US00/25260 | 4/2001 |

OTHER PUBLICATIONS

Enriquez-Obregon et al. 1999, Plant Cell, Tissue and Organ Culture 59:159-168.*
Mysore et al. 2000, PNAS 97:948-953.*
Narasimhulu et al. 1996, The Plant Cell 8:873-886.*
Ballas, N. and Citovsky, V. (1997) "Nuclear Localization Signal Binding Protein from *Arabidopsis* Mediates Nuclear Import of *Agrobacterium* VirD2 Protein." *Proc Natl Acad Sci USA* 94: 10723-10728.

Britt, A.B. (1996) "DNA Damage and Repair in Plants." *Annu Rev Plant Physiol Plant Mol Biol* 47: 75-100.
Deng, W., et al. (1998) "*Agrobacterium* VirD2 Protein Interacts with Plant Host Cyclophilins." *Proc Natl Acad Sci USA* 95: 7040-7045.
Ditta, G., et al. (1980) "Broad host Range DNA Cloning System for Gram-Negative Bacteria: Construction of a Gene Bank of *Rhizobium Meliloti,*" *Proc Natl Acad Sci USA* 88(12): 7347-7351.
Gheysen, G., et al. (1991) "Illegitimate Recombination in Plants: A Model for T-DNA Integration." *Genes & Development* 5: 287-297.
Jefferson, R.A., et al. (1987) "GUS Fusions: β-Glucuronidase as a Sensitive and Versatile Gene Fusion Market in Higher Plants." *EMBO J* 6(13): 3901-3907.
Koncz, C. and Schell, J. (1986) The Promoter of $T_L$-DNA Gene 5 Controls the Tissue-Specific Expression of Chimeric Genes Carried by a Novel Type of Agrobacterium Binary Vector. *Mol Gen Genet* 204: 383-396.
Lichtenstein, G., and Draper, J., (1986)"Genetic of Engineering Plants." *In Glover, D.M.* (ed.) *DNA Cloning: A Practical Approach* 2: 67-119 (IRL Press, Oxford).
Matsumoto, S., et al. (1990) "Integration of *Agrobacteriaum* T-DNA into a Tobacco Chromosome: Possible Involvement of DNA Homology between T-DNA and Plant DNA." *Mol Gen Genet* 224: 209-316.
Mysore, K.S., et al. (1998) "Role of the *Agrobacteriaum Tumefaciens* VirD2 Protein in T-DNA Transfer and Integration." *American Phytopathological Society* 11(7): 668-683.
Nam, J., et al. (1997) "Differences in Suspectibility of Arabidopsis Ecotypes to Crown Gall Disease May Result from a Deficiency in T-DNA Integration." *Plant Cell* 9: 317-333.
Nam, J., et al. (1997) "Identification of T-DNA Tagged *Arabidopsis* Mutants that are Resistant to Transformation by *Agrobacterium.*" *Mol Gen Genet* 216: 429-438.
Narasimhulu, S.B., et al. (1996) "Early Transcription of Agrobacterium T-DNA Genes in Tobacco and Maize." *Plant Cell* 8: 873-886.
Ni, M., et al. (1995) "Strength and Tissue Specificity of Chimeric Promoters Derived from the Octopine and Mannopine Synthase Genes." *Plant J* 7(4): 661-676.
Offringa, R., et al. (1990) "Extrachromosomal Homologous Recombination and Gene Trageting in Plant Cells after *Agrobacteriaum* Mediated Transformation." *EMBO J* 9(10): 3077-3084.
Ohba, T., et al. (1995) "DNA Rearrangement Associated with the Integration of T-DNA in Tobacco: An Example for Multiple Duplications of DNA Around the Integration Target." *Plant J* 7(1): 157-164.

(Continued)

*Primary Examiner*—Ashwin Mehta
*Assistant Examiner*—Li Zheng
(74) *Attorney, Agent, or Firm*—Barnes & Thornburg LLP; Alice O. Martin

(57) ABSTRACT

Methods and compositions to increase *Agrobacterium* transformation efficiency (frequencies) in both dicot and monocot host plants include adding histones to the host plant at most transiently, and using histones and L-cysteine at certain stages in monocot transformation.

15 Claims, 32 Drawing Sheets

OTHER PUBLICATIONS

Paszkowski, J., et al. (1988) "Gene Targeting in Plants." *EMBO J* 7(13): 4021-4026.

Sambrook, M.A., et al. (1982) in *Molecular Cloning: A Laboratory Manuel.* 1st ed. Cold Spring Harbor Laboratory Press, Cold Spring Harbor, New York, pp. 150-172; 312-328, 365-381 and 383-389.

Sheng, J. and Citovsky, V. (1996) "Agrobacterium-Plant Cell DNA Transport: Have Virulence Proteins, Will Travel." *Plant Cell* 8: 1699-1710.

Zupan, J. and Zambryski, P. (1997) "The *Agrobacteriaum* DNA Transfer Complex." *Critical Reviews in Plant Sciences* 16(3): 279-295.

Citovsky, V., et al. (1992) "Nuclear Localization of Agrobacterium VirE2 Protein in Plant Cells." *Science* 256: 1802-1805.

Hye Huh, G.H., et al. (1997) "Structural Characteristics of Two Wheat Histone H2A Genes Encoding Distinct Types of Variants and Functional Differences in their Promoter Activity." *Plant Molecular Biology* 33: 791-802.

Mysore, K.S., et al. (1998) "An *Arbidopsis* histone H2A mutant is deficient in *Agrobacterism* T-DNA integration." *PNAS* 97(2): 948-953.

Nakamura, Y., et al. (1998) "Structural Analysis of Arabidopsis Thaliana Chromosome." *Database EMBL (Online): Accession No: AB016878.*

Nam, J., et al. (1999) "Identification of T-DNA Tagged *Arabidopsis* Mutants that are Resistant to Transformation by *Agrobacterium.*" *Mol Gen Genet* 261:429-438.

Prymakowska-Bosak, M., et al. (1996) "Histone H1 Overexpressed to High Level in Tobacco Affects Certain Developmental Programs but has Limited Effect on Basal Cellular Functions." *Proc. Natl. Acad. Sci. USA* 93: 10250-10255.

Regensburg-Tuink, A.J.G., et al. (1993) "Transgenic N. *Glauca* Plants Expressing Bacterial Virulence Gene *virF* are Converted into Hosts for Nopaline Strains of A. *Tumefaciens.*" *Nature* 363:69-71.

Bent, Andrew F. and Clough, Steven J. (1998) "Agrobacterium Germ-Line Transformation: Transformation of Arabidopsis without Tissue Culture" *Plant Molecular Biology Manual* B7:1-14.

Bent, A.F. and Clough, S.J. (1998) "*Agrobacterium* Germ-Line Transformation: Transformation of *Arabidopsis* without Tissue Culture." *Plant Molecular Biology Manual* B7, 1-14.

Gheysen, G. et al. (1991) "Illegitimate Recombination in Plants: A Model for T-DNA Integration." *Genes & Development* 5:287-297.

Jefferson, R.A., et al. (1987) "GUS Fusions: β-Glucuronidase as a Sensitive and Versatile Gene Fusion Marker in Higher Plants." *EMBO J* 6(13):3901-3907.

Koncz, c. and Schell, J. (1986) "The Promoter of $T_L$-DNA Gene 5 Controls the Tissue-Specific Expression of Chimeric Genes Carried by a Novel Type of Agrobacterium Binary Vector." *Mol Gen Genet* 204:383-396.

Lichtenstein, G., and Draper, J. (1986) "Genetic of Engineering Plants." *In* Glover, D.M. (ed.) *DNA Cloning: A Practical Approach* 2:67-119 (IRL Press, Oxford).

Matsumoto, S., et al. (1990)- "Integration of *Agrobacterium* T-DNA into a Tobacco Chromosome: Possible Involvement of DNA Homology between T-DNA and Plant DNA." *Mol Gen Genet* 224:309-316.

Mysore, K.S. et al. (1998) "Role of the *Agrobacterium Tumefaciens* VirD2 Protein in T-DNA Transfer and Integration." *American Phytopathological Society* 11(7):668-683.

Narasimhulu, S.B., et al. (1996). "Early Transcription of Agrobacterium T-DNA Genes in Tobacco and Maize." *Plant Cell* 8:873-886.

NI, M., et al.(1995) "Strength and Tissue Specificity of Chimeric Promoters Derived from the Octopine and Mannopine Synthase Genes." *Plant J* 7(4):661-676.

Ohba, T., et al.(1995) "DNA Rearrangement Associated with the Integration of T-DNA in Tobacco: An Example for Multiple Duplications of DNA Around the Integration Target." *Plant J* 7(1):157-164.

Prymakowska-Boask, M., et al. (1996) "Histone H1 Overexpressed to High Level in Tobacco Affects Certain Developmental Programs but has Limited Effect on Basal Cellular Functions." *proc. Natl. Acad. Sci. USA* 93:10250-10255.

Regensburg-Tuïnk, A.J.G., et al.(1993) "Transgenic N. *Glauca* Plants Expressing Bacterial Virulence Gene *virF* are Converted into Hosts for Nopaline Strains of A. Tumefaciens." *Nature* 363:69-71.

Sambrook, M.A., et al. (1982) in *Molecular Cloning: A Laboratory Manuel*, 1st ed. Cold Spring Harbor Laboratory Press, Cold Spring Harbor, New York, pp. 150-172; 312-328; 365-381; and 383-389.

Sheng, J. and Citovsky, V. (1996) "Agrobacteriaum-Plant Cell DNA Transport: Have Virulence Proteins, Will Travel." *Plant cells* 8:1699-1710.

Zupan, J. Zambryski, P. (1997) "The *Agrobacteriaum* DNA Transfer Complex." *Critical Reviews in Plant Sciences* 16(3):279-95.

Gelvin et al., "Isolation and Characterization of RAT (Resistant to Agrobacteriaum Transformation) Mutants," *Program & Abstracts 9th International Conferences on Arabidopsis Research*, p. 171 (1998).

Huh et al., "Differential Expression of the Two Types of Histone H2A Genes in Wheat," *Biochim. Biophys. Acta*, 1261:155-160 (1995).

Mysore et al., "A Histone H2A Mutant of Arabidopsis is Recalcitrant to Agrobacterium Transformation," *Program & Abstracts 9th International Conference on Arabidopsis Research*, p. 211 (1998).

Nakamura et al., "Structural Analysis of Arabidopsis Thaliana Chromosome 5", NCBI (Online) Accession No. AB016879, *DNA Res.*, 5(5):297-308 (1998).

Nam et al., "Agrobacteriaum Tumefaciens Transformation of the Radiation Hypersensitive Arabidopsis Thaliana Mutants UVH1 and RADS," *Mol. Plant-Microbe Interact,*, 11: 1136-41 (1998).

Sato et al., "Structural Analysis of Arabidopsis Thaliana Chromosome 3," *NCBI (Online) Accession No. AB016878* (2000).

* cited by examiner

Fig. 1B

TCAAAGGAAAGACATTAAATTAGAAATTTGAAACATGTTGATAGATCATGTCCTTCTTCTCGGTTACCCAGTT 80
TTGCCCTAAAACCTAAAACCAACAGGACCATCATTTCGACCACCATTGACTGGTCTGCCCCAATCTAGCTATGATA 160
TATCTTAATTCCGTATGACTTGGATCCATAAATATTGAAATAGATTTGGTGAACACAAATTACTCTTAAACTTCTTCT 240
CTTTCATGCATGTTCTTTCTCACTTTATAGTGACATTTTTATATAGTGACATTTTTAGTAATGAACAACACAATTGATTA 320
GTAATTCATCAAATTTATATAGTGATAAATTCCACAATGGTTGTTCAATAAAATATGAACAACACAATAGAATTAGTA 400
AAAGTGACTATGTTAAATCATTTCTTGCTGGGGTTTGGTGGGCGAGTTCTAAACCCATATAAGCGCCCATTTACTTCGT 480
AAACTCAATTCGATTTGTTCAGCGTTCCAAGAGAAACCAACACAAACAATATATTTCAAGGCATAAATAAATTGAGGTTTATATGGA 560
AAATTTGGAAATTCCCCTGCTGTCCAGAGAAAACAACAAACAAAACTGCAAAAGTTCAAGCGGTGGGAGAAAAACTTCAGATC 640
GTAGCCATTCATTAAATTATAACAACGGTTTAAACCTCTTCGATCCGCTATTCCGTATCTCAAGCCCTTATGGTCAAATAACTTAA 720
TCCTCCACATATATAACACAATCAGATTTCTCTGTTAATTTCGTCAAGAAAAAATTCGATTTTTTGCGCTCTTTG 800
TGGGTTGTGTGTTGAAAATGGCTGGTCGTGTCGGTCGTTCCAATCTCGTTTCTTAAAACTCTTCGTTCTTAAAAGCTACATCTCGGAGTA 880
GCAAAGCCCGGTCTCCAATTCCCGGTTCGCGCCCGTTCTGACTCTGTTTTGCCGCGATCGAGAGCCGGTAAATTACATGCCGAACGTGTTTCTCTTTCCA 960
GGTGCTCCGGTTTATCTCGCCCGCCGTTCTGACTCTGTTTTTGCCGTGATCGAATCTAGGGTTCTTGACCTAATTTGGGTTTGTTCT 1040
TCCGTTTCCGATCTTATTCGTCGTCTGACTCTGTTTTTGCCGTGATCGAATCTAGGGTTCTTGACCTAATTTGGGTTTGTTCT 1120
GACATGCAAAAATTGAATTAGATTCGTCGTCGTTGAATTGTTGTAGTTCTCGTTTTCTCGCAAGATTCTAAATTTTTTCAATTATGGTAAC 1200
GATTGGTTGATGGTAATCGAGATCATATGAAGTTCGTTGAGTTTCTCGCAAGATTCTAAATTTTTTCAATTATGGTAAC 1280
CAATTGATTTGAGTTGTTAAATTTCTCAAATTGTGAAATTGATCATGAAGTTGTGTTTGAATTTGTTCAGGTTCT 1360
TGAATTAGCTGGAAACGGCAGCAAGACGCAAGAAGACAACAAGAAGACACGTATTGTTCCTCGTCACATTCAGCTTGCGGTCAGAAACG 1440
ATGAGGAGCTAAGCAAGCTTCTTGGAGATGTGACGATTGCTAATGGAGGAGTGATGCCTAACATCCACACAATCCCTTCTC 1520
CCTAAGAAGGCTGGTGTCGTCGCTTCAAGCCTCAAAGCCTCAAGCCTACATTGCTAATAGCCTACAATGATATAGAACACGTCTCTCTTTGCA 1600
TTTTTCAGGATATATTGTGGTGTAAACAAATTGACGCTTAGACAACTTAATAACACATTGCGACGTTTTAATGTACTG 1680
AATT

T-DNA ──────── insertion site

Italics ──────→ Open reading frame
Bold ──────→ Intron
Underline ──────→ T-DNA LB sequence Ws  rat5

Transgenic *rat5* plants expressing
the *RAT5* histone H2A gene

Transgenic Ws plants overexpressing the RAT5 histone H2A gene

✦ maize lines A10 (transgenic for E2250)

HTA1-C

```
TAATTTCGTC AAGAAAAAAA TTCGATTTTT TTGCGCTCTT TGTGGGTTGT TGTTGTTGAA
AATGGCTGGT CGTGGAAAAA CTCTTGGATC CGGTGGGGCG AAGAAAGCTA CATCTCGGAG
TAGCAAAGCC GGTCTTCAAT TCCCGGTGGG TCGTATCGCT CGTTTCTTAA AAGCCGGTAA
ATACGCCGAA CGTGTTGGTG CCGGTGCTCC GGTTTATCTC GCCGCCGTTC TCGAATATTT
GGCCGCCGAG GTTCTTGAAT TAGCTGGAAA CGCAGCAAGA GACAACAAGA AGACACGTAT
TGTTCCTCGT CACATTCAGC TTGCGGTCAG AAACGATGAG GAGCTAAGCA AGCTTCTTGG
AGATGTGACG ATTGCTAATG GAGGAGTGAT GCCTAACATC CACAATCTCC TTCTCCCTAA
GAAGGCTGGT GCTTCAAAGC CTCAGGAAGA TTAGGTCTTT TAACACAATG ATATAGAACA
CGTCTCTCTT TTGGCTTTAG ATCTAATAAC CTAATAACTA GCTAGATGTT TTCACTTTTT
GTATCTTTGC TTTTTTTAAT TCCTTTAGGG ATTTGTTTCT TTCCGTTTCT GTTTCGACAT
GTTGTTTCTG TTTTTGTGAA TATATGAAAG TATTTTGC
```

HTA2-C

```
GAGAAATTTC TCAGTTACGC TTCATCCTCC TCTAAGAGAT CTTTTTTCTA TCTTGGGTAG
TAGAGAGAAA TGGCGGGTCG GGGAAAACAA CTTGGATCTG GTGCAGCGAA GAAGTCTACT
TCTCGTAGTA GCAAGGCTGG GCTTCAATTC CCTGTTGGTC GTATCGCTCG ATTTTTGAAA
GCCGGTAAGT ACGCCGAGCG TGTTGGTGCC GGAGCTCCGG TCTATCTCGC CGCCGTTCTT
GAATACCTCG CCGCTGAGGT ACTTGAGCTT GCTGGGAACG CAGCGAGAGA CAACAAGAAG
ACCCGTATAG TTCCACGACA CATTCAGCTT GCTGTGAGGA ATGATGAGGA GCTAAGCAAG
TTGCTTGGAG ATGTGACAAT TGCTAATGGA GGAGTGATGC CTAACATCCA CAATCTCCTT
CTCCCCAAGA AGGCTGGTTC ATCTAAGCCT ACTGAAGAAG ATTAGGTTCA TTACGAAGAT
AGGGAAAGCT GGAAACTGGT TGATATCAGA TAATGCTTAG GATTGTTTTT TTTTTCATTT
GCTTTTCCTC TGCAGCAATG GAAGCTGTGT GGTTGTACTA GTTGTTAAGG TTACCTTTGT
TTCACTTTAT GTGAATATAT GAAGAAATTG TTCTATTTC
```

HTA3-C

```
AAATCACTCC ACTCACAAAA TCCTCAGCCA TCTCTAATCA CATTTTACAA TCGCCTCTTC
AAATTTCCCG ATAAACAAAA AATGAGTTCC GGCGCCGGCA GTGGAACAAC TAAAGGTGGC
AGAGGAAAGC CAAAAGCTAC AAAGTCCGTC TCTCGATCTT CTAAAGCTGG TCTTCAATTT
CCCGTTGGAA GAATCGCTAG ATTCCTTAAA GCCGGTAAAT ACGCCAACG TGTTGGTGCC
GGTGCTCCCG TTTATCTCTC CGCCGTTCTC GAATACCTCG CCGCTGAGGT ATTGGAGCTA
GCTGGAAATG CAGCAAGAGA TAACAAGAAG ACACGTATCG TACCACGGCA CATTCAGCTT
GCAGTGAGGA ACGATGAAGA GCTTAGTAAA CTTCTTGGAA GTGAACAAT TGCTAATGGA
GGAGTTTTGC CCAACATTCA TCAGACTCTT CTCCCATCAA AGGTTGGAAA GAACAAAGGC
GATATCGGAT CTGCTTCTCA AGAGTTTTAA TTTTATTTTT TAGCTTGTAA CATAGACATG
GCTCTCTGTT CCACAATAGT TTTGGTATTT TCATGTTACT CAAAAACTGT GTTTGCAAAT
CCAGTAATGA ATTCGGTTTG AAGAAGTGAA ATAGTTAAAT TTGATGTGTT GAAATAGCGG
ATTCAATGGC TTCAATACAA GTGCTAATAG GTTTGGCTTT AGCCATGGTT TCTGCAAGTG
AGACTCTTGC TTCTTTGTGA GAATGTAATA ATGAGACAGT GTTGGAAACA GCCCATTTGA
TATGAGCCTC CTTTTCTGAT T
```

FIG. 6(A)

HTA4-C

```
ATGGTGTGCA ACACGAATAT ACTAAAAGAT GTGTCGACGA AGATAAGTGC TTTTGAAAAT
GTTCGGATGA TTATGGTGGA GGGAGAGATG TTTCAAGTGG CTCGTATTCA CAAGCAACTT
AAGAACAGAG TTTCTGCACA TAGTAGTGTT GGTGCGACTG ATGTTGTCTA CATGACTTCA
ATCCTTGAAT ACCTAACTAC AGAGGTTCTT CAGTTGGCCG AAAACACTAG CAAAGATTTA
AAAGTGAAGA GGATAACTCC AAGGCATTTG CAGTTGGCGA TCAGAGGAGA TGAAGAGCTT
GACACACTCA TCAAAGGAAC AATTATTGGA GGAAGTGTGA TCCCTCACAT CCACTAG
```

HTA5-C

```
CATATAGAGA AGAGCAAAAC CCTAAAGCCC ACTCATCTTC TCAATTCCCA GATCATCTAC
AATAGTCATT TCTCTTCGAT TTCTTCAAAC TCTCATCAAA TCGTTTATCT GTTCTAAATT
TCGAAGAAGA CGATGAGTAC AGGCGCAGGA AGCGGAACAA CCAAAGGTGG CAGAGGAAAG
CCAAAGGCCA CCAAATCCGT CTCTCGATCA TCTAAAGCCG GTCTTCAATT CCCCGTCGGA
AGAATCGCTA GATTCCTCAA ATCCGGTAAA TACGCCGAGC GTGTCGGTGC CGGAGCTCCG
GTCTATCTCT CCGCTGTTCT CGAGTACCTC GCCGCCGAGG TGTTGGAGCT GGCGGGAAAC
GCAGCAAGGG ATAACAAGAA GACACGTATA GTACCAAGAC ACATTCAGCT TGCAGTGAGG
AACGATGAAG AGTTAAGCAA ACTTCTGGGA AGTGTGACGA TTGCGAATGG AGGAGTTTTG
CCAAATATTC ATCAGACTCT TTTGCCATCC AAGGTTGGCA AGAACAAAGG AGATATTGGA
TCTGCTTCTC AGGAGTTCTG AGGTTCTTAG ACTTCTTAGT TCAGTTCTCT TGTTTGGATT
CGGAACTTGT AAAATAGACC CTGATGGTGT TTTTTGGGGA TCAAATTAGG TTTTAAAGCT
AAGTATATTT GGCTTTTGCC TAAGTATGTT TAATTAGTGA ATGATATGAT ATTTCGGAAC
GAATCATGTA TCAATGGAA
```

HTA6-C

```
TTAAATCACA AATCTTCAAC TTCCGATACT TTCAATCTCT CTAAACTCTC AATTTCAGTA
ATCGATAACC GTAGCAATGG AATCCACCGG AAAAGTGAAG AAAGCTTTCG GAGGAAGAAA
ACCACCTGGT GCCCCAAAAA CCAAATCGGT TTCGAAATCG ATGAAAGCCG GTCTTCAATT
CCCAGTGGGA AGAATCACTC GTTTCCTGAA GAAAGGACGA TACGCTCAGA GACTTGGTGG
TGGTGCTCCG GTTTACATGG CCGCCGTTCT TGAATACCTC GCCGCAGAAG TTCTGGAGCT
TGCTGGTAAC GCTGCGAGAG ATAACAAGAA ATCAAGGATA ATTCCGAGGC ATCTTCTTCT
CGCGATAAGG AACGATGAAG AATTGGGGAA ACTTCTGAGT GGTGTCACAA TCGCTCACGG
TGGTGTTTTG CCTAACATCA ACTCTGTTCT ATTGCCTAAG AAGTCTGCCA CTAAACCAGC
TGAAGAAAAG GCTACCAAAT CACCAGTCAA GTCTCCAAAG AAAGCTTAAT CTGCTAGAGT
TTTCGTTGCT AGTTTGTGTT TGAGCTCTGG TGAATGTAGA AATTTGAAGC TTTTGGATCT
TAGTTTCTAT GTATTTGGTG ATTTAGAATG TTGTTCAAAA TCCTTTTCCT AATCATAAGA
ATTTATGATC TATCTATTAT ACGCTTCGTC TAATCTTTT
```

HTA7-C

```
CAAATCGTAA ACCGCCACAA AACCGAAAAA AACACTAATT GTGCTTTCCC TTTAGATTCA
TTTGTATTTT CTTTTGGAGC TTTTGAACAA TGGAGTCATC ACAAGCAACG ACGAAGCCAA
CGAGAGGAGC AGGAGGAAGG AAAGGTGGAG ATAGGAAGAA GAGTGTTAGT AAATCTGTTA
AAGCTGGTCT TCAATTTCCC GTTGGTCGTA TCGCTCGTTA CTTGAAGAAA GGTCGGTACG
CTCTCCGATA CGGTTCCGGT GCTCCGGTTT ACCTCGCCGC CGTTCTCGAA TACCTAGCCG
CCGAGGTACT TGAGCTAGCT GGGAACGCAG CGAGAGATAA TAAGAAGAAC AGGATAAACC
CTAGGCATCT ATGTTTAGCG ATAAGGAACG ATGAGGAATT GGGGAGATTG CTTCATGGAG
TTACTATTGC TAGTGGTGGT GTTCTTCCAA ACATTAATCC AGTTCTTCTT CCTAAGAAAT
CAACAGCTTC TTCTTCTCAA GCGGAGAAAG CTTCTGCTAC CAAATCTCCT AAGAAGGCTT
GATAAAGAAT AGTATCGATG TTGCTTTTTG GTTATATTCG GATCTTAGAT GAAGAAGAAG
AAGAAGAAGA AACAACTTGT TTTTTGTTTT AGAGGATTTG TGTAGGTATC TGAAATCTTC
TTCTCTTTGT TTTGGTTTGT CTTATGTAAA AACCATGGGA AGATGATTAT GTTTGTTAAC
GCAATTTGTA ATGGAAAATA ATTAAGTTCT GGGATTAGT
```

FIG. 6(B)

HTA8-C

```
AATTCGACGT CTCTCTTTTG TCTCTGTATC GATTTTCTCG CCGCGAATTT CGAATAGGTT
CTTCACCATA AGCTTGAGAT CTTATTTCTC TACTGTTCTT TGCTTCTTCT CTATCGATAT
GGCTGGTAAA GGTGGGAAAG GGCTTCTAGC TGCGAAGACG ACGGCAGCAG CTGCAAACAA
AGACAGTGTT AAGAAGAAAT CCATCTCTCG CTCTTCTCGT GCTGGTATTC AGTTTCCAGT
GGGTCGTATT CATCGTCAAC TCAAGCAAAG AGTTTCAGCA CATGGAAGAG TTGGTGCCAC
TGCTGCTGTT TACACTGCAT CAATTCTAGA ATACTTGACT GCTGAAGTAC TCGAGTTAGC
TGGAAATGCG AGCAAGGATC TCAAAGTGAA GAGAATTACA CCAAGACATT TGCAGCTTGC
AATCAGAGGA GATGAGGAAC TTGACACTCT CATCAAAGGA ACCATTGCAG GAGGAGGTGT
GATCCCTCAC ATCCACAAGT CCCTTGTCAA CAAAGTCACC AAGGATTGAG TTTCGCTCTC
TGAGTCCTAA GTCTCTATTA TACTATGTGC TCTTTTCTAG ACGCCCTCAT GTGTATATGG
GTTCATTGTA TCTCTTAGGT CTCTCGTTTT AGACTCATAC TCTTGTTATT TTGCTAATGC
TTACATGATT GAGG
```

HTA9-C

```
ATCGGGAGAC TCCTCTTCGA GCTCATCTTC TTCTCTCTCT TTTTATCTTT GGTTGTGCGA
TCTCCTTTCT CTTTCAATCT CCAAGGATTT TACTGTGAGA TATTTGGCGG GAAAATGTCG
GGGAAAGGTG CTAAAGGTTT GATTATGGGG AAACCCAGCG GTAGCGACAA GGATAAGGAC
AAGAAGAAGC CTATCACTCG TTCTTCTCGA GCTGGTCTCC AGTTCCCAGT TGGTAGGGTG
CATCGTCTGT TAAAGACAAG GTCCACTGCT CATGGAAGGG TTGGAGCAAC TGCAGCTGTT
TACACAGCAG CAATATTGGA GTATCTGACT GCAGAAGTTT TGGAGTTGGC TGGTAACGCC
AGCAAGGACT TGAAGGTGAA ACGTATCTCG CCGAGGCATT TGCAGCTTGC GATTCGTGGA
GATGAGGAGC TCGATACTCT CATCAAAGGA ACTATAGCTG GTGGTGGAGT CATCCCTCAT
ATCCACAAGA GTCTCATCAA CAAATCCGCC AAGGAATAGG ACTTTTTTAG TTACCCGCTT
TGTTCTGTGT TGCTTTTCTG TTTTCTAAAT GTTTTTAAGA GTTGTTGTTT GATAAGATGC
TAGAGAAGCT CTTTTTAGGA TCGTTTGCTA TTGTTCGTTC GATCAGCGTA CTTTGTGTTA
GAGACGCCAG TCGATTTATC TATCTTTAAA AATGTATTCG AATGATTATC CAAAAACCAT
TTCTGA
```

FIG. 6(C)

HTA10-C

AACAACAAAT TCGATTCTTA TAACTGTTTC CCTCTCATCT TTACACAAAA GTATTCTAAT
CGATTTCAAT GGCGGGTCGT GGTAAAACAC TCGGATCTGG GTCTGCGAAG AAGGCAACAA
CAAGAAGCAG CAAAGCCGGT CTCCAATTCC CTGTGGGTCG TATCGCTCGT TTCTTGAAGA
AAGGCAAATA CGCCGAACGT GTTGGTGCCG GAGCTCCGGT TTACTTAGCC GCCGTTCTCG
AATACCTCGC CGCTGAGGTA TTGGAATTGG CTGGAAACGC AGCGAGGGAT AACAAGAAGA
CGAGGATTGT TCCAAGGCAT ATTCAATTGG CGGTGAGGAA CGATGAAGAA TTGAGCAAAT
TGCTTGGAGA TGTGACTATT GCTAATGGAG GTGTGATGCC TAACATTCAC AATCTTCTTC
TTCCTAAGAA GACCGGTGCT TCCAAGCCAT CTGCTGAAGA CGATTGATTA ATCAACCAAA
TCCACTCTCT TGTGTTTTTT GAGTTTTTAA GGCTTTTTAA GAGTAATTTA GATTAGATCT
ATGGTGAAGA AAGAATCTAT CTTCTGTGTT TTTTGAATTG AATTGAATGT TCATATGCTT
TCAATTTCTT ATGGAATCAA GATTTAACT TTTCT

HTCCTTTTGCAT TCTCTCGTCG TCGTCTCAAG ATCTAGAAGA AGGAAACAAC AATTTCAAGA
GACATGGCAG GCAAAGGTGG AAAAGGACTC GTAGCTGCGA AGACGATGGC TGCTAACAAG
GACAAAGACA AGGACAAGAA GAAACCCATC TCTCGCTCTG CTCGTGCTGG TATTCAGTTT
CCAGTTGGAC GAATTCACAG GCAACTGAAG ACCCGAGTCT CGGCACATGG CAGAGTTGGT
GCCACTGCAG CCGTCTACAC AGCTTCAATC CTGGAGTATC TGACAGCAGA GGTTCTTGAG
TTGGCTGGGA ATGCGAGCAA GGATCTCAAA GTGAAGAGGA TAACGCCAAG GCATCTGCAG
TTGGCGATTA GAGGAGATGA GGAGCTGGAC ACACTCATCA AGGGAACGAT TGCTGGAGGT
GGTGTGATCC CTCACATCCA CAAGTCTCTC ATCAACAAAA CCACCAAGGA GTGATGTGTA
GCTTTTTATG GTGTTTGTAT TTCTGTAGTC TTGGACTCAT TTTCCTTTAT CCTTTTCTTA
GTTCTTTGAC TAGTGTTGAC CTCTTCTGGA CATCCTCAGG TGTACATTAG TTAATTTGAA
CTCTTTAGGT TCCTT

HTA11-C

CCTTTTGCAT TCTCTCGTCG TCGTCTCAAG ATCTAGAAGA AGGAAACAAC AATTTCAAGA
GACATGGCAG GCAAAGGTGG AAAAGGACTC GTAGCTGCGA AGACGATGGC TGCTAACAAG
GACAAAGACA AGGACAAGAA GAAACCCATC TCTCGCTCTG CTCGTGCTGG TATTCAGTTT
CCAGTTGGAC GAATTCACAG GCAACTGAAG ACCCGAGTCT CGGCACATGG CAGAGTTGGT
GCCACTGCAG CCGTCTACAC AGCTTCAATC CTGGAGTATC TGACAGCAGA GGTTCTTGAG
TTGGCTGGGA ATGCGAGCAA GGATCTCAAA GTGAAGAGGA TAACGCCAAG GCATCTGCAG
TTGGCGATTA GAGGAGATGA GGAGCTGGAC ACACTCATCA AGGGAACGAT TGCTGGAGGT
GGTGTGATCC CTCACATCCA CAAGTCTCTC ATCAACAAAA CCACCAAGGA GTGATGTGTA
GCTTTTTATG GTGTTTGTAT TTCTGTAGTC TTGGACTCAT TTTCCTTTAT CCTTTTCTTA
GTTCTTTGAC TAGTGTTGAC CTCTTCTGGA CATCCTCAGG TGTACATTAG TTAATTTGAA
CTCTTTAGGT TCCTT

FIG. 6(D)

HTA12-C

```
ATGGATTCCG GAACCAAAGT GAAGAAAGGA GCCGCTGGAA GAAGAAGTGG TGGAGGTCCT
AAGAAGAAAC CGGTTTCCCG TTCGGTTAAA TCCGGTCTAC AGTTTCCTGT CGGTAGGATC
GGTCGGTATC TTAAGAAAGG TCGTTATTCG AAGCGTGTCG GAACCGGAGC TCCGGTCTAT
CTCGCCGCCG TCCTCGAGTA TCTTGCTGCT GAGGTTCTCG AGCTTGCTGG TAACGCTGCA
AGAGATAACA AAAAGAACCG TATTATACCA CGCCATGTTC TATTAGCGGT GAGGAACGAC
GAGGAGCTAG GGACACTACT CAAAGGCGTA ACCATTGCAC ACGGCGGTGT TTTACCAAAC
ATAAACCCAA TACTCCTCCC AAAGAAGTCT GAGAAAGCAG CTTCAACTAC AAAAACACCC
AAATCACCAT CAAAGGCAAC CAAATCCCCT AAGAAATCTT AGTACTTCTT TCTTCATTCC
TCTGTATAAC CTACTGTTTC TATCTCTCTG TACGTTTCTC TGTAAAGACA GAACAGAATA
TCTCTTTGTT GTTGTGAGAA AGCTTAGTTT CTCTGATCGT CGTTGTGAAA TAAAAAATGC
AACGTTTCAT AT
```

HTA13-C

```
ATCTTAATTT CCCTCGCATT GAGAATTTTC AACTTTTTCT ATCTCTCTTC CCAAATCACA
AATGGCGGGT CGCGGCAAAA CTCTCGGATC TGGCGTTGCT AAGAAATCAA CATCGAGAAG
CAGCAAAGCC GGTCTCCAAT TCCCCGTTGG TCGTATCGCT CGTTTTCTAA AGAACGGCAA
GTACGCAACA CGTGTTGGTG CCGGAGCTCC GGTTTACTTA GCCGCCGTTC TCGAATACCT
CGCCGCTGAG GTATTGGAAT TGGCTGGAAA CGCAGCTAGG GATAACAAGA AGACTAGGAT
TGTGCCACGT CACATTCAGC TCGCGGTGAG AAACGATGAG GAGCTGAGTA AACTGCTTGG
AGATGTGACG ATTGCTAATG GAGGTGTGAT GCCTAACATT CACAGTCTTC TTCTTCCCAA
GAAAGCTGGT GCTTCAAAAC CTTCCGCTGA TGAAGATTAG ATTAGGGATT TGTGTTGTGG
TTGTTTAGCT AATTAATGTG TAGCTTAGTC TTTCATTAGA TTAGATCTGA ATTAGTTTTC
ATTAATGGTG TTGTGTAGTC TCTCTTTTGC TTCAAAAACA AGTATTAAAA TC
```

FIG. 6(E)

```
HTA1-P

MAGRGKTLGS GGAKKATSRS SKAGLQFPVG RIARFLKAGK YAERVGAGAP VYLAAVLEYL
AAEVLELAGN AARDNKKTRI VPRHIQLAVR NDEELSKLLG DVTIANGGVM PNIHNLLLPK
KAGASKPQED

HTA2-P
MAGRGKQLGS GAAKKSTSRS SKAGLQFPVG RIARFLKAGK YAERVGAGAP VYLAAVLEYL
AAEVLELAGN AARDNKKTRI VPRHIQLAVR NDEELSKLLG DVTIANGGVM PNIHNLLLPK
KAGSSKPTEE D

HTA3-P
MSSGAGSGTT KGGRGKPKAT KSVSRSSKAG LQFPVGRIAR FLKAGKYAER VGAGAPVYLS
AVLEYLAAEV LELAGNAARD NKKTRIVPRH IQLAVRNDEE LSKLLGSVTI ANGGVLPNIH
QTLLPSKVGK NKGDIGSASQ EF

HTA4-P
MVCNTNILKD VSTKISAFEN VRMIMVEGEM FQVARIHKQL KNRVSAHSSV GATDVVYMTS
ILEYLTTEVL QLAENTSKDL KVKRITPRHL QLAIRGDEEL DTLIKGTIIG GSVIPHIH

HTA5-P
MSTGAGSGTT KGGRGKPKAT KSVSRSSKAG LQFPVGRIAR FLKSGKYAER VGAGAPVYLS
AVLEYLAAEV LELAGNAARD NKKTRIVPRH IQLAVRNDEE LSKLLGSVTI ANGGVLPNIH
QTLLPSKVGK NKGDIGSASQ EF

HTA6-P
MESTGKVKKA FGGRKPPGAP KTKSVSKSMK AGLQFPVGRI TRFLKKGRYA QRLGGGAPVY
MAAVLEYLAA EVLELAGNAA RDNKKSRIIP RHLLLAIRND EELGKLLSGV TIAHGGVLPN
INSVLLPKKS ATKPAEEKAT KSPVKSPKKA

HTA7-P
MESSQATTKP TRGAGGRKGG DRKKSVSKSV KAGLQFPVGR IARYLKKGRY ALRYGSGAPV
YLAAVLEYLA AEVLELAGNA ARDNKKNRIN PRHLCLAIRN DEELGRLLHG VTIASGGVLP
NINPVLLPKK STASSSQAEK ASATKSPKKA

HTA8-P
MAGKGGKGLL AAKTTAAAAN KDSVKKKSIS RSSRAGIQFP VGRIHRQLKQ RVSAHGRVGA
TAAVYTASIL EYLTAEVLEL AGNASKDLKV KRITPRHLQL AIRGDEELDT LIKGTIAGGG
VIPHIHKSLV NKVTKD

HTA9-P
MSGKGAKGLI MGKPSGSDKD KDKKKPITRS SRAGLQFPVG RVHRLLKTRS TAHGRVGATA
AVYTAAILEY LTAEVLELAG NASKDLKVKR ISPRHLQLAI RGDEELDTLI KGTIAGGGVI
PHIHKSLINK SAKE
```

FIG. 7 (A)

HTA10-P
MAGRGKTLGS GSAKKATTRS SKAGLQFPVG RIARFLKKGK YAERVGAGAP VYLAAVLEYL
AAEVLELAGN AARDNKKTRI VPRHIQLAVR NDEELSKLLG DVTIANGGVM PNIHNLLLPK
KTGASKPSAE DD

HTA11-P
MAGKGGKGLV AAKTMAANKD KDKDKKKPIS RSARAGIQFP VGRIHRQLKT RVSAHGRVGA
TAAVYTASIL EYLTAEVLEL AGNASKDLKV KRITPRHLQL AIRGDEELDT LIKGTIAGGG
VIPHIHKSLI NKTTKE

HTA12-P
MDSGTKVKKG AAGRRSGGGP KKKPVSRSVK SGLQFPVGRI GRYLKKGRYS KRVGTGAPVY
LAAVLEYLAA EVLELAGNAA RDNKKNRIIP RHVLLAVRND EELGTLLKGV TIAHGGVLPN
INPILLPKKS EKAASTTKTP KSPSKATKSP KKS

HTA13-P
MAGRGKTLGS GVAKKSTSRS SKAGLQFPVG RIARFLKNGK YATRVGAGAP VYLAAVLEYL
AAEVLELAGN AARDNKKTRI VPRHIQLAVR NDEELSKLLG DVTIANGGVM PNIHSLLLPK
KAGASKPSAD ED

FIG. 7 (B)

HTA1-g

```
ctcactttaa catttttata tagtgacatt tttagtaatc caacgttatt tatatgatta
gtaattcatc aaatttatat agtgataaaa ttccacaatg gttgttcaat aaaaatatga
acaacacaat agaattagta aaagtgacta tgttaaatca tttcttcgc tggggtttgg
tgggcgagtt ctaaacccat aagcggccca tttacttcgt aaactcaatt cgatttgttc
agcgttccaa gcccataata ttattttcaa gggcataaaa taaattgagg tttatatgga
aaatttggaa attccctcgt ccagaagaaa ccaacaaaaa ctgcaaaagt tcaagcggtg
ggagaaaaaa cttcagatcg tagccattca ttaaattata atcaacggtt taaacctctt
cgatccgcgt actctattct tattggtcaa ataacttaat cctccaacat atataaacaa
caatcagatt tctctctgtT AATTTCGTCA AGAAAAAAAT TCGATTTTTT TGCGCTCTTT
GTGGGTTGTT GTTGTTGAAA ATGGCTGGTC GTGGAAAAAC TCTTGGATCC GGTGGGGCGA
AGAAAGCTAC ATCTCGGAGT AGCAAAGCCG GTCTTCAATT CCCGGTGGGT CGTATCGCTC
GTTTCTTAAA AGCCGGTAAA TACGCCGAAC GTGTTGGTGC CGGTGCTCCG GTTATCTCG
CCGCCGTTCT CGAATATTTG GCCGCCGAGg taaaattaca tcgtctttc tctctttccc
attccgtttc cgatcttatt cgtctgactc tgttttgcg tgatcgatta cgaatctagg
gttcttacat tttccgaatt tgacatgcaa aaattgaatt agattcgtgt ttgaattgaa
ttgttgtagt tctgtaattg acctaatttt gggtttgttc tgattggttg atggtaatcg
agatcatatg aatcgttgta gttttctcgc aagattctaa attttttca attatggtaa
ccaatttgat ttgagttgtt aaagttctca aatttggaaa gtttgatcat gaattgtgtg
ttttgaattt gttcagGTTC TTGAATTAGC TGGAAACGCA GCAAGAGACA ACAAGAAGAC
ACGTATTGTT CCTCGTCACA TTCAGCTTGC GGTCAGAAAC GATGAGGAGC TAAGCAAGCT
TCTTGGAGAT GTGACGATTG CTAATGGAGG AGTGATGCCT AACATCCACA ATCTCCTTCT
CCCTAAGAAG GCTGGTGCTT CAAAGCCTCA GGAAGATTAG GTCTTTTAAC ACAATGATAT
AGAACACGTC TCTCTTTTGG CTTTAGATCT AATAACCTAA TAACTAGCTA GATGTTTTCA
CTTTTTGTAT CTTTGCTTTT TTTAATTCCT TTAGGGATTT GTTTCTTTCC GTTTCTGTTT
CGACATGTTG TTTCTGTTTT TGTGAATATA TGAAGTATT TTGCgaaata tgaatgataa
tgtctttcaa aaatgctgat gccttattca acaagcaaac actgcacttt gtagaagtat
aaagattttc tttgttgttg atagtaatag tacaagaaag aaaaaaacac aaaggattat
tattctatgg ccaacaagat tgaaaaaata tgaaagaaa gtatttctaa gactaaa
```

FIG. 8 (A)

HTA2-G
```
tgtggctttt cagccaccac aatatgtcat acaacttgca actgttatta tccaaattta
aacccacata aagaatacgt ctaaaaagca aacaataatc attacaacac ttagtaagtt
ataacttctc cctaacttct ttgaaatttt gataaaaagg aaaatacata tgtacaagaa
gtgaagaaac aatttatttg ggccgaacag tgttaaattt tgggccagat aacgttaaaa
taaaaaggag tatttctatt taacaagccc aatatagccc ataacaat ccattgaaat
catcggagaa ccaaaaaaag gacaaagcag gtgggcgcac gaatctcaaa tcacgtccct
taaacttgta acaatctgac ggtgtagatt atcgatccat gcagtgtcat atcattggtc
agaaatattt tctatctcgc cactatatta atcatcatgg cgggtttcgc tgatactcat
tattgttatt tttgacagaG AGAAATTTCT CAGTTACGCT TCATCCTCCT CTAAGAGATC
TTTTTTCTAT CTTGGGTAGT AGAGAGAAAT GGCGGGTCGG GGAAAACAAC TTGGATCTGG
TGCAGCGAAG AAGTCTACTT CTCGTAGTAG CAAGGCTGGG CTTCAATTCC CTGTTGGTCG
TATCGCTCGA TTTTTGAAAG CCGGTAAGTA CGCCGAGCGT GTTGGTGCCG GAGCTCCGGT
CTATCTCGCC GCCGTTCTTG AATACCTCGC CGCTGAGgta atcagtctct tctatttatc
acctgtttaa tttactcttt ttaccgaatt aaatggttat agcttgcatc tagggttctg
gattttagat tttcttaccc ctttcgttaa attatgcgaa atttggaata ttttagaatg
cattagttcc ttagtttgtt ttttcttgg gaaaaattgt ccatttttt tgtgtagttt
tgagctcaat ttgtgtttct ctgtgctcat catgcttatc gaaattaggg ttaaatttgt
tccttactac tttgagttat catagttggc actgattgat actgtcaatt gtgttctcaa
attcgaaaaa tgttgttgtt cacttagttt tgtctttgga tatgtgaaca tgtctgcttg
ggaactgaat ttggtgcgct cactttctat agGTACTTGA GCTTGCTGGG AACGCAGCGA
GAGACAACAA GAAGACCCGT ATAGTTCCAC GACACATTCA GCTTGCTGTG AGGAATGATG
AGGAGCTAAG CAAGTTGCTT GGAGATGTGA CAATTGCTAA TGGAGGAGTG ATGCCTAACA
TCCACAATCT CCTTCTCCCC AAGAAGGCTG GTTCATCTAA GCCTACTGAA GAAGATTAGG
TTCATTACGA AGATAGGGAA AGCTGGAAAC TGGTTGATAT CAGATAATGC TTAGGATTGT
TTTTTTTTTC ATTTGCTTTT CCTCTGCAGC AATGGAAGCT GTGTGGTTGT ACTAGTTGTT
AAGGTTACCT TTGTTTCACT TTATGTGAAT ATATGAAGAA ATTGTTCTAT TTCagtcttg
actccacttc tttagcattg ttcactgatt catttgttgt tcctgaaagt caatttaaat
tccttcgata agctacacga aactgcacac atagtcacat gtaacttgtt tttaaacttt
ttgttttgtt ttgttttgg ttgaaaactc gagaaaaaaa gaatcagtag acccataatc
acagaaaagt caagccacca agcgattcga catagacagt ggagaagtga cgagattgag
agaatcgagg cgagagagag agagagacag ggacgattcg gtttagagct ctcgtatgag
gtatatttca atttcgtttt cggcgatatc ttgtgtcgca aat
```

FIG. 8 (B)

HTA3-G
```
gtttgactttataaaaacatgcagaaatgtacaaagaatatatacatataattatcttaa
ttaatttaataactatcaatctgtcatactacaccactatcaatctatcatcatcaccac
cattatgcttgacagtcactttttagttggcccatgttaaagctgtttgtgttatttgtt
attgggcttatccttcactaccatttgattgaaatttatctcatgacccaacaaattgag
ctaatttcggttcaacattggatgttaattttttttcaaaccgaaccgaattatagtttt
ggtgcattttttctaaaccgaattttaacacaaatagtaatcgtcttaaaaaattcaccg
acttgttaaaaagaggcggaaaaaaaaaccocgcgagaacttacaatggtgccacgctggc
aatccgcgtgactcacaactaaccaatcaaaatccattatctcaacgctatatttcag
aaatcacaacctaaaccctAATCACTCCACTCACAAAATCCTCAGCCATCTCTAATCAC
ATTTTACAATCGCCTCTTCAAATTTCCCGATAAACAAAAAATGAGTTCCGGCGCCGGCAG
TGGAACAACTAAAGGTGGCAGAGGAAAGCCAAAAGCTACAAAGTCCGTCTCTCGATCTTC
TAAAGCTGGTCTTCAATTTCCCGTTGGAAGAATCGCTAGATTCCTTAAAGCCGGTAAATA
CGCCGAACGTGTTGGTGCCGGTGCTCCCGTTTATCTCTCCGCCGTTCTCGAATACCTCGC
CGCTGAGgtacaaacaatctctgtttggtatttagtctttagtctctatgatgagaa
tcactcgtaattgatatatcactagattttcgatgtttaccgaatctttgattttgatt
tgatgttaaggtgtcttctagagtctgatctcttatatgatgttgatataatcattagGT
ATTGGAGCTAGCTGGAAATGCAGCAAGAGATAACAAGAAGACACGTATCGTACCACGGCA
CATTCAGCTTGCAGTGAGGAACGATGAAGAGCTTAGTAAACTTCTTGGAAGTGTAACAAT
TGCTAATGGAGGAGTTTTGCCCAACATTCATCAGACTCTTCTCCCATCAAAGGTTGGAAA
GAACAAAGGCGATATCGGATCTGCTTCTCAAGAGTTTTAATTTTATTTTTAGCTTGTAA
CATAGACATGGCTCTCTGTTCCACAATAGTTTTGGTATTTTCATGTTACTCAAAAACTGT
GTTTGCAAATCCAGTAATGAATTCGGTTTGAAGAAGTGAAATAGTTAAATTTGATGTGTT
GAAATAGCGGATTCAATGGCTTCAATACAAGTGCTAATAGGTTGGCTTTAGCCATGGTT
TCTGCAAGTGAGACTCTTGCTTCTTTGTGAGAATGTAATAATGAGACAGTGTTGGAAACA
GCCCATTTGATATGAGCCTCCTTTTCTGATTctgtgaagccgagccaccgcagaacatcg
ttcaactgcaacactcaaatctcaaaaaatacattagaagattatagtctcatgactatg
agtggaaggagacttgagtttgtattacctttgacaatatctgagtatag
```

FIG. 8 (C)

HTA4-G

```
ttaagactga taagtatcaa caagcgaagt tttgatttgc ttgttgaagc tagtctcgga
cttcaaatga cacttgatat gttcatacat gtaacatgtg aagaagaact tattttggaa
cccaaagaca tgaatagttt gaaaaccttt ctcatgagaa tatgcaatgt taagatcttt
tacttgtctt atgacactct ataggtcagt cccatctttt ttgttaaagt ttacaattga
caattagtta gtgatgatat agttaacttg gttttgttt cacgaactta atgactgaag
ttaaacaata caggtattca acaacctgat tcagttaact attttgccat gtatagagag
ggaatcactg ccaaatctac tcaagaattt tccaaatcta gaaaccttct tctatgaagt
aacatacaca ttcttgatat taacaactga catgatttta cacagtaata aattttgaaa
cggtctcatt ttatgtttcA TGGTGTGCAA CACGAATATA CTAAAAGATG TGTCGACGAA
GATAAGTGCT TTTGAAAATG TTCGGATGAT TATGGTGGAG GGAGAGATGg tatgatagga
gaagtctttt gctcatagaa gtagagtgct aacagttcac aatgacttta caatctatgt
ggctccttga aacaataaac tatggatgtg cataactaat ggacaatctt catatttagg
aatgactaaa atatcttaac taatgcttaa acactcatgt gtcaccaaat aacaatacat
ggaacatgag tgtcaataat gaccttgtat tgtaatgggt cgctggttta gttgaagttc
cagtagcaca taccgaaact acattccttt tttatggagt aattctgttt taggatattt
ttagggtttt tggatttgt ataagacaaa aaaaaacaca aacacaataa gctacttaac
tagaaaataa catcatcata taatttgact aaataaacaa atcactcctt cgtggttttg
ttgatgagag acatgtggat gtgagagact actccttatc caccaattgt tactttgata
aatggatcaa gatccctatc tcctgcgatc accaactata aatgcattag agtaatcctc
tttatttct tatcattgat tgtgttttc ggtaactcaa taacctatga agttaggcac
tctaggattg aagccatgta gtcaacaaca atagcaccaa gtcgaccatg ttgtagatac
tctagtcttg agttgcatgt gaatacgacc cactagaaat tgaaataaac aaagaaattt
cattttttgt agtataattt gataaaattt tatactgata ttgtttcttt gtttctttca
gTTTCAAGTG GCTCGTATTC ACAAGCAACT TAAGAACAGA GTTCTGCAC ATAGTAGTGT
TGGTGCGACT GATGTTGTCT ACATGACTTC AATCCTTGAA TACCTAACTA CAGAGGTTCT
TCAGTTGGCC GAAAACACTA GCAAAGATTT AAAAGTGAAG AGGATAACTC CAAGGCATTT
GCAGTTGGCG ATCAGAGGAG ATGAAGAGCT TGACACACTC ATCAAAGGAA CAATTATTGG
AGGAAGTGTG ATCCCTCACA TCCACTAGtc tcatcaacaa aacaaccaag gagtgatttg
tttcttaagt taactaatat gatgtgatat gctagttaag tagcttatgg tgtttcagtt
actctagttt tggatcggag aagtagttta agtgttaagt cttgagacat cataatttta
cgtctcatct cgtaaacgat aggagaagtt ctttgctcct agagttttgg tgctaaacaa
ttcacagtga tatgcattcc atgtggctcc ttaaaacact caaccatgca tgcacaagca
gtggaccatc ttcatattca tgactgacta aaatattgtc atcaatgctt actaatatgt
caaattgtag taactcggtc gtttaattga agtttcattg ttatatatat ggcgtatagg
cctaaagttg tatgaagttt tgattgatga gttaagacat cgtattatat aaagtaggat
tttcaagtta ctaactcaac tgattaagac acaagtcaag tactttga
```

FIG. 8 (D)

HTA5-G
agtaaaagga gatgtacgaa ccatagatca cataataatt gaaagggtag atgatctgcc
acgttggcaa tccgtgtgat ctaaagtcta acaaatcaca atcaatctta gtagcctata
tattgattta ttcttgttgc ttgatcaata aaggttacat catagaacta aaatcatatg
aaaccgaatc gatcaaccct ggccatcttt taaataacca tcaatacatt gggatgatca
atccacaata aatgtattga tgtaaattaa aaatatgaac ttgtaacaga tcaagattca
gggtctaaaa ttatagaaag cttaataatg gaggactatt tcactaaaat cacttttcgt
ttgtacatta ttttcaaaaa gtaaaaggag atgtacgaac catagatcac ataataattg
aaagggtaga tgatctgcca cgttggcaat ccgtgtgatc taaagtctaa caaatcacaa
tcaatcttag tagcctataC ATATAGAGAA GAGCAAAACC CTAAAGCCCA CTCATCTTCT
CAATTCCCAG ATCATCTACA ATAGTCATTT CTCTTCGATT TCTTCAAACT CTCATCAAAT
CGTTTATCTG TTCTAAATTT CGAAGAAGAC GATGAGTACA GGCGCAGGAA GCGGAACAAC
CAAAGGTGGC AGAGGAAAGC CAAAGGCCAC CAAATCCGTC TCTCGATCAT CTAAAGCCGG
TCTTCAATTC CCCGTCGGAA GAATCGCTAG ATTCCTCAAA TCCGGTAAAT ACGCCGAGCG
TGTCGGTGCC GGAGCTCCGG TCTATCTCTC CGCTGTTCTC GAGTACCTCG CCGCCGAGgt
aatttatttt tcttgtcttc caatttggtt ttcaatttcg atttggtcac atctgaattg
gatcttgtac tgatttgatt ttgatttggt ttgggttgat agGTGTTGGA GCTGGCGGGA
AACGCAGCAA GGGATAACAA GAAGACACGT ATAGTACCAA GACACATTCA GCTTGCAGTG
AGGAACGATG AAGAGTTAAG CAAACTTCTG GGAAGTGTGA CGATTGCGAA TGGAGGAGTT
TTGCCAAATA TTCATCAGAC TCTTTTGCCA TCCAAGGTTG GCAAGAACAA AGGAGATATT
GGATCTGCTT CTCAGGAGTT CTGAGGTTCT TAGACTTCTT AGTTCAGTTC TCTTGTTTGG
ATTCGGAACT TGTAAAATAG ACCCTGATGG TGTTTTTTGG GGATCAAATT AGGTTTTAAA
GCTAAGTATA TTTGGCTTTT GCCTAAGTAT GTTAATTAG TGAATGATAT GATATTTCGG
AACGAATCAT GTATCAATGG AActgaatta atcgatatat caacccagaa acattttgaa
acacaaacta tgcatacttg attctttatt gcagatacat gcaactcatg gagcctaata
ctaaacattg ctttgatcat gtttcaattt aaccagactc attttttaat tcacccaggg
agtaaaactc attaggtttt gggcctaact gcctcagtca tggtaatcct gaattaactt
cactaagtta ccctcatctg ttggttcgca cctgaattag ctcgctaaat taccttcatc
t
```

FIG. 8 (E)

HTA6-G

```
gtctataaac tattaaactc tagggtttaa tatgtacaaa ttctcttagg ctacttttga
ttaggactcc cttgtgaatg tcaaaacata atgcgacccc aaaatatctt tataagtata
attgttaatc ttttgattct aaaatattgt tcattgtttt ccaattaggg cttcaaagac
tcttgagaag catcattaaa catttaaatg tcaatgacta actttacatt taacatataa
ttaatctacc gaaaattagt gtaagttgca agaaattatc caaaaaccca aaataaagca
agcgctaaac ttttaaaatg ctacaaaaaa actggcgccg tttcaaaaag catacctctt
tttgattggt taatacatag tcacgcggat cgtgctttat ttgaacatcc accgtcgata
gactaaatcc aacggataat aatcctctcc cttctttttt tttcatttac ctataaatat
cacagagtac ccttcaactT TAAATCACAA ATCTTCAACT TCCGATACTT TCAATCTCTC
TAAACTCTCA ATTTCAGTAA TCGATAACCG TAGCAATGGA ATCCACCGGA AAAGTGAAGA
AAGCTTTCGG AGGAAGAAAA CCACCTGGTG CCCCAAAAAC CAAATCGGTT TCGAAATCGA
TGAAAGCCGG TCTTCAATTC CCAGTGGGAA GAATCACTCG TTTCCTGAAG AAAGGACGAT
ACGCTCAGAG ACTTGGTGGT GGTGCTCCGG TTTACATGGC CGCCGTTCTT GAATACCTCG
CCGCAGAAgt aagtgtttcc cgatctggat tttctagtaa gatttttttt ttacatttca
aaatcaattt tctgattcga atttattgat ctcagGTTCT GGAGCTTGCT GGTAACGCTG
CGAGAGATAA CAAGAAATCA AGGATAATTC CGAGGCATCT TCTTCTCGCG ATAAGGAACG
ATGAAGAATT GGGGAAACTT CTGAGTGGTG TCACAATCGC TCACGGTGGT GTTTTGCCTA
ACATCAACTC TGTTCTATTG CCTAAGAAGT CTGCCACTAA ACCAGCTGAA GAAAAGGCTA
CCAAATCACC AGTCAAGTCT CCAAAGAAAG CTTAATCTGC TAGAGTTTTC GTTGCTAGTT
TGTGTTTGAG CTCTGGTGAA TGTAGAAATT TGAAGCTTTT GGATCTTAGT TTCTATGTAT
TTGGTGATTT AGAATGTTGT TCAAAATCCT TTTCCTAATC ATAAGAATTT ATGATCTATC
TATTATACGC TTCGTCTAAT CTTTTggtcc actcgtcgta atgtcattag tgaatattta
ataaacaact ttgtcatcga cattaacgaa cccttttatt cgctgtgcta aattttcctt
ttaggtgaag ccaaatctaa catgttctct tctctctttg ttcgttgtaa ttccataaca
tctccattac gatgttttgc gattcgagga tcttgttcta aattatt
```

FIG. 8 (F)

HTA7-G
```
cgtggtatat acatacacgt cgttctttcc tcattttaag tcttcatttg tcatggagct
tagaagatta cagttgaata tcttaaactc tctttcttaa tcacattttt tgtacttatt
acactaatta aaaccagagt ttgggtaata attttttgttt ccttaattttt ccgaattatc
cgctaatttt ctactctaat tctctggata ttttaaataa tagtaataat ctgctgtcaa
aataagataa gaaaaagaca taaagctgat tatcttgtag aacgtgtggg gaatgaatct
aacggctgat atcactcaag tgttctttttc caccttcctt ttacaacacc cacgtgtaat
gtcatacaaa gaagtcatta cgaccgttag atcaaagcca acaagatcca atcttaacgg
ctaagataaa ttactacacg gatcgccaac gtggcaatac gtggtatata catacacgtc
gttctttcct cattttaagC AAATCGTAAA CCGCCACAAA ACCGAAAAAA ACACTAATTG
TGCTTTCCCT TTAGATTCAT TTGTATTTTC TTTTGGAGCT TTGAACAAT GGAGTCATCA
CAAGCAACGA CGAAGCCAAC GAGAGGAGCA GGAGGAAGGA AAGGTGGAGA TAGGAAGAAG
AGTGTTAGTA AATCTGTTAA AGCTGGTCTT CAATTTCCCG TTGGTCGTAT CGCTCGTTAC
TTGAAGAAAG GTCGGTACGC TCTCCGATAC GGTTCCGGTG CTCCGGTTTA CCTCGCCGCC
GTTCTCGAAT ACCTAGCCGC CGAGgtatat tcaatctcag atctcgttgc attttgaatc
gatttatttt gtgtatctat tagatctgtt taatttgaa gttctaatga attgaaccgg
tttggtttag GTACTTGAGC TAGCTGGGAA CGCAGCGAGA GATAATAAGA AGAACAGGAT
AAACCCTAGG CATCTATGTT TAGCGATAAG GAACGATGAG GAATTGGGGA GATTGCTTCA
TGGAGTTACT ATTGCTAGTG GTGGTGTTCT TCCAAACATT AATCCAGTTC TTCTTCCTAA
GAAATCAACA GCTTCTTCTT CTCAAGCGGA GAAAGCTTCT GCTACCAAAT CTCCTAAGAA
GGCTTGATAA AGAATAGTAT CGATGTTGCT TTTTGGTTAT ATTCGGATCT TAGATGAAGA
AGAAGAAGAA GAAGAAACAA CTTGTTTTTT GTTTAGAGG ATTTGTGTAG GTATCTGAAA
TCTTCTTCTC TTTGTTTTGG TTTGTCTTAT GTAAAAACCA TGGGAAGATG ATTATGTTTG
TTAACGCAAT TTGTAATGGA AAATAATTAA GTTCTGGGAT TAGTaacttc atctgtctaa
ttaatttctg ggtttcgtac ttgttgattt aaacaattta ggtggattaa ttgaaatggt
tttggtatac acatggaaag attcagtaca gttaatgaca ttaattaaag tagataataa
tcacgaaaaa catgacatta attaagaaaa tgattgttca aattgggctt tgtttgggct
tagttgatag gcccgttaga atttatgttc ttggttcatc tacgagattc tggaaaaggg
gttttggttt tccggtgggg tttagaattt aaacaagacg cgatttcgaa tttcgttctt
gtagaatcaa attgtttggt ttcaatcttg gatttgcgat gatgaatttt ctggttcgat
```

FIG. 8 (G)

HTA8-G

```
cacacttaaa tctttctttg tttaataaaa agtataatca aaaatttgaa agagagaata
cgtttcatta ttttttttaa ataccatcat gagaggtggt atgaatatcc actatatttt
aactacaaat cttcttttga ataatttgca attttatgtg atataaattt ttagtaaaat
aattattttc caacaacaca agatttgaac gaattttgta aagatatcta aatataaatt
taacatgttg acccaaaaaa tgaagaatta taacaattta gaaaagccgg cccaacaaga
tccacaagag ctaaacaaaa tccggcccaa caataagtcc aaactttaaa agctctcccg
cacaattttc gagcatcccg ctctcgtttt caggtacttc cctctctgag ctagggtttt
AATTCGACGT CTCTCTTTTG TCTCTGTATC GATTTTCTCG CCGCGAATTT CGAATAGGTT
CTTCACCATA AGCTTGAGAT CTTATTTCTC TACTGTTCTT TGCTTCTTCT CTATCGgtta
attatcttct ttgatttcga cgacggatct ggaaattctg aaatttttgtg aagctctttt
cttttttgttt ggtttctgta gATATGGCTG GTAAAGGTGG GAAAGGGCTT CTAGCTGCGA
AGACGACGGC AGCAGCTGCA AACAAAGACA GTGTTAAGAA GAAATCCATC TCTCGCTCTT
CTCGTGCTGG TATTCAGgta tccctcaaac cctagctcct ttttgagaa tcgagtggct
cggagtttga atgtgcgtta ggttttttttg attatgttca attgtgaatt gggaaccaga
tttgtatttc gttctgtgtt taatgcattt ttgggaaatt gcttcctctc tgatttctgg
aaatatgttt tactctgtgt ttcttcatta aagttacaat gtgtgcttga tactggactt
ttattgtctc tatgactcta tgccaagtag cattattttt ggtgtgtctc attttatgac
tgtgatatgg tagcttgcat gttctatacg gttgatacac acaagcttga tttctctgtg
tgcacttctt gtagttgcgt atgaagaaaa acagtgctat ctatctagat tctagagtaa
tttgtataca atagagtact accaattgat actgagcctt aatgggagca tctacttgtc
ctctctgtgt gtgtgttctg gaaatctaag ccaaacattg tcctgttatt gtcattagtt
tactttggg attcttcctt gttaaagccg aattgtacat atcattgaat ccatgttact
tatatggctt attgctgcag tgtctttat tatgataatc acttgatacg ttgtaatatc
tatctataag atgtagtaag tgaatgatca agcaaattaa aggactgtgt ggttagttta
agtgtcttat taatatatat ctatctacaa gaagatctgt ctcagtctga ttaatgggaa
gcctttctct gtgccctaaa gttatgtgct tattttgttt tctcaatgtg gtattctttc
agTTTCCAGT GGGTCGTATT CATCGTCAAC TCAAGCAAAG AGTTTCAGCA CATGGAAGAG
TTGGTGCCAC TGCTGCTGTT TACACTGCAT CAATTCTAGA ATACTTGACT GCTGAAGTAC
TCGAGTTAGC TGGAAATGCG AGCAAGGATC TCAAAGTGAA GAGAATTACA CCAAGACATT
TGCAGCTTGC AATCAGAGGA GATGAGGAAC TTGACACTCT CATCAAAGGA ACCATTGCAG
GAGGAGGTGT GATCCCTCAC ATCCACAAGT CCCTTGTCAA CAAAGTCACC AAGGATTGAG
TTTCGCTCTC TGAGTCCTAA GTCTCTATTA TACTATGTGC TCTTTTCTAG ACGCCCTCAT
GTGTATATGG GTTCATTGTA TCTCTTAGGT CTCTCGTTTT AGACTCATAC TCTTGTTATT
TTGCTAATGC TTACATGATT GAGGatgatg gttcttgctt tcttggtttc ctatactgtt
gcatgcccct cttctagcta accccggaca atagaaatcc tcgattagat gatgaaaacc
attcaacatc tatgtagcaa ctgatgacaa cagcgtttga ttgtttcaca a
```

FIG. 8 (H)

HTA9-G

```
ttagggacga atttgtgatt tatgattatt tgactttaga ttgggcttgg gctttttcg
caggttgggg tataagggta aaatcgtcat ttgacagacc gacttgtctc tctctatctg
gggaaaacgt cttttcacat caacaaagaa ggaaaaaccg cagagaaacc atctgatact
taagctaaac tgagcgtaca aaaagcctct atatgtctta gttcatgatt tgctatgttt
tgtttccaga ctgaatgatt atacagagaa aacaaacaaa gatctccctc tcttcttttg
aatcaaaaca tgggtgttaa aatttaatag ttttctttca agtgtctttt tcaatattga
actaaattta gggacgaatt tgtgatttat gattatttga ctttagattg ggcttgggct
tttttcgcag gttggggtat aagggtaaaa tcgtcatttg acagaccgac ttgtctctct
ctatctgggg aaaacgtctA TCGGGAGACT CCTCTTCGAG CTCATCTTCT TCTCTCTCTT
TTTATCTTTG GTTGTGCGAT CTCCTTTCTC TTTCAATCTC CAAGGATTTT ACTGTGAGAT
ATTTGGCGGG AAAATGTCGG GGAAAGGTGC TAAAGGTTTG ATTATGGGGA AACCCAGCGG
TAGCGACAAG GATAAGGACA AGAAGAAGCC TATCACTCGT TCTTCTCGAG CTGGTCTCCA
Ggtagattat aatctccctc acactctaag tcttccgtgt ctgtttcttt gggaatcgaa
atggtcttat acacctgaac gattagtaga tcgcgtttaa gtggtagatc gatgagattc
tgagctagat ttggtaattt cagctgagaa ttagagacat tgggatgcga gatttggttt
tctattgtgt tatctgctgg agaattgttt cattaagctt ttatggttga tattgaaccc
gatctttgat ttcacggagt cttgttgtta cagctacctt gtgaattgaa ttcggagttt
ttttgtaga gatttattgt catatatgaa atgtttctgg gagcaattga gatttgagta
ttcatttagg ttccattgtt gtggctaatt gaatttacat tgtgtgcagT TCCCAGTTGG
TAGGGTGCAT CGTCTGTTAA AGACAAGGTC CACTGCTCAT GGAAGGGTTG GAGCAACTGC
AGCTGTTTAC ACAGCAGCAA TATTGGAGTA TCTGACTGCA GAAGTTTTGG AGTTGGCTGG
TAACGCCAGC AAGGACTTGA AGGTGAAACG TATCTCGCCG AGGCATTTGC AGCTTGCGAT
TCGTGGAGAT GAGGAGCTCG ATACTCTCAT CAAAGGAACT ATAGCTGGTG GTGGAGTCAT
CCCTCATATC CACAAGAGTC TCATCAACAA ATCCGCCAAG GAATAGGACT TTTTTAGTTA
CCCGCTTTGT TCTGTGTTGC TTTTCTGTTT TCTAAATGTT TTTAAGAGTT GTTGTTTGAT
AAGATGCTAG AGAAGCTCTT TTTAGGATCG TTTGCTATTG TTCGTTCGAT CAGCGTACTT
TGTGTTAGAG ACGCCAGTCG ATTTATCTAT CTTTAAAAAT GTATTCGAAT GATTATCCAA
AAACCATTTC TGActaccta ccttgctggt ttgttcgctg gagaagcttg aaagcaaatt
cattgggaag gatttgtatt atctctaaat agaattcata tatacatcat acataagtaa
aaatcacagg tttgtgttta agaaaattag gctgataata ttcacttggc ctagttgacg
tcgatgtgat tctgaagcaa agttctttgt agcaaatctg gtgggagttt taatcccttt
aagaatacac tgatgcctga ttt
```

FIG. 8 (I)

HTA10-G
```
attcgaatta tgaaaatcaa aaaggaatga agcgggaaca aaaccttggg gatttagttt
gaatcgtgat gaagaaggaa gatcagagct tgagggagat tcgaaatttc ctcgcttcat
aacaaaatct gagaaataga tttgaaaaac agacaacact aggttacaaa aactgttact
cgatgaataa aaaagagga cttttcaaa tcttcacaca caaatttcac aaagaacccg
gattcaattt ttgaaaattg ggctctttgg taaaatgtaa aacgtttggg ccgaaaaaag
aagaaaaaaa caaaactgta aagaggcaaa gaggatattt tggtaattca ctctgacgcg
gatcctgaat ctcgaattat tcaccgttga ttataacatt atctaacggt gataaacagc
gatccgcgta gtttcttctt attggttaag acgaatctaa aacagtatat aaactctgga
gaagatggag agagtccatA ACAACAAATT CGATTCTTAT AACTGTTTCC CTCTCATCTT
TACACAAAAG TATTCTAATC GATTTCAATG GCGGGTCGTG GTAAAACACT CGGATCTGGG
TCTGCGAAGA AGGCAACAAC AAGAAGCAGC AAAGCCGGTC TCCAATTCCC TGTGGGTCGT
ATCGCTCGTT TCTTGAAGAA AGGCAAATAC GCCGAACGTG TTGGTGCCGG AGCTCCGGTT
TACTTAGCCG CCGTTCTCGA ATACCTCGCC GCTGAGgtaa ttcctcttcc ctattcttca
aatttcgat cttttagttc aatttctata aaccctaatt ttgactgatt ttggggaaat
tttgaaaaat tagGTATTGG AATTGGCTGG AAACGCAGCG AGGGATAACA AGAAGACGAG
GATTGTTCCA AGGCATATTC AATGGCGGT GAGGAACGAT GAAGAATTGA GCAAATTGCT
TGGAGATGTG ACTATTGCTA ATGGAGGTGT GATGCCTAAC ATTCACAATC TTCTTCTTCC
TAAGAAGACC GGTGCTTCCA AGCCATCTGC TGAAGACGAT TGATTAATCA ACCAAATCCA
CTCTCTTGTG TTTTTTGAGT TTTTAAGGCT TTTTAAGAGT AATTTAGATT AGATCTATGG
TGAAGAAAGA ATCTATCTTC TGTGTTTTTT GAATTGAATT GAATGTTCAT ATGCTTTCAA
TTTCTTATGG AATCAAGATT TTAACTTTTC Taggttttcg agttatgatg atgaaattct
tagtcttata aatcactaaa gacttgggat ttttgattgg ttgacataaa gaatggactt
ttgagttaaa tttgggaaag ctactgggaa tgacatcatg agaggtgtat aattgagcaa
ctatgacata tattaaaaga gatctgaagg attgatgatg attggtgggc caataatg
```

FIG. 8 (J)

HTA11-G

```
tcttaacaat caaaccaaag catataatat tctcttacca tttagtttta ccacaagcat
agtgcctaca acctttctca tgaaaaatgg atctttctgt tacaaaagaa aaaaaaaagc
tgatttaaa cgtttctaag aaatagaggg cttaatggca aaatgttgaa acattttaag
gctccaaagc gaaaaattta accgccaaag cgtaggtttc cccccaagat tttgaaaata
tttaaaaact cccaccaaac tttttaattt taaaactcta atcccattct attcaaccag
atttcgtttc tttcgtcctt ttttCCTTT TGCATTCTCT CGTCGTCGTC TCAAGgtact
ttacttctct ttttctctct tccaatattc gagatctgtt tctgtctttc ttggatcgat
tctcgattct gttcttcgat ttagtcttct ttcgaataga tctggtagat ttaagcatta
tactcttctt tttctgattt cgttttgtt tgactgtgta cggttagATC TAGAAGAAGG
AAACAACAAT TTCAAGAGAC ATGGCAGGCA AAGGTGGAAA AGGACTCGTA GCTGCGAAGA
CGATGGCTGC TAACAAGGAC AAAGACAAGG ACAAGAAGAA ACCCATCTCT CGCTCTGCTC
GTGCTGGTAT TCAGgtcatc tcttaaaccc taatttcgac gaccttgttt gactctgatt
ctttcctaat tcatcagtac catttacatt tttaggaata gatttgtttt tttggttcta
tgtaaaagca tgaggaagta aacttgctgg atatgtgtaa tttcttttac tcggtaccat
gttgatgttt ttgtcaatgt ttgtgctaat tatacaaatt tgtgttgctt gctcactggt
tgcttggtca tctgagaata catgttgttg ttgtttttgt ctccccattg tttaggtagt
gtcttatggt atgtgcccaa atgttccctt actctgtagc ttactattga tattgatgag
tcatgagggt tttaatatgt tttgtttggt tctagtatgt gcaatgttct gttttttatt
aagttatact attttaatgg aactatttgg tgtgcgctga tactgttttg acattgatgc
tgtgcatagc catacaagta gagagattgg tcacaccgat actgtttttt tttttcagTT
TCCAGTTGGA CGAATTCACA GGCAACTGAA GACCCGAGTC TCGGCACATG GCAGAGTTGG
TGCCACTGCA GCCGTCTACA CAGCTTCAAT CCTGGAGTAT CTGACAGCAG AGGTTCTTGA
GTTGGCTGGG AATGCGAGCA AGGATCTCAA AGTGAAGAGG ATAACGCCAA GGCATCTGCA
GTTGGCGATT AGAGGAGATG AGGAGCTGGA CACACTCATC AAGGGAACGA TTGCTGGAGG
TGGTGTGATC CCTCACATCC ACAAGTCTCT CATCAACAAA ACCACCAAGG AGTGATGTGT
AGCTTTTTAT GGTGTTTGTA TTTCTGTAGT CTTGGACTCA TTTTCCTTTA TCCTTTTCTT
AGTTCTTTGA CTAGTGTTGA CCTCTTCTGG ACATCCTCAG GTGTACATTA GTTAATTTGA
ACTCTTTAGG TTCCTTgttc aatcatatgt tctctttcta tgctattgtg atttgcttat
tatgttttca agtgaaccgt tttctgtttt aaacaactga ggaaatcatt tactcgcatg
ctctctggta accggactta caagtatctt ttagatatag aacttgttat caaacatcat
cagtatttta tcaagtcaca tattccaaat caggcgcaaa tagcccaatc acaagtcaaa
gactcaatat taaaaaaaaa agagtacatc attcattcac t
```

FIG. 8 (K)

```
HTA12-G
gatttagtgt ccaatagaaa gcatccaagt ttttgccaaa aaaaaagaaa gaaagcatcc
aagcaataca tataagtttc atttgcatta tattcaacag taccattttc atatcttgtt
tcaaaaaata catcaaatta ttttccaaac cttcacatat aatttgagaa gaaatattac
aaatttaata taggttcagc ataatttaga aaatattatt caatgtttaa aacttctcct
aaattttgga gtattgctat taatccttt aatgtgaaca aaacattgaa gcgaaggttg
ccagatcagc aaatcatagc cgttgattca cttccaatcc aaaagctaac attcatcaac
tgacaaaacc aaccaaccaa ccaacttctt tcgctatctt acgccaaagc tctcttaatt
cctccgtttg catattttcc ggtcagatca aaatcagaat cagaatcaaa tttctcgtcg
tgtcggagta aatcaagccA TGGATTCCGG AACCAAAGTG AAGAAAGGAG CCGCTGGAAG
AAGAAGTGGT GGAGGTCCTA GAAGAAACC GGTTTCCCGT TCGGTTAAAT CCGGTCTACA
GTTTCCTGTC GGTAGGATCG GTCGGTATCT TAAGAAAGGT CGTTATTCGA AGCGTGTCGG
AACCGGAGCT CCGGTCTATC TCGCCGCCGT CCTCGAGTAT CTTGCTGCTG AGgtaataaa
gttctgaatt cagatcagct aatcatttca tcggaattat cgcagtttca tcgatttcac
tagaattctt gtgggttttg ttctgttgct tcgttgacca tctataggtg tagaatgtct
tcttctgatt ttagggtaaa ttgataatca tctgaggttg taaaattgaa tttgttagat
actatatcac gagtagatca acctcaagac atggtttcac tttcaattag gtttaacatc
tttgctttgc aaatctcaaa atcttagata gagatatatt agcgttacat aaaaactaaa
gttgcatagt caataaaacc taaataaaac atctgcaagt aaacttcatt gagaatctat
catcatgtaa caccgttttg agaatctgaa taccttggac tgatgtgcat gttacatgta
actcttgtca acaaatctct gagtaactag gatatgcaaa tattgcatac taatctttt
gatcgaatgt gacaaaaccc catttttaaag tttacaagtc tgatccgtta tatatatgtt
gtcgatttag GTTCTCGAGC TTGCTGGTAA CGCTGCAAGA GATAACAAAA AGAACCGTAT
TATACCACGC CATGTTCTAT TAGCGGTGAG GAACGACGAG GAGCTAGGGA CACTACTCAA
AGGCGTAACC ATTGCACACG GCGGTGTTTT ACCAAACATA AACCCAATAC TCCTCCCAAA
GAAGTCTGAG AAAGCAGCTT CAACTACAAA AACACCCAAA TCACCATCAA AGGCAACCAA
ATCCCCTAAG AAATCTTAGT ACTTCTTTCT TCATTCCTCT GTATAACCTA CTGTTTCTAT
CTCTCTGTAC GTTTCTCTGT AAAGACAGAA CAGAATATCT CTTTGTTGTT GTGAGAAAGC
TTAGTTTCTC TGATCGTCGT TGTGAAATAA AAAATGCAAC GTTCATATAg attttgcac
aatcaaaaag tattcatata aacaatgtat tattattcga ctatcatcat atg
```

FIG. 8 (L)

HTA13-G
```
ttaatacgac atgctaaaaa ttgattaatc atgtttagaa aaatatatac tatgataaac
ctgaaattgt gtcacacaat tttgatgaat gtatatacca catttccata ttatacgttt
taaaagtaag attttcataa attttaaaat tattcataac attcactaaa attagatgtg
tataattaac aaactaaaaa tatcattaat ctactatttt agtagttatt ttgcgaaaat
atgtttgagt tacaaaatat tttcactatt taaatcatgt cgattatacc cactgaaggg
tatttccgtc aatcccaatt ctaacaatga attcaggagt ataaaaacgt aaattcaagc
gtgccaatta taaaccgtcg atcataatct aatccaacgg cagtaacatc gatccgcgtg
attgtttatt attggataag aatcactcaa ccgtctctac acagtatata taataaccaa
agagcgtcct cttacgcttA TCTTAATTTC CCTCGCATTG AGAATTTTCA ACTTTTTCTA
TCTCTCTTCC CAAATCACAA ATGGCGGGTC GCGGCAAAAC TCTCGGATCT GGCGTTGCTA
AGAAATCAAC ATCGAGAAGC AGCAAAGCCG GTCTCCAATT CCCCGTTGGT CGTATCGCTC
GTTTTCTAAA GAACGGCAAG TACGCAACAC GTGTTGGTGC CGGAGCTCCG GTTTACTTAG
CCGCCGTTCT CGAATACCTC GCCGCTGAGg taattatccc cttctctccc tatatctctt
tactctttcg atcttcaatt tcgtaaaacc ctaatttcta aattggatct gttgtgttgt
agGTATTGGA ATTGGCTGGA AACGCAGCTA GGGATAACAA GAAGACTAGG ATTGTGCCAC
GTCACATTCA GCTCGCGGTG AGAAACGATG AGGAGCTGAG TAAACTGCTT GGAGATGTGA
CGATTGCTAA TGGAGGTGTG ATGCCTAACA TTCACAGTCT TCTTCTTCCC AAGAAAGCTG
GTGCTTCAAA ACCTTCCGCT GATGAAGATT AGATTAGGGA TTTGTGTTGT GGTTGTTTAG
CTAATTAATG TGTAGCTTAG TCTTTCATTA GATTAGATCT GAATTAGTTT TCATTAATGG
TGTTGTGTAG TCTCTCTTTT GCTTCAAAAA CAAGTATTAA AATCttatta ttttgaattg
aatccacaat caatacacat tgaagtccta acaaactact tcttcccagt gatatttgaa
accaaatcac taagaaactt agctgatttg gtaataggag aattcatagc catcaagtta
tacagaacaa gctcaacttc ttcgattgat ggtcgagaat tgaattgtga aacaactttc
aaagtaccat taccttcttc ttcttcaacg agaacattcc atctttctcc actcacaa
```

FIG. 8 (M)

A
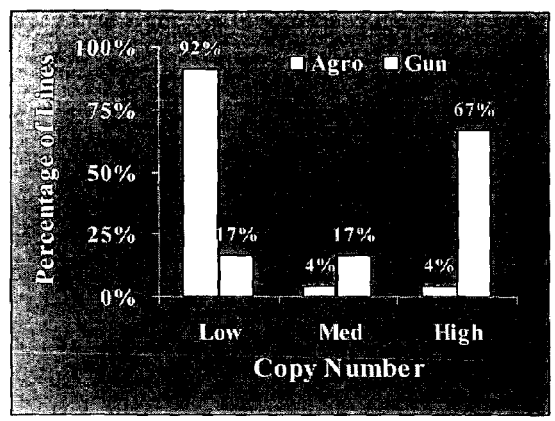
B
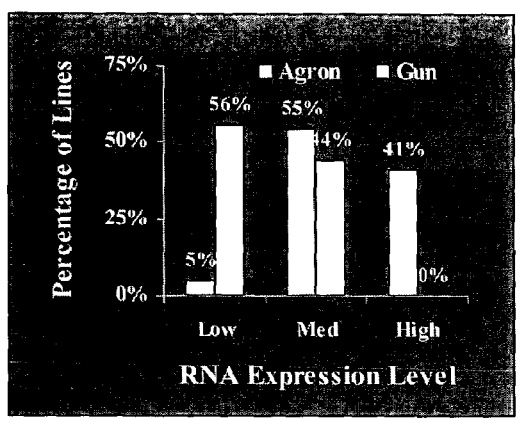
C
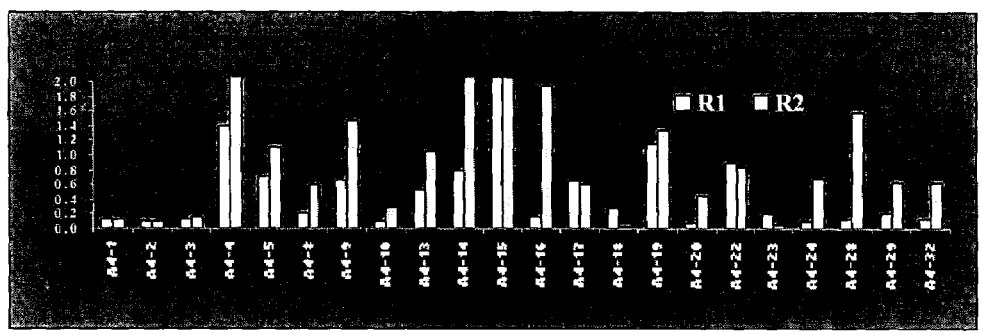
D
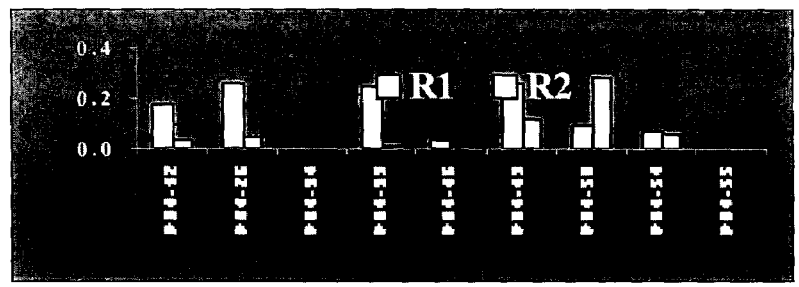
FIG. 9

METHODS AND COMPOSITIONS FOR ENHANCED PLANT CELL TRANSFORMATION

This application is a continuation-in-part of U.S. Ser. No. 10/098,161 filed Mar. 14, 2002 now U.S. Pat. No. 7,122,716, which claims priority from PCT/US00/25260, filed Sep. 14, 2000 and U.S. Ser. No. 60/154,158 filed Sep. 15, 1999 now abandoned. The United States Government may have some rights to the invention disclosed due to partial support from the National Science Foundation (NSF) Grant Nos: IBN-9630779 and DBI-0110023.

BACKGROUND OF THE INVENTION

The invention relates enhanced *Agrobacterium*-mediated transformation frequencies of plants due to addition of histones to the plant to be transformed. Methods specific for enhancing monocot transformation frequencies are also disclosed wherein both histones and L-cysteine are factors.

*Agrobacterium tumefaciens* is a gram negative soil bacterium that has been exploited by plant biologists to introduce foreign DNA into plants. The routine, efficient *Agrobacterium*-mediated transformation of dicotyledonous plants was first reported in the mid 1980's. Because monocotyledonous plants are not natural hosts for *Agrobacterium tumefaciens*, the development of transformation systems using this vector for monocots lagged that of dicots. Direct DNA delivery techniques including electroporation, microprojectile bombardment, and silicon carbide fiber treatment were developed for monocot transformation as alternatives to *Agrobacterium*-based DNA delivery. Production of fertile, transgenic maize plants was first reported in 1990 using microprojectile bombardment. Reports of fertile transgenic maize plant production using electroporation and silicon carbide fiber treatment followed a few years later.

The first well-documented report of fertile transgenic maize plants via *Agrobacterium* was published by Ishida et al. in 1996, followed by a second report from Negrotto et al. in 2000. Although high frequency *Agrobacterium*-mediated transformation was reported in those studies, and also in a few maize transformation labs in a private industry, those frequencies have not been reproduced in public maize transformation laboratories. Factors contributing to the lack of reproducibility in the public sector could include: 1) omission of critical details in protocol and media descriptions in published reports, 2) lack of access to specialized binary vectors by public researchers, and 3) reluctance or inability to transfer proprietary information from private industry to the public sector.

The significant advantages of using an *Agrobacterium*-based transformation system for maize (high frequency transformation, low copy, simple transgene insertion, increased stability of transgene expression, low cost relative to biolistics, and potential to introduce large DNA fragments into the plant genome) make it imperative that optimized protocols be developed, published, and made readily available to maize researchers in the public sector. Although known for this practical application, the actual mechanism of DNA transfer from bacteria to plants is not completely understood. Moreover, there are some limitations on the use of this transforming vector, e.g. difficulties in transforming monocots, and transforming frequencies may be too low to be useful. At present, even some dicots, for example, many *Arabidopsis* ecotypes and mutants also cannot be easily or efficiently transformed by a root transformation method, generally using *Agrobacterium*.

It is believed that *Agrobacterium tumefaciens* genetically transforms plant cells by transferring a portion of the bacterial Ti-plasmid, designated the T-DNA, to the plant, and integrating the T-DNA into the plant genome. Little is known about the T-DNA integration process, and no plant genes involved in integration have previously been identified. The DNA that is transferred from *Agrobacterium* to the plant cell is a segment of the Ti, or tumor inducing, plasmid called the T-DNA (transferred DNA). Virulence (vir) genes responsible for T-DNA processing and transfer are reported to lie elsewhere on the Ti plasmid. The role of vir genes in T-DNA processing, the formation of bacterial channels for export of T-DNA, and the attachment of bacteria to the plant cell are reported. In contrast, little is known about the role of plant factors in T-DNA transfer and integration.

Transformations can be transient or stable. Stable transformation is preferred because it is required to produce transgenic plants.

Many plant species are recalcitrant to stable *Agrobacterium* transformation. These species are, however, easily transiently transformed to express GUS activity or symptoms of viral infection following agroinoculation. Maize BMS cells are readily transiently transformed and could express and process a gus-A-intron transcript encoded by the binary vector pBISN1. Published results implied that, at least in this transformation system, T-DNA could target to maize nuclei and become converted to a double-stranded transcription-competent form. However, the lack of detectable stable transcription suggested that T-DNA integration may be deficient. Thus, making T-DNA integration more efficient and stabilizing T-DNA gene expression are important factors to improve maize transformation.

Integration of exogenous DNA is reported to be improved by delivering the DNA into plant cells with one or more *Agrobacterium* genes that can encode for proteins within the plant cells. This technique, referred to as "agrolistic transformation" is just an improvement over biolistic transformation by which DNA is delivered to the plants by a non-biological method such as a "gene gun" (biolistic transformation). In this improvement, genes encoding virulence proteins that normally function in *Agrobacterium* are transferred to the plants along with a T-DNA substrate. The substrate is then acted upon in the plant cell to make a T-DNA molecule. However, the technique described does not include the use of plant genes, or of other factors related herein. The technique was not shown to make a plant more susceptible to transformation. A goal of this method was to increase predictability of the location of integration, not its frequency. Moreover, "agrolistic transformation" is an expensive procedure requiring much infrastructure and resources; one of skill has to go through the laborious process every time to develop a transgenic plant.

The isolation of a putative plant factor has recently been reported. Ballas and Citovsky showed that a plant karyopherin α(AtKAP α) can interact with VirD2 nuclear localization sequences in a yeast two-hybrid interaction system, and is presumably involved in nuclear translocation of the T-complex. Using a similar approach, a tomato type 2C protein phosphatase, DIG3, that can interact with the VirD2 NLS was identified. Unlike AtKAP α, DIG3 plays a negative role in nuclear import. After the T-DNA/T-complex enters the nucleus, it must integrate into the plant chromosome. Plant chromosomal DNA is packaged into nucleosomes consisting primarily of histone proteins. The incoming T-DNA may have to interact with this nucleosome structure during the integration process. However, T-DNA may preferentially integrate into transcribed regions of the genome.

These regions are believed to be temporarily free of histones. How exactly T-DNA integration takes place is unknown. Recent reports have implicated involvement of VirD2 protein in the T-DNA integration process.

Several ecotypes of the dicot *Arabidopsis* are resistant to *Agrobacterium* transformation. Transforming the transformation resistant rat5 mutant of *Arabidopsis* with a wild-type RAT5 (histone H2A) gene was reported by the inventors to complement the mutant phenotype.

In monocots, maize is the most studied model plant that has important economic value. Although genetic transformation systems for the maize have been established in private laboratories, the lack of such systems is still a key limitation for public researchers. This is because most public research groups do not have access to the resources and infrastructure necessary for maize transformation by currently available procedures. In addition, the current technology has serious limitations, including low efficiency and throughput, difficulty with inbred line transformation, unpredictable transgene copy numbers and integrity, and undesirable transgene silencing during development and over generations.

Because fertile transgenic maize (*Zea mays*) was first produced using the biolistic gun, maize transformation technology has served as an important tool in germplasm development and research addressing fundamental biological questions through the study of transgenic maize. Recent reports have demonstrated that *Agrobacterium tumefaciens*-mediated maize transformation may offer a better alternative than the biolistic gun for delivery of transgenes to maize. This gene delivery system results in a greater proportion of stable, low-copy number transgenic events than does the biolistic gun, offers the possibility of transferring larger DNA segments into recipient cells, and is highly efficient. Reproducible protocols for *A. tumefaciens*-mediated maize transformation have used super binary vectors, in which the *A. tumefaciens* strain carries extra copies of virB, virC, and virG, to infect immature zygotic embryos of the inbred line A188 or the hybrid line Hi II. Hi II immature zygotic embryos were transformed by the inventor at an average efficiency of 5.8% using the *A. tumefaciens* super binary vector in strain LBA4404. Because the cost of licensing this proprietary technology for use on a broader scale may be prohibitive to a public sector laboratory, the inventors implemented an *A. tumefaciens* standard binary (non-super binary) vector system to transform maize Hi II immature zygotic embryos. Stable transformation of maize using a standard binary vector to infect shoot meristems was reported previously, but adoption of this method was hindered by its lack of robustness. Development of a reproducible and efficient method for transforming maize using a standard binary vector will not only provide researchers with the benefits already outlined, it would also facilitate vector construction when compared with the super binary vector. Final assembly of a super binary vector system involves co-integration of the gene of interest into a large plasmid (pSB1) in *A. tumefaciens* strain LBA4404 via homologous recombination. In contrast, assembly of a standard binary vector does not require this additional step, making it a more efficient way to confirm the introduction of a gene of interest into an *A. tumefaciens* strain.

Transformation of maize (*Zea mays*) using an *Agrobacterium tumefaciens* standard binary (non-super binary) vector system was achieved by the inventors. Immature zygotic embryos of the hybrid line Hi II were infected with *A. tumefaciens* strain EHA101 harboring a standard binary vector and cocultivated in the presence of 400 mg/L L-cysteine. Inclusion of L-cysteine in cocultivation medium led an improvement in transient-glucuronidase expression observed in targeted cells and a significant increase in stable transformation efficiency, but was associated with a decrease in embryo response after cocultivation. The average stable transformation efficiency (no. of bialaphos-resistant events recovered per 100 embryos infected) was 5.5%. Southern-blot and progeny analyses confirmed the integration, expression, and inheritance of the bar and gus transgenes in $R_0$, $R_1$, and $R_2$ generations of transgenic events. Fertile, stable transgenic maize was routinely produced using an *A. tumefaciens* standard binary vector system.

The level of stable transformation achieved is attributed to supplementation of cocultivation medium with 400 mg/L Cys. This antioxidant treatment also increased T-DNA delivery to embryogenic-competent scutellum cells of infected embryos. A similar increase in transient gus gene expression, followed by an increase in stable transformation efficiency, was reported in soybean cotyledonary node explants infected with *A. tumefaciens* and cocultivated on medium supplemented with Cys.

Contrary to expectations, the increase in stable transformation efficiency observed with the 400 mg/L Cys treatment was associated with a decrease in the proportion of embryos giving rise to embryogenic callus compared with the 0 mg/L Cys treatment. This reduction in embryo response is not related to the plant-pathogen interaction per se because noninfected embryos also exhibited reduced response on 400 mg/L Cys. It is likely that Cys concentrations as high as 400 mg/L are toxic to maize cells. A similar negative impact of 80 mg/L Cys on embryogenesis in Japonica rice explants was reported by Enriquez-Obregon et al. (1999). Comparable stable transformation rates were achieved using Cys concentrations as low as 100 mg/L, and this treatment was associated with better embryo recovery after cocultivation than that observed using the 400 mg/L Cys treatment.

*A. tumefaciens*-mediated maize transformation using a standard binary vector system is reproducible although variability in experimental efficiency persists. Using cocultivation medium within 7 d of preparation minimizes this variability. Average transformation efficiency is about 5.5%.

Information on plant factors and other factors affecting *Agrobacterium* transformation frequencies in plants is needed to improve performance of this method in both dicots and monocots.

SUMMARY OF THE INVENTION

Methods and compositions for increasing *Agrobacterium* transformation efficiency in a host plant include adding histones to the host plant and, for monocots, also adding L-cysteine and using a standard (a non-super, "Simple Binary Vector System") binary vector. Histones may be added either transiently or genes encoding histone may be stably incorporated into a host plant genome.

A polynucleotide sequence encoding a plant histone protein may be integrated into the host plant genome or just transiently introduced to express the polynucleotide sequence encoding a plant histone protein.

The host plant expressing the polynucleotide sequence encoding a plant histone protein to increase base levels of histone is transformed with a DNA molecule of interest by means of *Agrobacterium*.

There are four classes of core histones (H2A, H2B, H3 and H4). A suitable plant histone protein is a member of an H2A gene family of *Arabidopsis*, for example RAT5.

An aspect of the invention is a transgenic plant with at least one additional copy of a polynucleotide sequence encoding a plant histone H2A protein. The polynucleotide sequence may encode a plant histone H2A protein that is a member of an H2A gene family of *Arabidopsis*.

A method for increasing stable *Agrobacterium* transformation efficiency in host plants, includes the steps of:

(a) selecting a host plant expressing a polynucleotide sequence encoding a plant histone H2A protein, thereby increasing levels of histone in the host plant;

(b) introducing a transformation vector with a DNA molecule of interest into an *Agrobacterium* strain;

(c) providing at least one antioxidant in a cocultivation medium;

(d) infecting cells from the host plant with the *Agrobacterium* strain in the cocultivation medium;

(e) providing conditions suitable for recovery of infected cells; and (f) selecting the infected cells for transformants expressing the DNA molecule of interest.

The host plant may be a monocot, for example, maize.

The antioxidant may be L-cysteine.

The L-cysteine concentration may be between about 100 mg/L and 400 mg/L.

Infection of cells in the cocultivation medium may be for 3 days.

An aspect of the invention is a genetic construct comprising at least one copy of a histone gene in addition to that in the host plant initially that when expressed is capable of increasing transformation frequencies in a host plant.

The histone gene may encode H2A, for example a RAT5 *Arabidopsis* gene.

An aspect of the invention is a host cell transformed by at least one copy of a gene involved in T-cell integration wherein the gene is capable of effecting overexpression of histone to enhance plant transformation frequencies.

A method for increasing *Agrobacterium* transformation frequencies in a host plant, includes the steps of:

a. increasing histone levels in the host plant compared to normal levels of histone in the host plant; and b. transforming the host plant with *Agrobacterium*.

Transformation frequencies may be measured by the number of tumors produced in the host plant or by using markers detectable if transformation has occurred.

The H2A histone may be H2A-1.

An aspect of the invention is a plant cell with an overexpression of plant histones sufficient to increase efficiency of transformation of the plant cell by *Agrobacterium*.

Definitions

Transformation efficiency: (no. of successful events/no. of embryos infected) X 100. The number of transgenic events is a indication of stable transformation. The transformation efficiency calculation may also involve inflorescences, callus, seeds or other biological material that can be infected with *Agrobacterium* to produce a transformant.

H2A: A member of H2A gene family. The H2A gene members are also denoted by HTA. *Arabidopsis* RAT5 is one such member of H2A/HTA gene family.

Retransformation: transformation of a plant that has at least one additional copy of a polynucleotide encoding histone H2A protein stably integrated into the host plant genome.

Infected: *Agrobacterium* is in the host cell.

BRIEF DESCRIPTION OF THE DRAWINGS

FIG. 6(A-E) shows the cDNA sequences of HTA1 through HTA13 (SEQ ID NOS: 2-14, respectively, in order of appearance). The coding region is highlighted in bold font and 5' and 3' UTR region in normal font.

FIG. 7(A-B) shows the amino acid sequences of HTA1 through HTA13 (SEQ ID NOS: 15-27, respectively, in order of appearance).

FIG. 8(A-M) shows the genomic sequences of HTA1 through HTA13 (SEQ ID NOS: 28-40, respectively, in order of appearance).

FIG. 9 shows that *Agrobacterium*-mediated transformation results in lower transgene copy number (A) and higher gene expression (B) compared with biolistic gun transformation of maize (Copy number: L: 1-3; M: 4-10; H: 10-20; VH: >20). (C-D) show that transgene expression is more stable in *Agrobacterium*-derived transformants (C) than in bombardment-derived ones (D).

DETAILED DESCRIPTION OF THE INVENTION

Figure 1A:
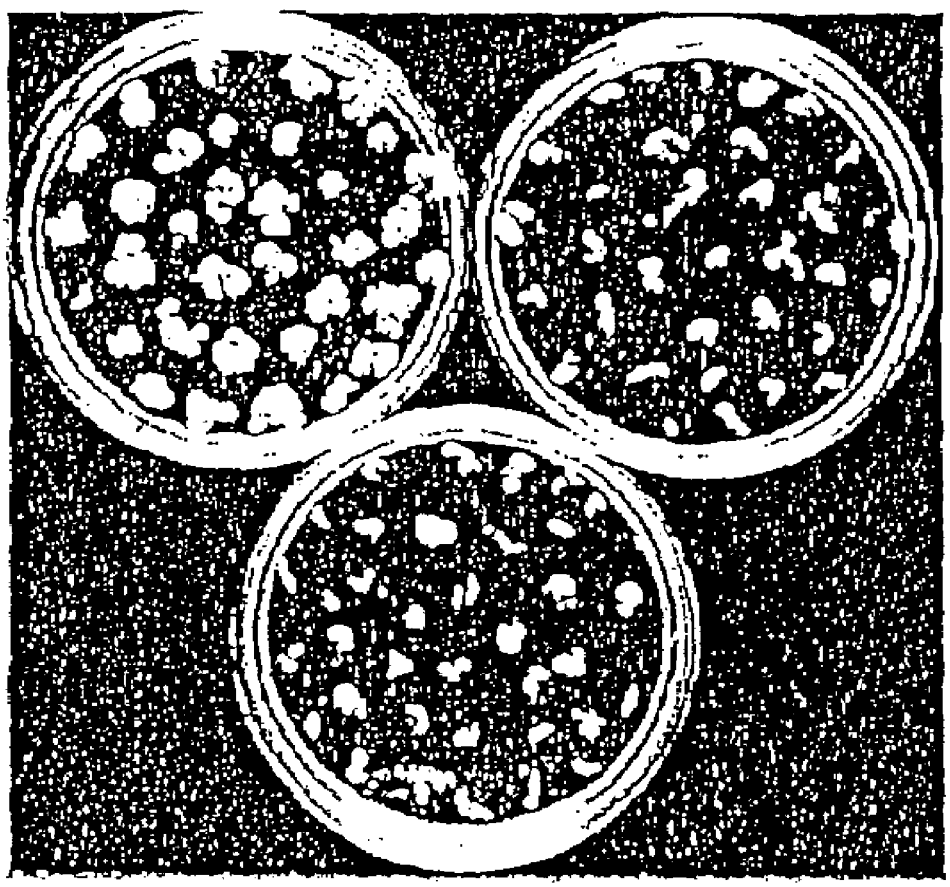
FIG. 1 shows characteristics of the rat5 mutant: (A) stable transformation of wild-type *Arabidopsis* ecotype Ws, the rat5 mutant, and the F1 progeny; (B) sequence of the rat5/T-DNA junction region (SEQ ID NO: 1); (C) pattern of T-DNA integration in rat5: LB, T-DNA left border; RB, T-DNA right border; pBR322, pBR322 sequences containing the β-lactamase gene and ColE1 origin of replication; Tn903, kanamycin resistance gene for *E. coil* selection; Tn5, kanamycin resistance gene for plant selection.

The invention relates to methods and composition to increase *Agrobacterium* transformation frequencies in plants due to addition of histones directly or by incorporating into the host plant at least one plant gene involved in host T-DNA integration. This differs from some methods in prior publications because plant host genes, not bacterial *Agrobacte-*

*rium* genes, are used to enhance transformation. In an embodiment, addition of at least one histone H2A gene encoded by the *Arabidopsis* RAT5 gene enhances transformation frequencies, most likely due to overexpressing of histone as compared to the host's natural expression levels. The gene can be either in transgenic plants or carried by the transforming agent, T-DNA, for practice of the invention.

To identify plant genes involved in *Agrobacterium*-mediated transformation, a T-DNA tagged *Arabidopsis* library was screened for mutants that are resistant to *Agrobacterium* transformation (rat mutants). An *Arabidopsis* T-DNA tagged mutant, rat5, was characterized that is deficient in T-DNA integration and is resistant to *Agrobacterium*-mediated root transformation. Both genetic and DNA blot analyses indicated that there are two copies of T-DNA integrated as a tandem repeat at a single locus in rat5. No major rearrangements are in the rat5 plant DNA immediately surrounding the T-DNA insertion site. These data strongly suggest that in rat5 the T-DNA had inserted into a gene necessary for *Agrobacterium*-mediated transformation. The sequence of the T-DNA left border-plant junction indicated that the T-DNA had inserted into the 3' untranslated region of a histone H2A gene. This insertion is upstream of the consensus polyadenylation signal. By screening an *Arabidopsis* ecotype Ws cDNA library and sequencing 20 different histone H2A cDNA clones, and by performing a computer data base search, at least six different histone H2A genes were identified. These genes encode proteins that are greater than 90% identical at the amino acid sequence level. Thus, the histone H2A genes comprise a multi-gene family in *Arabidopsis*.

The gene bank accession number AB016879 contains a report of a DNA sequence of some of the clones derived from *Arabidopsis thaliana* chromosome 5. One of these sequences is a histone H2A gene that is identical to the RAT5 gene. However, this report neither teaches nor suggests a role for histone in improving transformation frequencies.

Overexpression of histone genes of the present invention overcomes the poor performance that limits the use of *Agrobacterium* as a transforming vector. Many plants can be transformed transiently by *Agrobacterium* so they express the transforming gene for a period of time, but are not stably transformed because of T-DNA integration problems. Therefore, transgenic plants are not produced. The gene H2A (RAT5) plays an important role in illegitimate recombination of T-DNA into the plant genome and the gene's overexpression enhances transformation.

Transient and stable GUS (β-glucuronidase) expression data and the assessment of the amount of T-DNA integrated into the genomes of wild-type and rat5 *Arabidopsis* plants indicated that the rat5 mutant is deficient in T-DNA integration needed for transformation. Complementing the rat5 mutation was accomplished by expressing the wild-type RAT5 histone H2A gene in the mutant plant. Surprisingly, overexpression of RAT5 in wild-type plants increased *Agrobacterium* transformation efficiency. Furthermore, transient expression of a RAT5 gene from the incoming T-DNA was sufficient to complement the rat5 mutant and to increase the transformation efficiency of wild-type *Arabidopsis* plants. Adding histone directly to the host plant enhances transformation. The present invention provides methods and compositions to increase stable transformation frequency in plants using direct involvement of a plant histone gene in T-DNA integration.

Several T-DNA tagged mutants of *Arabidopsis* were identified that are recalcitrant to *Agrobacterium* root transformation. These are called rat mutants (resistant to *Agrobacterium* transformation). In most of these mutants *Agrobacterium* transformation is blocked at an early step, either during bacterial attachment to the plant cell or prior to T-DNA nuclear import. In some of the mutants, however, the T-DNA integration step is most likely blocked. Because plant factors involved in illegitimate recombination of T-DNA into the plant genome have not previously been identified, the characterization of a T-DNA tagged *Arabidopsis* mutant, rat5, that is deficient in T-DNA integration, is an aspect of the present invention.

Characterization of the rat5 mutant. rat5, an *Arabidopsis* T-DNA tagged mutant, was previously identified as resistant to *Agrobacterium* root transformation. rat5 mutants are also expected in other species, e.g. maize. An in vitro root inoculation assay was performed using the wild-type *Agrobacterium* strain A208 (At10). After one month, the percentage of root bundles that formed tumors was calculated. Greater than 90% of the root bundles of the wild-type plants (ecotype Ws) formed large green teratomas. In contrast, fewer than 10% of the root bundles from the rat5 plants responded to infection, forming small yellow calli (FIG. 1A). A homozygous rat5 plant (pollen donor) was crossed to a wild-type plant (egg donor) and the resulting F1 progeny tested for susceptibility to *Agrobacterium* transformation. This analysis indicated that rat5 is a dominant mutation (FIG. 1A). Further analysis of F2 progeny indicated that kanamycin resistance segregated 3:1, indicating that a single locus had been disrupted by the mutagenizing T-DNA. Kanamycin resistance co-segregated with the rat5 phenotype, indicating that a gene involved in *Agrobacterium* transformation had most likely been mutated by the T-DNA insertion.

Figure 1C:
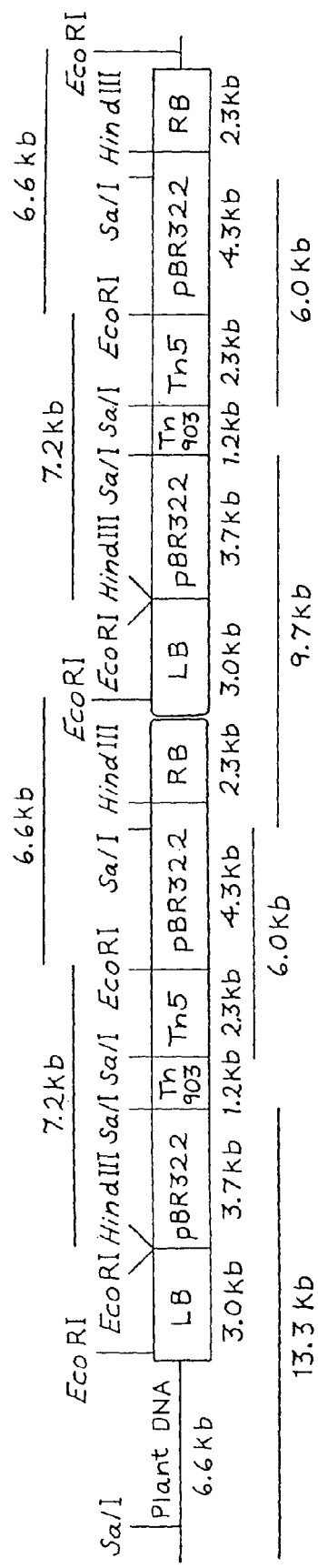

Recovery of a T-DNA-plant junction from rat5. The T-DNA integration pattern in the rat5 mutant was determined by DNA blot analyses. The results indicated that there are only two copies of the mutagenizing T-DNA integrated into the genome of the rat5 mutant. Further analysis indicated that these two T-DNA copies are present as a direct tandem repeat, as shown in FIG. 1C.

A left border (LB) T-DNA-plant junction was recovered from rat5 using a plasmid rescue technique (see Materials and Methods) and a restriction endonuclease map of this T-DNA-plant junction was constructed. An approximately 1.7 kbp EcoRI fragment that contains both plant and LB DNA was subcloned into pBluescript and subsequently sequenced at the Purdue University sequencing center. The sequence of this fragment is shown in FIG. 1B. DNA sequence analysis of this junction region indicated that the T-DNA had inserted into the 3' untranslated region (UTR) of a histone H2A gene (FIG. 1B). The histone H2A genes of *Arabidopsis* were further characterized by isolating and sequencing numerous cDNA and genomic clones. Six different gene variants of histone H2A were identified, indicating that the histone H2A genes of *Arabidopsis* comprise a small multi-gene family. In a lambda genomic DNA library a clone was identified containing the wild-type histone H2A gene corresponding to RAT5. DNA sequence analysis of this genomic clone indicated that in rat5 the T-DNA had inserted upstream of the consensus polyadenylation signal (AATAA). DNA blot analysis of Ws and rat5 DNA indicated that the T-DNA insertion in rat5 did not cause any major rearrangements in the plant DNA immediately around the site of insertion. Disruption of the 3' UTR of the RAT5 histone H2A gene is likely the sole cause for the rat phenotype in the rat5 mutant.

FIG. 1 shows characterization of the rat5 mutant. (A) Stable transformation of wild-type *Arabidopsis* ecotype Ws, the rat5 mutant, and the F1 progeny. Sterile root segments were infected with *A. tumefaciens* A208. Two days after cocultivation, the roots were transferred to MS medium lacking phytohormones and containing timentin as an antibiotic. Tumors were scored after four weeks. (B) Sequence of the rat5/T-DNA junction region. (C) Pattern of T-DNA integration in rat5. LB, T-DNA left border; RB, T-DNA right border; pBR322, pBR322 sequences containing the β-lactamase gene and ColE1 origin of replication; Tn903, kanamycin resistance gene for *E. coli* selection; Tn5, kanamycin resistance gene for plant selection. Five μg of genomic DNA from the rat5 mutant was digested with either EcoRI or SalI and was blotted onto a nylon membrane. An EcoRI-SalI fragment of pBR322 was used as the hybridization probe. Restriction fragment sizes shown above the T-DNA were detected by EcoRI digestion and the sizes shown below the T-DNA were detected by SalI digestion.

Figure 2A:
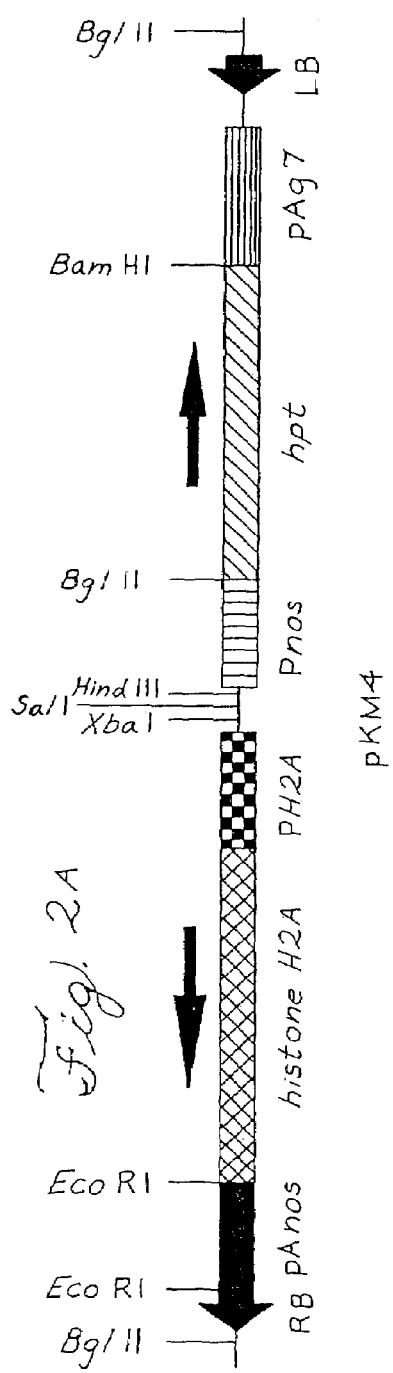
FIG. 2 shows complementation of the rat5 mutant and overexpression of RAT5 in wild-type *Arabidopsis* plants; (A) maps of the binary vectors pKM4 and (B) pKM5 RB, T-DNA right border; LB, T-DNA left border; pAnos, nopaline synthase polyadenylation signal sequence; histone H2A, coding sequence of the RAT5 histone H2A gene; pH2A, promoter sequence of the RAT5 histone H2A gene; Pnos, nopaline synthase promoter; hpt, hygromycin resistance gene; pAg7, agropine synthase polyadenylation signal sequence; uidA, promoterless gusA gene; arrows above the histone H2A, uidA, and hpt genes indicate the direction of transcription; (C) complementation of the rat5 mutant; (D) tumorigenesis assay of Ws transgenic plants overexpressing the RAT5 histone H2A gene.
Figure 2B:
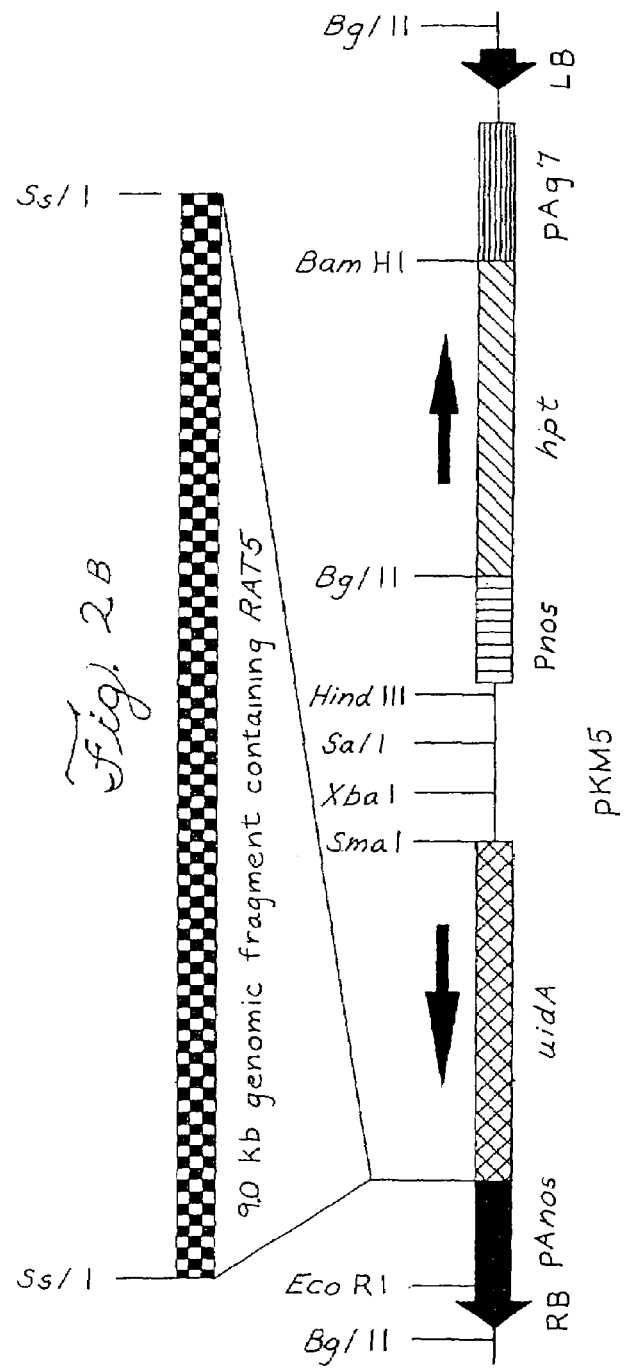

Complementation of the rat5 mutant with a wild-type histone H2A gene (RAT5). Two different constructions were made to perform a complementation analysis of the rat5 mutant. First, a nopaline synthase terminator (3' NOS) was fused to the 3' region of the 1.7 kbp junction fragment (the sequence of this 1.7 kbp fragment is shown in FIG. 1B). This construction contains the RAT5 histone H2A gene with its own promoter and a 3' NOS. This fragment (RAT5 plus 3' NOS) was cloned into the binary vector pGTV-HPT of beaker containing a hygromycin resistance gene between the left and the right T-DNA borders, resulting in the binary vector pKM4 (FIG. 2A). For the second construction, a 9.0 kbp SacI genomic fragment of wild-type Ws DNA containing a histone H2A gene (RAT5) plus at least 2.0 kbp sequences upstream and downstream of RAT5 was cloned into the binary vector pGTV-HPT, resulting in the binary vector pKM5 (FIG. 2B). pKM4 and pKM5 were transferred separately into the non-tumorigenic *Agrobacterium* strain GV3101, resulting in strains *A. tumefaciens* At1012 and At1062, respectively.

Figure 2C:
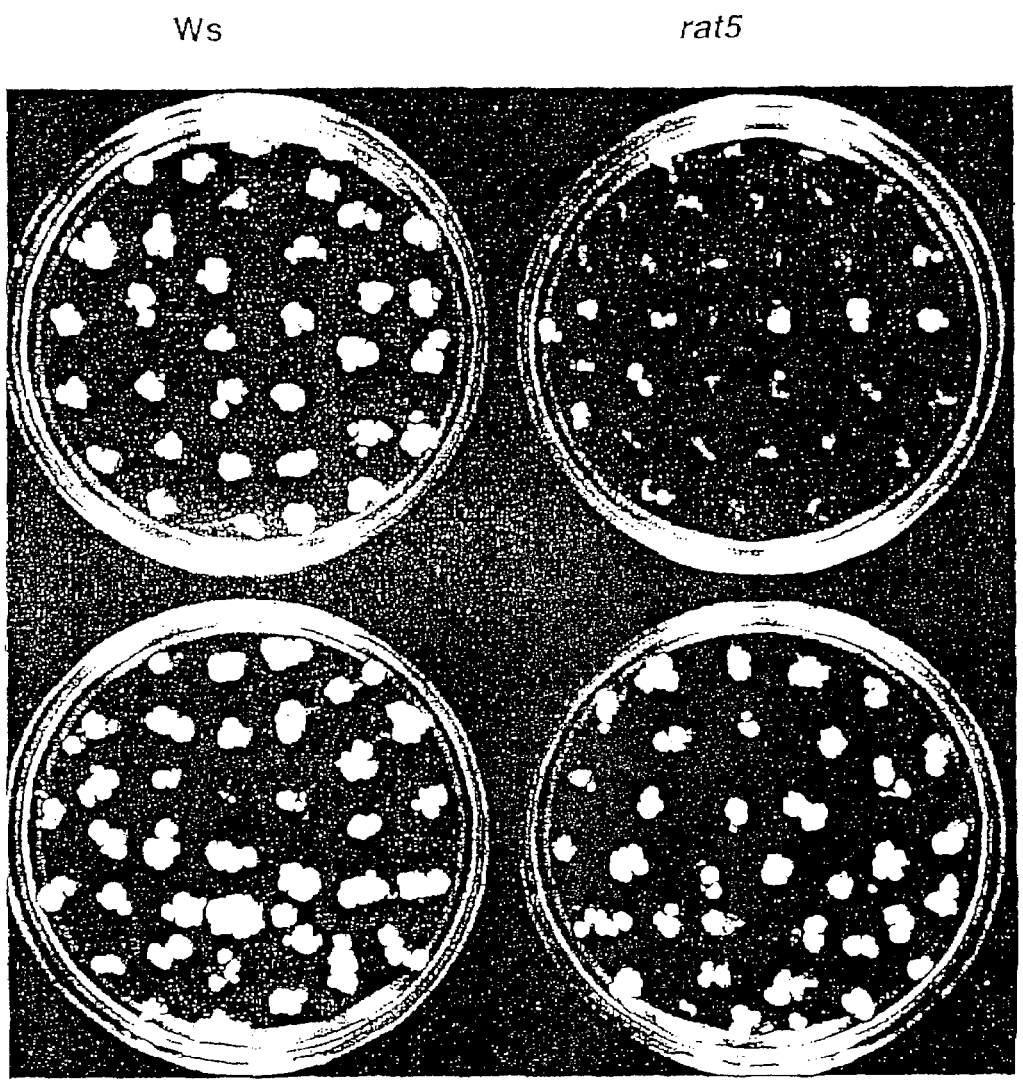

Both strains At1012 and At1062 were separately used to transform rat5 plants using a germ-line transformation method (Bent et al., 1998) and transgenic rat5 plants were selected for resistance to hygromicin (20 μg/ml). Several transgenic plants (T1) were obtained. These transgenic plants were allowed to self fertilize and T1 seeds were collected. Six transgenic lines obtained by transformation with At1012 (the wild-type histone H2A with 3' NOS) were randomly selected and their seeds were germinated in the presence of hygromycin. Tumorigenesis assays were performed as described in Nam et al. (1999) using *A. tumefaciens* At10 and a sterile root inoculation protocol, on at least five different plants from each of the six transgenic lines. The results indicated that in five of the six transgenic rat5 lines tested, the tumorigenesis-susceptibility phenotype was recovered (FIG. 2C; Table 1). Teratomas incited on the roots of these plants appeared similar to tumors generated on a wild-type plant. One of the transgenic plants tested did not recover the tumorigenesis-susceptibility phenotype, probably because of an inactive transgene. Transgenic T1 plants of rat5 obtained by transformation with At1062 (containing a genomic encoding RAT5 from the wild-type plant) were also tested for restoration of the tumorigenesis-susceptibility phenotype. Some of these plants were also able to recover the tumorigenesis-susceptibility phenotype, indicating complementation of the rat5 mutation. Hygromycin-resistant transgenic plants generated by transforming the rat5 mutant with pGPTV-HPT alone did not form tumors upon infection with *A. tumefaciens* A208.

To confirm the genetic basis of the complementation experiment, a co-segregation analysis was performed on one of the rat5 transgenic lines (rat5 At1012-6) obtained by transformation of the rat5 mutant with *A. tumefaciens* At1012. To examine the co-segregation of the complementing T-DNA containing the wild-type RAT5 gene with the tumorigenesis-susceptibility phenotype, seeds from a T2 plant homozygous for the rat5 mutation but heterozygous for hygromycin resistance were germinated and grown on B5 medium without selection. Roots of these plants were subsequently tested for hygromycin-resistance and susceptibility to crown gall tumorigenesis. All plants that were sensitive to hygromycin were also resistant to tumor formation in a manner similar to that of the rat5 mutant. Of the 25 hygromycin-resistant plants, at least 8 were susceptible to tumorigenesis. However, 17 hygromycin-resistant plants remained recalcitrant to *Agrobacterium*-mediated transformation. It is likely that these plants are heterozygous with respect to the complementing RAT5 gene and did not express this gene to a level high enough to restore susceptibility to tumorigenesis. This possibility corresponds to the finding that the rat5 mutation is dominant, and that therefore one active copy of RAT5 is not sufficient to permit *Agrobacterium*-mediated transformation. Taken together, the molecular and genetic data strongly indicate that in the rat5 mutant disruption of a histone H2A gene is responsible for the tumorigenesis-deficiency (rat) phenotype.

Figure 2D:
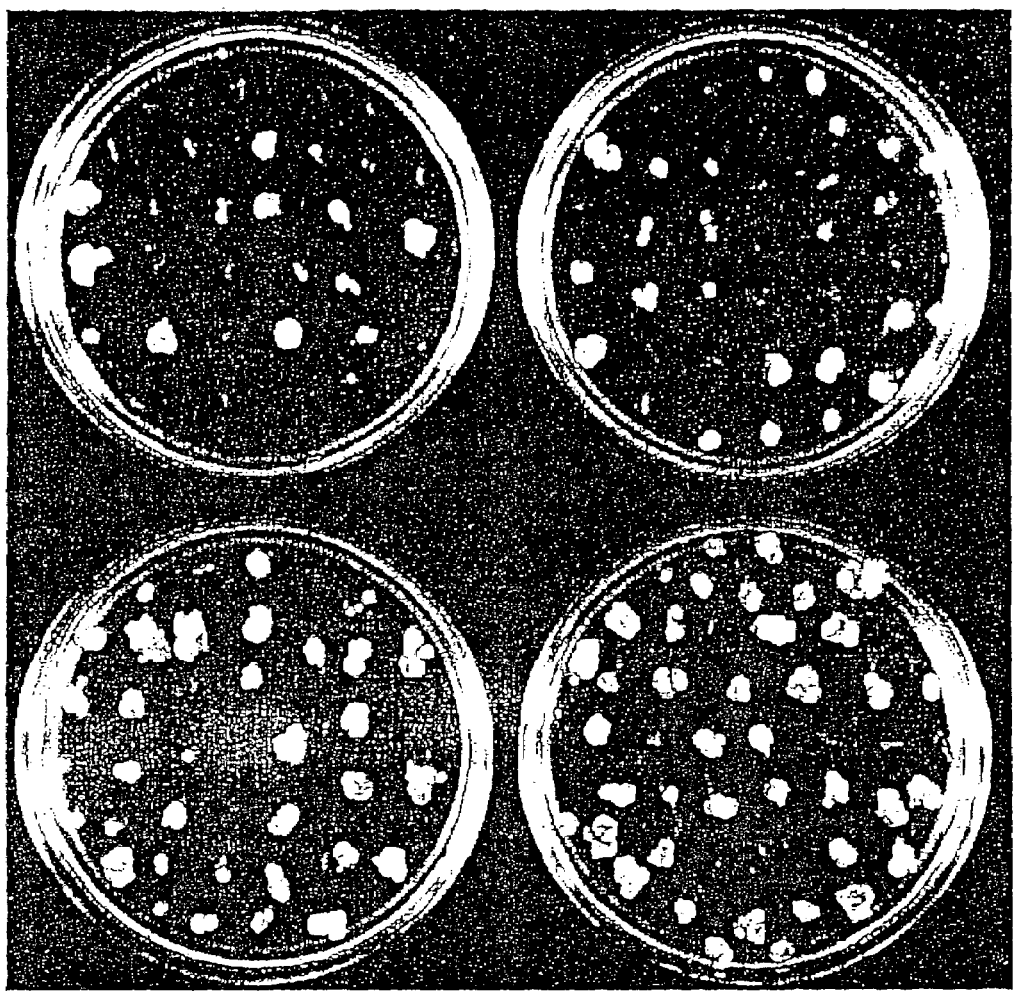

Overexpression of a histone H2A (RAT5) gene in wild-type plants improves the efficiency of *Agrobacterium* transformation. To determine further whether the RAT5 gene plays a direct role in *Agrobacterium*-mediated transformation, *A. tumefaciens* At 1012 was used to generate several transgenic *Arabidopsis* plants (ecotype Ws) containing additional copies of the RAT5 histone H2A gene. These transgenic plants were allowed to self-pollinate, T1 seeds were collected, and T2 plants were germinated in the presence of hygromycin. Tumorigenesis assays were performed as described herein at least five plants from each of four different transgenic lines. Because ecotype Ws normally is highly susceptible to *Agrobacterium* transformation, the tumorigenesis assay was altered to detect any subtle differences between the transformation-susceptible wild-type plant and transgenic wild-type plants overexpressing RAT5. These alterations included inoculation of root segments with a 100-fold lower concentration ($2 \times 10^7$ cfu/ml) of bacteria than that normally used ($2 \times 10^9$ cfu/ml), and spreading individual root segments rather than bundles of root segments on MS medium to observe tumor production. The results, shown in Table 1 and FIG. 2D, indicate that transgenic plants overexpressing RAT5 are approximately twice as susceptible to root transformation as are wild-type Ws plants. These data indicate that the RAT5 histone H2A gene plays a direct role in T-DNA transformation, and that overexpression of RAT5 can increase susceptibility to transformation.

Transient expression of histone H2A is sufficient to permit transformation of rat5 and to increase the transformation efficiency of wild-type Ws plants. Expression of the RAT5 histone H2A gene from the incoming T-DNA complement the rat5 mutant. Although transformation of this mutant with an *Agrobacterium* strain harboring pGPTV-HYG (lacking a histone H2A gene) resulted in only a few, slow-growing calli on hygromycin selection medium, *Agrobacterium* strains harboring pKM4 or pKM5 incited rapidly growing hygromycin-resistant calli on 60±21% and 54±22% of the rat5 root segment bundles, respectively. In addition, when wild-type plants were infected (at low bacterial density) with a tumorigenic *Agrobacterium* strain (A208) harboring pKM4, 78±8% of the root segments developed tumors, compared to 36±9% of the root segments infected with a tumorigenic bacterial strain harboring pGPTV-HYG. These transformation experiments indicate that *Agrobacterium* strains containing the binary vectors pKM4 or pKM5 are able to transform rat5 mutant plants at relatively high efficiency, and on wild-type plants are two-fold more tumorigenic, and are better able to incite hygromycin-resistant calli, than are *Agrobacterium* strains containing the "empty" binary vector pGPTV-HYG. Transiently produced histone H2A improves the stable transformation efficiency of plants by *Agrobacterium*.

Figure 3A:
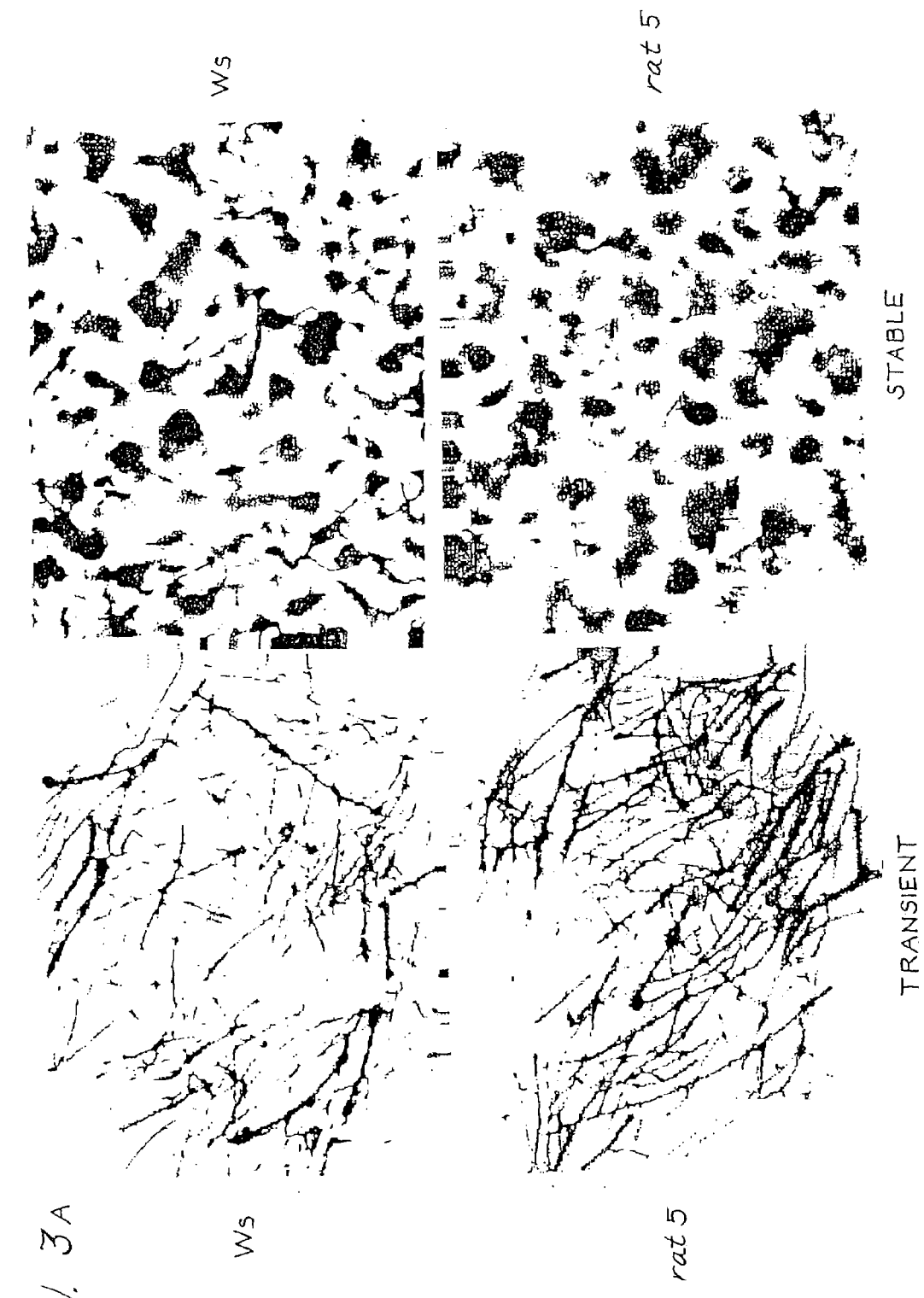
FIG. 3 shows T-DNA integration assays of rat5 and Ws plants; (A) transient and stable GUS expression in Ws and RAT5; (B) T-DNA integration in rat5 and Ws plants.

The rat5 mutant is deficient in T-DNA integration. *Agrobacterium*-mediated transformation of the *Arabidopsis* rat5 mutant results in a high efficiency of transient transformation but a low efficiency of stable transformation, as determined by the expression of a gusA gene encoded by the T-DNA. This result suggested that rat5 is most likely deficient in T-DNA integration. To test this hypothesis directly root segments from Ws and rat5 plants were inoculated with *A. tumefaciens* GV3101 harboring the T-DNA binary vector pBISN1. pBISN1 contains a gusA-intron gene under the control of a "super-promoter" (Ni et al., 1995; Narasimhulu et al., 1996). Two days after cocultivation, the root segments were transferred to callus inducing medium containing timentin (100 µg/ml) to kill the bacteria. Three days after infection, a few segments were stained for GUS activity using the chromogenic dye X-gluc. Both the wild-type and the rat5 mutant showed high levels of GUS expression (approximately 90% of the root segments stained blue; FIG. 3A). The remaining root segments were allowed to form calli on callus inducing medium containing timentin to kill *Agrobacterium*, but lacking any antibiotic for selection of plant transformation. After four weeks numerous calli derived from at least five different Ws and rat5 plants were stained with X-gluc. Of the Ws calli sampled, 92±12% showed large blue staining areas, whereas only 26±10% of the rat5 calli showed GUS activity, and most of these blue staining regions were small (FIG. 3A). These data indicate that although the rat5 mutant can transiently express the gusA gene at high levels, it fails to stabilize gusA expression.

Figure 3B:
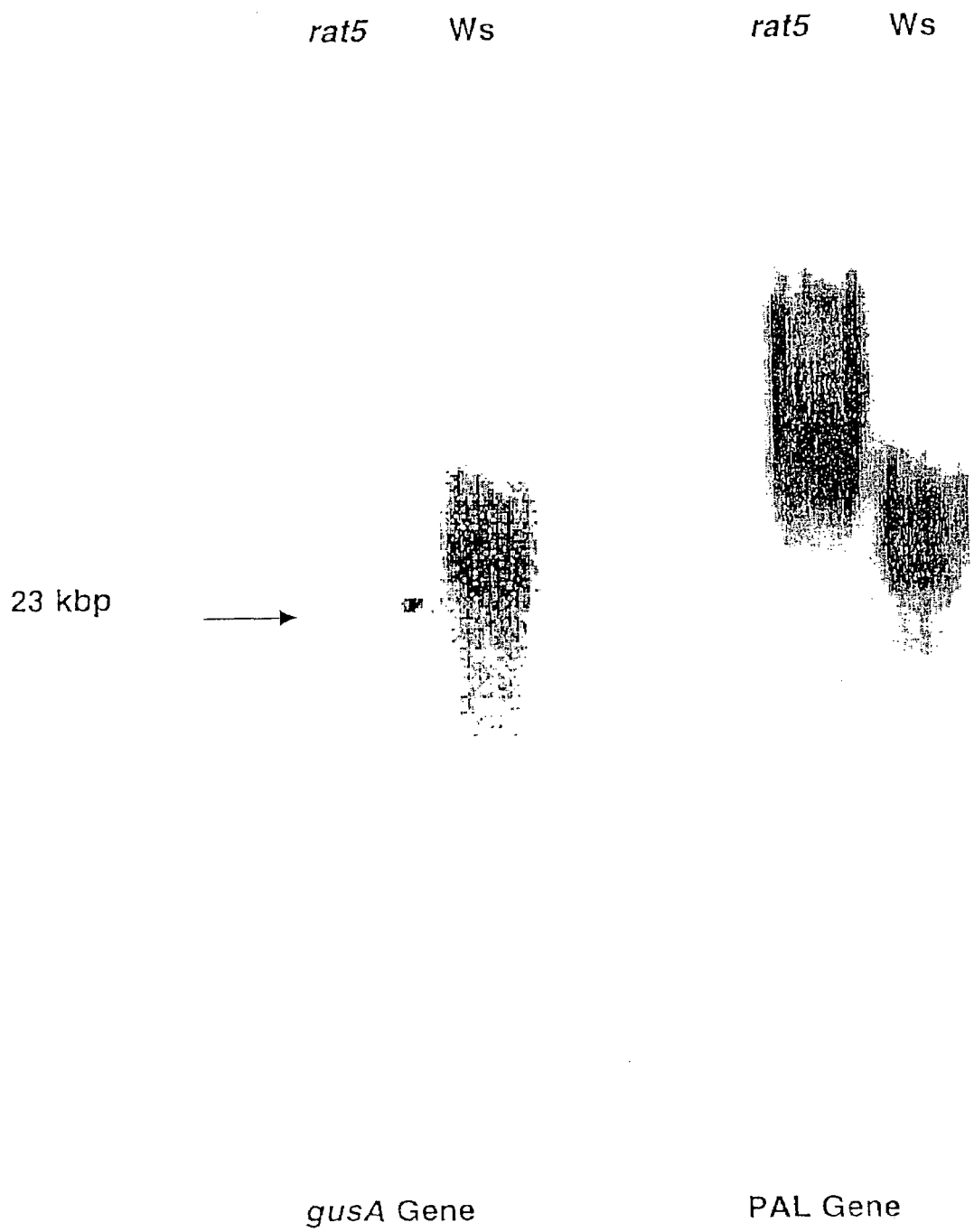
Figure 4:
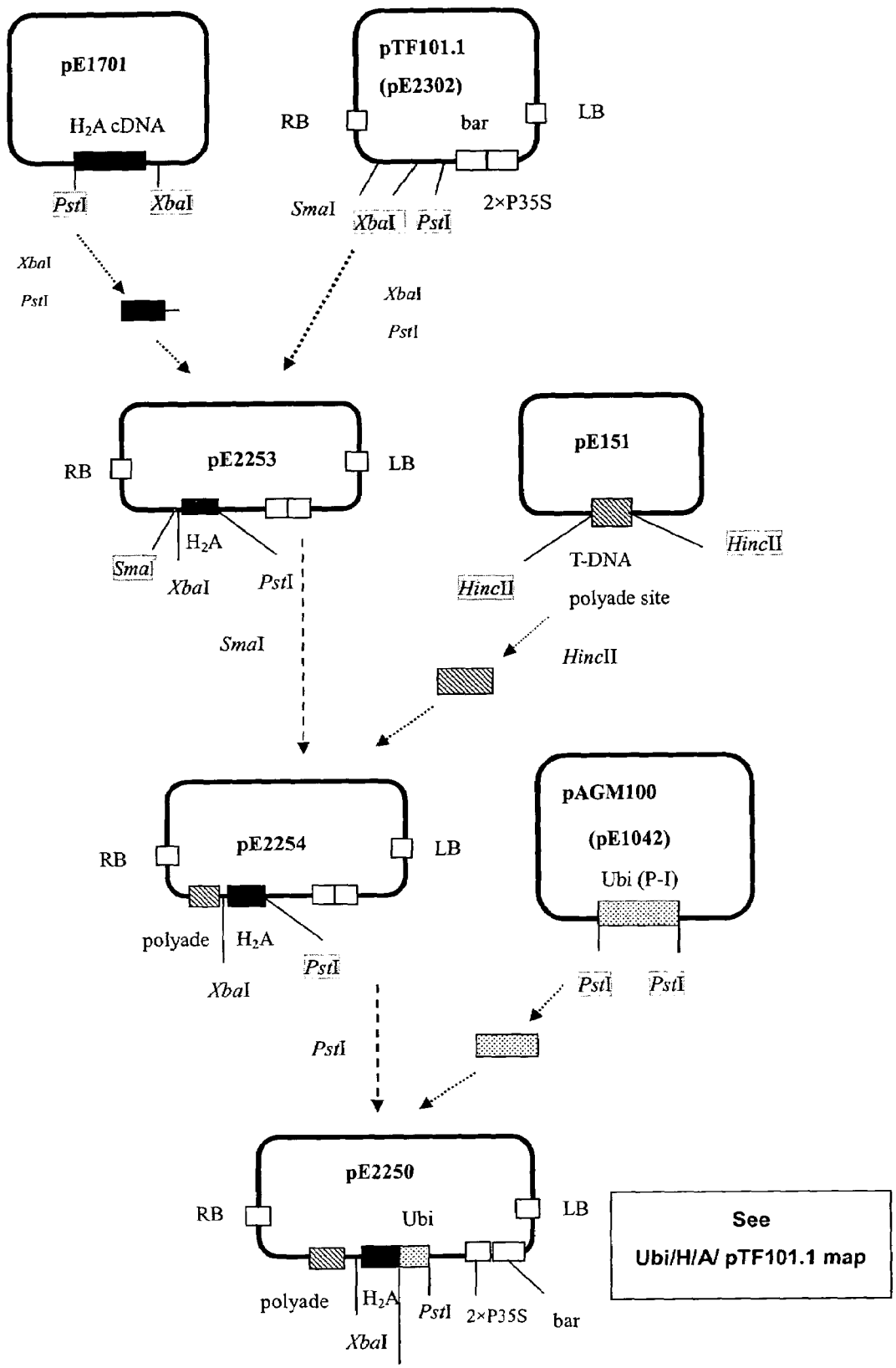
FIG. 4 shows the map of the binary maize transformation vector pE2250 to generate the founder lines of maize and a flow chart of the construction of the vector.

Suspension cell lines were generated from these Ws and rat5 calli and after an additional month the amount of T-DNA was assayed (using as a hybridization probe the gusA-intron gene located within the T-DNA of pBISN1) integrated into high molecular weight plant DNA from Ws and rat5 calli (Nam et al., 1997; Mysore et al., 1998). FIG. 3B shows that although T-DNA integrated into the genome of wild-type Ws plants was easily detectable, T-DNA integrated into the rat5 genome was not. These data directly demonstrate that rat5 is deficient in T-DNA integration. To demonstrate equal loading of plant DNA in each of the lanes, the gusA probe was stripped from the blot and rehybridized the blot with an *Arabidopsis* phenylalanine ammonia-lyase (PAL) gene probe.

FIG. 2 shows complementation of the rat5 mutant and overexpression of RAT5 in wild-type *Arabidopsis* plants. Maps of the binary vectors pKM4 (A) and pKM5 (B). RB, T-DNA right border; LB, T-DNA left border; pAnos, nopaline synthase polyadenylation signal sequence; histone H2A, coding sequence of the RAT5 histone H2A gene; pH2A, promoter sequence of the RAT5 histone H2A gene; Pnos, nopaline synthase promoter; hpt, hygromycin resistance gene; pAg7, agropine synthase polyadenylation signal sequence; uidA, promoterless gusA gene. Arrows above the histone H2A, uidA, and hpt genes indicate the direction of transcription. (C) Complementation of the rat5 mutant. rat5 mutant plants were transformed with an *Agrobacterium* strain containing the binary vector pKM4 (At1012). Hygromycin-resistant resistant transgenic plants were obtained and were self-pollinated to obtain T2 plants. Sterile root segments of T2 plants expressing RAT5, wild-type Ws plants, and rat5 mutant plants were infected with the tumorigenic strain *A. tumefaciens* A208. Two days after cocultivation, the roots were moved to MS medium lacking phytohormones and containing timentin. Tumors were scored after four weeks. (D) Tumorigenesis assay of Ws transgenic plants overexpressing the RAT5 histone H2A gene. Ws plants were transformed with *A. tumefaciens* At1012 containing the binary vector pKM4. Hygromycin-resistant transgenic plants were obtained and were self-pollinated to obtain T2 plants. Sterile root segments of T2 plants overexpressing RAT5 and wild-type Ws plants were infected at low bacterial density with *A. tumefaciens* A208. After two days cocultivation, the roots were moved to MS medium lacking phytohormones and containing timentin. Tumors were scored after four weeks.

Teratomas incited on the roots of these plants appeared similar to tumors generated on a wild-type plant. One of the transgenic plants tested did not recover the tumorigenesis-susceptibility phenotype, probably because of an inactive transgene. Transgenic T1 plants of rat5 obtained by transformation with At1062 (containing a genomic encoding RAT5 from the wild-type plant) were also tested for restoration of the tumorigenesis-susceptibility phenotype. Some of these plants were also able to recover the tumorigenesis-susceptibility phenotype, indicating complementation of the rat5 mutation. Hygromycin-resistant transgenic plants generated by transforming the rat5 mutant with pGPTV-HPT alone did not form tumors upon infection with *A. tumefaciens* A208.

FIG. 3 shows T-DNA integration assays of rat5 and Ws plants; (A) transient and stable GUS expression in Ws and rat5; Sterile root segments of Ws and rat5 plants were infected with the non-tumorigenic *Agrobacterium* strain GV3101 containing the binary vector pBISN1. Two days after cocultivation, the roots were transferred to callus inducing medium (CIM) containing timentin. Three days after infection, half of the segments were stained with X-gluc to determine the efficiency of transient GUS expression. The other group of segments was allowed to form calli on CIM. After four weeks these calli were stained with X-gluc to determine the efficiency of stable GUS expression. (B) T-DNA integration in rat5 and Ws plants. Suspension cells were derived from the calli generated from Ws and rat5 root segments infected with the non-tumorigenic *Agrobacterium* strain GV3101 containing the binary vector pBISN1. The suspension cell lines were grown for three weeks (without selection for transformation) in the presence of timentin or cefotaxime to kill *Agrobacterium*. Genomic DNA was isolated from these cells, subjected to electrophoresis through a 0.6% agarose gel, blotted onto a nylon membrane, and hybridized with a gusA gene probe. After autoradiography, the membrane was stripped and rehybridized with a phenylalanine ammonia-lyase (PAL) gene probe to determine equal loading of DNA in each lane.

TABLE 1

Complementation of the rat5 mutant and overexpression of RAT5 in wild-type (Ws) Arabidopsis plants

| Line | % Root Bundles With Tumors | Tumor Morphology |
|---|---|---|
| rat5 complementation with At1012 (T2 plants)[a] | | |
| Ws | 98 ± 2 | large, green |
| rat5 | 21 ± 6 | small, yellow |
| rat5 At1012-1 | 64 ± 30 | large + small, green |
| rat5 At1012-2 | 17 ± 4 | small, yellow |
| rat5 At1012-3 | 70 ± 20 | large + medium, green |
| rat5 At1012-4 | 86 ± 6 | large, green |
| rat5 At1012-5 | 82 ± 10 | large, green |
| rat5 At1012-6 | 92 ± 5 | large, green |
| Overexpression of RAT5 in Ws (T2 plants)[a,b] | | |
| Ws | 35 ± 14 | large, green |
| Ws At1012-1 | 69 ± 27 | large, green |
| Ws At1012-2 | 68 ± 25 | large, green |
| Ws At1012-3 | 64 ± 13 | large, green |
| Ws At1012-4 | 63 ± 20 | large, green |

[a] at least 5 plants were tested for each mutant and 40-50 root bundles were tested for each plant
[b] *Agrobacterium* was diluted to a concentration 100-fold lower than that normally used, and single root segments were separated

EXAMPLES

Example 1

Results Indicating the Value of Using the *Arabidopsis* Histone H2A-1 Gene to Improve Plant Transformation Evidence from two independent lines of experimentation shows that the *Arabidopsis* histone H2A-1 is useful to improve the efficiency of *Agrobacterium*-mediated plant transformation in dicots and monocots.

1. Many *Arabidopsis* ecotypes and mutants cannot be easily transformed by a root transformation method (although they can still be transformed by the flower-dip method). The flower-dip method was used to introduce a histone H2A-1 cDNA, under the control of the CaMV 35S promoter, into a large number of recalcitrant ecotypes and mutants. A number of these transgenic lines were analyzed and evidence emerged that all ecotypes/mutants tested to date can be made competent for root transformation when they over-express the H2A-1 gene. These include mutants in the *Agrobacterium* attachment process (rat1 and rat3), T-DNA integration (rat17, rat18, rat20, and rat22), a chromatin mutant (HAT6), and several other mutants with as yet uncharacterized lesions (rat21 and ratJ7). Additionally, several recalcitrant ecotypes can be made more susceptible to transformation when the H2A-1 cDNA is over-expressed. These include the ecotypes Ag-0 and Dijon-G.

Other suitable mutants include (rat4, rat14, rat15, ratJ1, α7, T9 and T16) and ecotypes (Cal-0, UE-1, Ang-0, Petergof, and BI-1) when over-expressing the H2A-1 gene may also be more susceptible to *Agrobacterium*-mediated transformation.

2. Kan Wang at the Plant Transformation Facility, Iowa State University tested for the present invention in two different *Agrobacterium* strains. One contains a T-DNA binary vector with a herbicide resistance gene in the T-DNA (this is the control construction)1. The other strain contains a similar T-DAN binary vector, but in addition to the herbicide resistance gene the T-DNA contains the *Arabidopsis* histone H2A-1 cDNA under the control of maize adh1 promoter and intron. These strains were used in four rounds of maize transformation experiments. Usually, transformation and regeneration of maize requires an anti-oxidant (such as L-cysteine) to prevent tissue browning and necrosis as a response to the bacteria. Several thousand transformations (using the control vector without the histone gene) produced virtually no transformants. In these experiments, there were no transformants (using the control strain) without L-cysteine. With L-cysteine, about 2-3% of the infected immature embryos give transformants. Using the histone gene and L-cysteine, there was 2-3% transformation. However, with the histone gene and without L-cysteine, they obtained 2 (0.2%) transformants. Preliminary results suggest that the histone gene may sensitize the maize embryos to transformation so that a few transformants can be obtained in the absence of an anti-oxidant.

Example 2

Improved *Agrobacterium*-Based Transformation of Monocot Plants with an H2A Gene Embryos from wild-type maize plants were transformed with *Agrobacterium* containing a histone H2A gene and an antibiotic resistance gene in the presence of L-cysteine in the cocultivation medium. Transgenic T1 plants (founder lines) were obtained and their seeds (T2) were collected. T2 plants were selected on antibiotic resistance growth medium and based on histone H2A RNA expression data. Embryos from selected T2 plants (T2 embryos) were retransformed with *Agrobacterium* containing a standard binary vector and a gene of interest in the presence of L-cysteine in the cocultivation medium. An increase in the number of embryos responding indicated an increase in transformation efficiency over transformation using histone alone. Table 2 shows the overall efficiency of transformation [total putatives by event/total responding by event].

*Agrobacterium*-mediated transformation results in lower transgene copy number and higher gene expression compared with biolistic gun transformation of maize (FIGS. 9A-B). Transgene expression is also more stable in *Agrobacterium*-derived transformants than in bombardment-derived ones (FIGS. 9C-D).

Total RNA was extracted from leaves of transgenic plants twice independently, and duplicate loadings were run per extract. Thus there were four data points for each sampled plant. Plant number 9 was incorrectly identified as transgenic; it had no expression of the H2A-1 construction and therefore was used as a background control.

Figure 5:
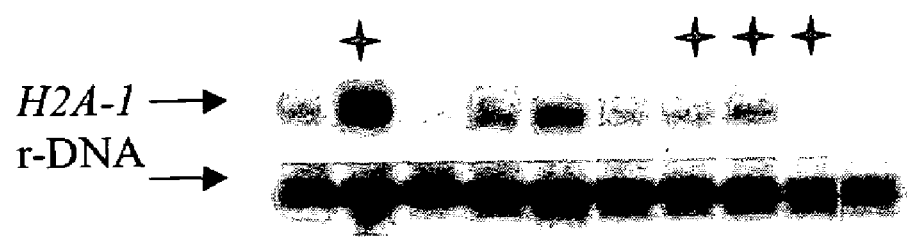
FIG. 5 shows a northern blot of H2A expressing transgenic maize lines.
Figure 10:
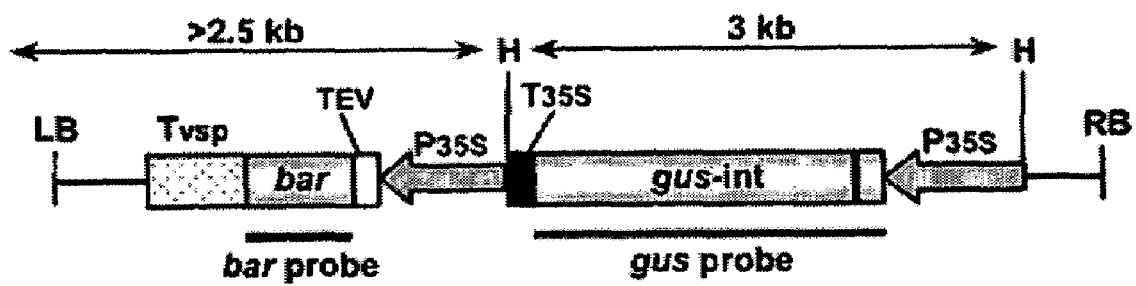
FIG. 10 is a schematic illustration of a T-DNA region of a standard binary vector pTF102. LB, Left border; RB, right border; bar, phosphinothricin acetyltransferase gene; gus-int, -glucuronidase gene containing an intron; P35S, CaMV 35S promoter; TEV, tobacco etch virus translational enhancer; Tvsp, soybean vegetative storage protein terminator; T35S, CaMV 35S terminator; H, HindIII.

Overall the H2A-1 gene was more highly expressed in A10 (H2A-containing) than in A17 (H2A lacking) lines (FIG. 5). Expression levels among the individual plants differed considerably within the A10 and A17 groups. Plant lane 2 was most intensely hybridizing, followed by the group of lines 5, 8, 6 and 7 (average), which were similar to one another (FIG. 5). The remaining lanes were less intensely hybridizing.

MATERIALS AND METHODS

Nucleic acid manipulation. Total plant genomic DNA was isolated according to the method of Dellaporta et al. (1983). Restriction endonuclease digestions, agarose gel electrophoresis, plasmid isolation, and DNA blot analysis were conducted as described (Sambrook et al., 1982).

Plasmid Rescue. Genomic DNA (5 µg) of rat5 was digested to completion with SalI. The digested DNA was extracted with phenol/chloroform and precipitated with ethanol. The DNA was self-ligated in a final volume of 500 µl in 1× ligation buffer (Promega) with 3 units of T4 DNA ligase at 16° C. for 16 hr. The ligation mixture was precipitated with ethanol, transformed into electrocompetent *E. coli* DH10B cells (mcrBC-; Life Technologies, Inc., Gaithersburg, Md.) by electroporation (25 µF, 200 Ω, and 2.5 kV) and plated on LB medium containing ampicillin (100 µg/ml). Ampicillin-resistant colonies were lifted onto a nylon membrane, the bacteria were lysed, and DNA was denatured in situ (Sambrook et al., 1982). A radiolabeled left border (LB) sequence (3.0 kbp EcoRI fragment of pE1461) was used as a hybridization probe to identify a plasmid containing the LB. Positive colonies were picked and plasmid DNA was isolated. By restriction fragment analysis a plasmid containing both the LB and plant junction DNA was identified. The plant junction fragment was confirmed by hybridizing the junction fragment to wild-type plant DNA. A restriction map of this plasmid, containing the LB-plant junction DNA, was made. A 1.7 kbp EcoRI fragment that contained plant DNA plus 75 base pairs of LB sequence was subcloned into pBluescript, resulting in pE1509. This fragment was subsequently sequenced at the Purdue University sequencing center.

Growth of *Agrobacterium* and in vitro root inoculation of *Arabidopsis thaliana*. These were performed as described previously by Nam et al. (1997).

Plant Growth Conditions. Seeds of various *Arabidopsis thaliana* ecotypes were obtained from S. Leisner and E. Ashworth (originally from the *Arabidopsis* Stock Centre, Nottingham, UK, and the *Arabidopsis* Biological Resource Center, Ohio State University, Columbus, respectively). Seeds were surface sterilized with a solution composed of 50% commercial bleach and 0.1% SDS for 10 min and then rinsed five times with sterile distilled water. The seeds were germinated in Petri dishes containing Gamborg's B5 medium (GIBCO) solidified with 0.75% bactoagar (Difco). The plates were incubated initially at 4° C. for 2 days and the fro 7 days under a 16-hr-lights/8-hr-dark photoperiod at 25° C. Seedlings were individually transferred into baby food jars containing solidified B5 medium and grown for 7 to 10 days for root culture. Alternatively, the seedlings were transferred into soil for bolt inoculation.

Growth of *Agrobacterium tumefaciens*. All *Agrobacterium* strains were grown in YEP medium (Lichtenstein and Draper, 1986) supplemented with the appropriate antibiotics (rifampicin, 10 µg/mL; kanamycin, 100 µg/mL) at 30° C. Overnight bacterial cultures were washed with 0.9% NaCl and resuspended in 0.9% NaCl a 2×109 colony-forming units per mL for in vitro root inoculation or at 2×1011 colony-forming units per mL for bolt inoculation.

In Vitro Root Inoculation and Transformation Assays Roots grown on the agar surface were excised, cut into small segments (~0.5 cm) in a small amount of sterile water, and blotted onto sterile filter paper to remove excess water. For some experiments, excised roots were preincubated on callus-inducing medium (CIM;4.32 g/L Murashige and Skoog [MS] minimal salts [GIBCO], 0.5 g/L Mes, pH 5.7, 1 mL/L vitamin stock solution [0.5 mg/mL nicotinic acid, 0.5 mg/mL pyridoxine, and 0.5 mg/mL thyamine-HCl], 100 mg/L myoinositol, 20 g/L glucose, 0.5 mg/L 2,4-dichlorophenoxyacetic acid, 0.3 mg/L kinetin, 5 mg/L indoleacetic acid, and 0.75% bactoagar) for 1 day before cutting them into segments. Dried bundles of root segments were transferred to MS basal medium (4.32 g/L MS minimal salts, 0.5 g/L Mes, pH 5.7, 1 mL/L vitamin stock solution, 100 mg/L myoinositol, 10 g/L sucrose and 0.75% bactoagar), and 2 or 3 drops of bacterial suspension were placed on them. After 10 min, most of the bacterial solution was removed, and the bacteria and root segments were cocultivated at 25° C. for 2 days.

For transient transformation assays, the root bundles were infected with *Agrobacterium* strain GV3101 was used (Koncz and Schell, 1986) containing the binary vector pBISN1 (Narasimhulu et al., 1996). After various periods of time, the roots were rinsed with water, blotted on filter paper, and stained with X-gluc staining solution (50 mM NaH2HPO4, 10 mM Na2·EDTA, 300 mM mannitol, and 2 mM X-gluc, pH 7.0) for 1 day at 37° C. For quantitative measurements of β-glucuronidase (GUS) activity, the roots were ground in a microcentrifuge tube containing GUS extraction buffer (50 mM Na2HPO4, 5 mM DTT, 1 mM Na2 EDTA, 0.1% sarcosyl, and 0.1% Triton X-100, pH 7.0), and GUS specific activity was measured according to Jefferson et al. (1987).

To quantitate tumorigenesis, root bundles were infected with wild-type *Agrobacterium* strains. After 2 days, the root bundles were rubbed on the agar surface to remove excess bacteria and then washed with sterile water containing timentin (100 µg/mL). Individual root segments (initial assay) or small root bundles (5 to 10 root segments; modified assay) were transferred onto MS basal medium lacking hormones but containing timentin (100 µg/mL) and incubated for 4 weeks.

For transformation of root segments to kanamycin resistance, root bundles were inoculated with *Agrobacterium* strain GV3101 containing pBISN1. After 2 days, small root bundles (or individual root segments) were transferred onto CIM containing timentin (100 µg/mL) and kanamycin (50 µg/mL). Kanamycin-resistant calli were scored after 4 weeks of incubation at 25° C.

To determine stable GUS expression, roots were inoculated as given above and the root segments were transferred after 2 days to CIM containing timentin (100 µg/mL) without any selection. After 4 weeks, GUS activity was assayed either by staining with X-gluc or by measuring GUS specific activity by using a 4-methylumbelliferyl β-D galactoside (MUG) fluorometric assay, as described above.

To determine the kinetics of GUS expression, root bundles were infected, the root segments were transferred after 2 days to CIM containing timentin (100 µg/mL), and calli were grown on CIM without selection. Root bundles were assayed at various times, using a MUG fluorometric assay as described above, to measure GUS specific activity.

Construction of simple binary vector systems. The based constructs are monocot-optimized (e.g. utilize monocot promoters and enhancer introns) and contain proven selectable and screenable markers (e.g. bar, gusA, gfp). The gusA gene in all constructs contains an intron to prevent expression in *Agrobacterium*. A synthetic red-shifted, maize codon-optimized close sgfp (S65T) is (Chiu et al., 1996). The CaMV 35S promoter (double promoter region) is used to drive the screenable markers. The bar gene as a selectable marker (DeBlock et al., 1987). A maize ubiquitin promoter-intron (Ubi-1) is used to drive the bar gene expression (Christensen and Quail, 1996). the vectors are designed to reduce/eliminate the occurrence of repeated sequences within the constructs. If another promoter is needed, the "super-promoter" (Ni et al., 1995) is suitable. This promoter works well in maize does not have homology to the CaMV 35S or maize ubiquitin promoters, and is freely available for licensing from the Biotechnology Research and Development Corporation. T-DNA border sequences and multiple cloning sites are included in the base constructs Construction of the binary vectors pKM4 and pKM5. The plasmid pE1509 containing the 1.7 kbp junction fragment cloned into pBluescript was digested with EcoRI to release the junction fragment. The 5' overhanging ends were filled in using the Klenow fragment of DNA polymerase I and deoxynucleotide triphosphates. The T-DNA binary vector (pE 1011) pGTV-HPT (Becker et al., 1992) was digested with the enzymes SacI and SmaI, releasing the promoterless gusA gene from pGTV-HPT. The 3' overhanging sequence of the larger fragment containing the origin of replication and the hygromycin resistance gene (hpt) were removed using the 3'-5' exonuclease activity of Klenow DNA polymerase, and the resulting 1.7 kbp blunt end fragment was ligated to the blunt ends of the binary vector. A binary vector plasmid containing the 1.7 kbp fragment in the correct orientation (pAnos downstream of the histone H2A gene) was selected and named pKM4 (strain E 1547).

An approximately 9.0 kbp wild-type genomic SacI fragment containing the histone H2A gene (RAT5) from a lambda genomic clone was cloned into the SacI site of the plasmid pBluescript. This 9.0 kbp SacI fragment was subsequently released from pBluescript by digestion with SacI and was cloned into the SacI site of the binary vector pGTV-HPT, resulting in the plasmid pKM5 (strain El 596). Both pKM4 and pKM5 were separately transferred by triparental mating (Ditta et al., 1980) into the non-tumorigenic *Agrobacterium* strain GV3101, resulting in the strains *A. tumefaciens* At1012 and At1062, respectively.

Germ-line transformation of *Arabidopsis*. Germ-line transformations were performed as described in (Bent and Clough, 1998). Transgenic plants were selected on B5 medium containing hygromycin (20 μg/ml).

*Agrobacterium tumefaciens* Vector and Strain

*A. tumefaciens* strain EHA101 (Hood et al., 1986) containing the standard binary vector pTF102 (12.1 kb) was used in all experiments. The 5.9-kb T-DNA region of this construct is shown in FIG. 1. The vector is a derivative of the pPZP binary vector (Hajdukiewicz et al., 1994) that contains the right and left T-DNA border fragments from a nopaline strain of *A. tumefaciens*, a broad host origin of replication (pVS1) and a spectinomycin-resistant marker gene (aadA) for bacterial selection. The CaMV 35S promoter (P35S) was used to drive both the bar selectable marker gene and the gus reporter gene. A tobacco etch virus translational enhancer (Carrington and Freed, 1990) was included in the 5' end of the bar gene. The soybean (Glycine max L. Merrill) vegetative storage protein terminator (Mason et al., 1993) was cloned to the 3' end of the bar gene. The gus gene contained a portable intron in its codon region (Vancanneyt et al., 1990) to prevent GUS activity in *A. tumefaciens* cells. This vector system, pTF 102 in EHA 101, was maintained on yeast extract peptone (YEP) medium (An et al., 1988) containing 100 mg/L spectinomycin (for pTF102) and 50 mg/L kanamycin (for EHA101). Bacteria cultures for weekly experiments were initiated from stock plates that were stored for up to 1 month at 4° C. before being refreshed from long-term, 80° C. glycerol stocks. In all experiments, bacteria cell densities were adjusted to an optical density ($OD_{550}$) between 0.35 to 0.45 using a spectrophotometer immediately before embryo infection.

Plant Material $F_2$ immature zygotic embryos (1.5-2.0 mm) of the maize (*Zea mays*) Hi II hybrid genotype (Armstrong et al., 1991) were aseptically dissected from greenhouse-grown ears harvested 10 to 13 d post pollination. Ears were stored up to 3 d at 4° C. before dissection.

Media

Infection, cocultivation, resting, and selection media were after Zhao et al. (1999) except that cocultivation medium was modified to contain Cys. All these media contained N6 salts and vitamins (Chu et al., 1975), 1.5 mg/L 2,4-dichlorophenoxyacetic acid, and 0.7 g L1 L-Pro in addition to the following ingredients: infection medium contained 68.4 g/L Suc and 36 g/L Glc (pH 5.2) and was supplemented with 100 μM AS (Sigma, St. Louis) before use; cocultivation medium contained 30 g/L Suc, 0.85 mg/L silver nitrate, 100 μM AS, and 3 g/L gelrite (pH 5.8); resting medium contained 30 g/L Suc, 0.5 g/L MES, 0.85 mg/L silver nitrate, 250 mg/L cefotaxime, and 8 g/L purified agar (pH 5.8). Selection medium was identical to resting medium with the addition of 1.5 or 3 mg/L bialaphos (Shinyo Sanyo, Tokyo). Infection medium was filter sterilized, whereas all other media were autoclaved. AS stock solutions (100 mM) were prepared by dissolving AS in 100% (v/v) dimethyl sulfoxide (DMSO) to make a 200 mM stock which was then diluted (1:1 [v/v]) with sterile water and stored in small aliquots at 20° C. Cys was added to cocultivation medium after autoclaving from freshly prepared, filter-sterilized stocks (100 mg/mL) and cocultivation medium was used within 2 to 5 d of preparation. Regeneration I medium contained Murashige and Skoog salts and vitamins (Murashige and Skoog, 1962), 60 g/L Suc, 100 mg/L myo-inositol, no hormones, and 3 g/L gelrite (pH 5.8) after Armstrong and Green (1985). Cefotaxime (250 mg/L) and bialaphos (3 mg/L) were added to this medium after autoclaving. Regeneration II medium differed from medium I in that it contained 30 g/L Suc and no bialaphos. All media was poured to 100-×25-mL plates.

Infection and Cocultivation

*A. tumefaciens* cultures were grown for 3 d at 19° C. on YEP medium amended with 100 mg/L spectinomycin and 50 mg/L kanamycin. One full loop (3 mm) of bacteria culture was scraped from the 3-d-old plate and suspended in 5 mL of liquid infection medium (Inf) supplemented with 100 μM AS (Inf+AS) in a 50-mL falcon tube. The tube was fixed horizontally to a bench-top shaker or a Vortex Genie platform head and shaken on low speed (approximately 75 rpm) for 4 to 5 h at room temperature. This pre-induction step was carried out for all experiments. For infection, immature zygotic embryos (1.5-2.0 mm) were dissected to bacteria-free Inf+AS medium (1.8 mL) in 2-mL eppendorf tubes (20-100 embryos per tube) and washed twice with this medium. The final wash was removed and 1 to 1.5 mL of *A. tumefaciens* suspension was added to the embryos. Embryo infection was accomplished by gently inverting the tube 20 times before resting it upright for 5 min with embryos submerged. Embryos were not vortexed at any time during this procedure. After infection, embryos were transferred to the surface of cocultivation medium and excess *A. tumefaciens* suspension was pipetted off the medium surface. Cocultivation medium contained 400 mg/L Cys unless stated otherwise. In experiments in which cocultivation medium treatments were compared, embryos were washed and infected in the same tube before being distributed between media treatments. Embryos were oriented with the embryo-axis side in contact with the medium (scutellum side up). Plates were wrapped with vent tape (Vallen Safety Supply, Irving, Tex.) and incubated in the dark at 20° C. or 23° C. for 3 d, after which embryos were transferred to 28° C. on resting medium.

Embryo response (%) was measured as the number of cocultivated immature zygotic embryos that had initiated embryogenic Type II callus formation at their scutellum base after 4 to 7 d on resting medium, compared with the total number plated. All embryos, responding or not, were transferred to selection medium.

Selection and Regeneration

After 4 to 7 d on resting medium (28° C., dark), embryos were transferred to selection medium (30 per plate) containing 1.5 mg/L bialaphos. Selection was increased to 3 mg L1 bialaphos 2 weeks later. Putatively transformed events were identified as early as 5 weeks after infection. Regeneration of R0 transgenic plants from Type II embryogenic callus was accomplished by a 2- to 3-week maturation step on Regeneration Medium I followed by germination in the light on Regeneration Medium II as described by Frame et al. (2000). Stable transformation efficiency (%) was calculated as the number of bialaphos-resistant callus events recovered per 100 embryos infected.

Acclimatization and Greenhouse Care of Transgenic Plants

Transplant and acclimatization of regenerated R0 plants was accomplished as described previously (Frame et al., 2000). Transgenic plants were grown to maturity in the greenhouse.

Statistical Analysis

Data from eight independent experiments were used to compare stable transformation efficiency from pairs of plates treated alike aside from Cys exposure during cocultivation. A sign test was used to determine whether the benefit in transgenic event recovery rate observed for the 400 mg/L Cys treatment was significantly higher than that for the 0 mg/L Cys treatment.

A Chi square test was used to determine whether the segregation ratios we observed for gus and bar gene expressing progeny plants fit the expected 1:1 ratio.

Histochemical Analysis of Transient and Stable Gus Expression

Histochemical GUS assays (Jefferson, 1987) were used to assess transient expression of the gus gene in immature zygotic embryos 1 or 2 d after the 3-d cocultivation (4 or 5 d after infection). Level of transient gus expression was assessed on a per embryo basis by estimating the number of blue foci visible on the scutellum side of each embryo. Embryos displaying blue foci only on the embryo-axis side of the explant were scored as non-expressors. The embryo was then categorized as follows: nonexpresser (no blue foci), low expresser (one-25), moderate expresser (26-100), or high expresser (>101). The number of embryos in each of these four groups was compared with the total number of embryos assessed to determine percent of total embryos in each of the expression categories. Histochemical GUS assays were also used to assess stable expression of the gus gene in bialaphos-resistant callus samples and in leaf tissue of transgenic plants in the R1 and R2 generations. Leaf segments (0.5 cm) were submerged in the substrate, vacuum infiltrated (20 inch Hg) for 10 min, and incubated at 37° C. overnight. Blue staining cells were visualized by soaking leaf tissue in 75% followed by 95% (v/v) ethanol to remove chlorophyll and leaf pieces scored as positive or negative for GUS expression.

Southern-Blot Analysis

Leaf genomic DNA was prepared from 2 to 3 g of fresh leaf tissue from putative transgenic maize plants using the cetyltrimethylammonium bromide (CTAB) method, as described by Murray and Thompson (1980). Ten micrograms of genomic DNA per sample was digested with the HindIII restriction enzyme at 37° C. overnight and separated on a 0.8% (w/v) agarose gel. DNA gel-blot analyses (Sambrook et al., 1989) were conducted on DNA samples using the 32P-labeled bar or gus fragments as shown in FIG. 1.

Progeny Segregation Analysis for Bar Gene Expression

A glufosinate leaf-spray test (Brettschneider et al., 1997) was used to establish segregation ratios for expression of the bar gene in progeny. The herbicide Liberty (Aventis, Strasbourg, France) was dissolved in water (1.25 mL/L) along with 0.1% (v/v) Tween 20 for a final glufosinate concentration of 250 mg/L. Beginning 9 d after planting, seedlings were sprayed three times at 1- to 2-d intervals with a freshly prepared glufosinate solution and then scored for herbicide resistance (alive) or herbicide sensitivity (dead).

Retransformation Experiments

A. $T_2$ Immature Zygotic Embryos

Final results for experiments on T2 embryos from T1 seed derived plants of one A10 and one A11 event were presented in the last quarterly. This approach to assessing relative transformability of A10 vs A11 events was generally unsuccessful due to poor seed set on gh T2 ears.

B. A10S1 and A11S1 Callus

All the putative events picked from this callus bombardment experiment have been gus assayed and no blue was seen in any events. Recall however, that this Nobel Foundation construct, which carries the gus gene based on the map, did not produce any transients either (while the pBGF positive control bb alongside did).

These putative events were maintained on 50 or 75 mg/L hygromycin for weeks without dieing but without being convincingly real (clones being picked for section C below are as clear as a bell). BF took a subset of the best looking ones to regeneration to see if they will harden off. At present, it is likely that we recovered few to no clones from this massive amount of work. While no conclusions can be drawn about the benefit to biolistic transformation of the expression of the H2A protein in these lines, we can conclude that hygromycin selection for rapidly growing callus needs to be applied early and strongly to minimize excessive growth during subsequent selection.

C. A10 and A11 T1 Embryos

Putative clones from T1 embryos of A10 (experimental) and A11 (control) T0 plants retransformed with pTOK233 have been picked, gus assayed and some named this quarter. The number of ears per A10 or A11 event, the numbers of embryos per ear infected and the number taken to hygromycin selection after resting the embryos on 2 mg/L bialaphos to kill-off the non-segregating embryos are summarized in Table 1. We have named 33 A10 putatives and 23 A11 putatives of which 15/17 and 10/22 of those assayed to date are gus positive, respectively. Using the number of embryos responding after resting on medium containing 2 mg/L bialaphos (to kill non A10 or A11 segregating T1 embryos), the overall efficiency for A10S1 retransformation using A18S6 was 33 events/401 infected, non-dead embryos (8.2%) and for A11S1 was 23 events/753 embryos (3%) (Table 2). This suggests that, over 16 A10S1 ears and 17 A11S 1 ears, the average efficiency of transformation was higher for A10 than A11 in this screen.

TABLE 2

Summary of retransformation experiment

| Cross ID | Northern expression levels in original event | total # of ear | total infected by event | total resp by vent | total putatives by event | Overall efficiency |
|---|---|---|---|---|---|---|
| H2A expressing lines: | | | | | | |
| A10S1-44 X B73 | LOW | 4 | 202 | 104 | 0 | 0.0 |
| A10S1-46 X B73 | HIGH | 5 | 269 | 128 | 8 | 6.3 |
| A10S1-47 X B73 | HIGH | 1 | 30 | 12 | 2 | 16.7 |
| A10S1-48 X B73 | LOW | 2 | 107 | 26 | 5 | 19.2 |
| A10S1-49 X B73 | MOD-HIGH | 2 | 141 | 75 | 11 | 14.7 |
| A10S1-51 X B73 | MOD | 2 | 101 | 56 | 7 | 12.5 |
| Total | | 16 | 850 | 401 | 33 | 8.2 |
| Vector control lines: | | | | | | |
| A11S1-27 X B73 | NONE | 2 | 261 | 136 | 2 | 1.5 |
| A11S1-30 X B73 | NONE | 3 | 275 | 184 | 7 | 3.8 |
| A11S1-31 X B73 | NONE | 5 | 395 | 211 | 7 | 3.3 |
| A11S1-33 X B73 | NONE | 3 | 270 | 141 | 7 | 5.0 |
| A11S1-34 X B73 | NONE | 4 | 224 | 81 | 0 | 0.0 |
| Total | | 17 | 1425 | 753 | 23 | 3.1 |

DOCUMENTS CITED

The following documents are incorporated by reference to the extent they enable the present invention:

Armstrong C L, Green C E (1985) Establishment and maintenance of friable, embryogenic maize callus and the involvement of L-proline. Planta 164: 207-214

Armstrong C L, Green C E, Phillips R L (1991) Development and availability of germplasm with high type II culture formation response. Maize Genet Coop Newslett 65: 92-93

Ballas, N. & Citovsky, V. Nuclear localization signal binding protein from *Arabidopsis* mediates nuclear import of *Agrobacterium* VirD2 protein. Proc. Natl. Acad. Sci. USA 94, 10723-10728 (1997).

Bent, A. F. & Clough, S. J. in Plant Molecular Biology Manual, (eds Gelvin, S. B. & Verma, D. P. S.) vol. 3, pp. B7/1-14 (Kluwer Academic Publishers, Netherlands, 1998).

Brettschneider R, Becker D, Lorz H (1997) Efficient transformation of scutellar tissue of immature maize embryos. Theor Appl Genet 94: 737-748

Carrington J C, Freed D D (1990) Cap-independent enhancement of translation by a plant potyvirus 5' nontranslated region. J Virol 64: 1590-1597

Chiu et al. (1996) Curr. Biol. 6: 325-330

Christensen and Quail (1996) Transgenic Res. 5: 213-218

Chu C C, Wang C C, Sun C S, Hsu C, Yin K C, Chu C Y, Bi F Y (1975) Establishment of an efficient medium for anther culture of rice through comparative experiments on the nitrogen source. Sci Sin 18: 659-668

DeBlock et al. (1987) The EMBO J. 6: 2513-2518

Dellaporta, S. L., Wood, J., & Hicks, J. B. Plant Mol. Biol. Rep. 1, 19-22 (1983).

Ditta, G., Stanfield, S., Corbin, D., & Helinski, D. R. Proc. Natl. Acad. Sci USA 77, 7347-7351 (1980).

Enriquez-Obregon G A, Prieto-Samsonov D L, de la Riva G A, Perez M, Selman-Housein G, Vazquez-Padron R I (1999) *Agrobacterium*-mediated Japonica rice transformation: a procedure assisted by an anti-necrotic treatment. Plant Cell Tissue Organ Cult 59: 159-168

Frame B, Zhang H, Cocciolone S, Sidorenko L, Dietrich C, Pegg S, Zhen S, Schnable P, Wang K (2000) Production of transgenic maize from bombarded Type II callus: effect of gold particle size and callus morphology on transformation efficiency. In Vitro Cell Dev Biol Plant 36: 21-29

Hajdukiewicz P, Svab Z, Maliga P (1994) The small, versatile pPZP family of *Agrobacterium* binary vectors for plant transformation. Plant Mol Biol 25: 989-994

Hood E E, Helmer G L, Fraley R T, Chilton M D (1986) The hypervirulence of *Agrobacterium tumefaciens* A281 is encoded in a region of pTiBo542 outside of T-DNA. J Bacteriol 168: 1291-1301

Jefferson R A (1987) Assaying chimeric genes in plants. The gus gene fusion system. Plant Mol Biol Rep 5: 287-405

Jefferson, R. A. m Kavanagh, T. A., Bevan, M. W. GUS fusions: Beta-glucuronidase as a sensitive and versitile gene fusion marker in higher plants. EMBO J. 6, 391-3907 (1987).

Koncz, C. and Schell, J. Mol. Gen. Genet. 204, 383-396 (1986).

Lichtenstein, C. and Draper, J. Genetic engeneering of plants. In Glover, D. M. (ed.) DNA Cloning: A Practical Approach, vol. 2, pp. 67-119 (IRL Press, Oxford, 1986).

Mason H S, DeWald D, Mullet J E (1993) Identification of a methyl jasmonate-responsive domain in the soybean vspB promoter. Plant Cell 5: 241-251

Murashige T, Skoog F (1962) A revised medium for rapid growth and bioassays with tobacco tissue cultures. Physiol Plant 15: 473-497

Murray M G, Thompson W F (1980) Rapid isolation of high-molecular-weight plant DNA. Nucleic Acids Res 8: 4321-4325

Mysore, K. S., Yi, H. C. & Gelvin, S. B. Molecular cloning, characterization and mapping of histone H2A genes in *Arabidopsis*. In preparation.

Mysore, K. S. et al. Role of the *Agrobacterium tumefaciens* VirD2 protein in T-DNA transfer and integration. Mol. Plant-Microbe Interact. 11, 668-683 (1998).

Nam J. et al. Identification of T-DNA tagged *Arabidopsis* mutants that are resistant to transformation by *Agrobacterium*. Mol. Gen. Genet. 261, 429-438 (1999).

Nam, J., Matthysse, A. G. & Gelvin, S. B. Differences in susceptibility of *Arabidopsis* ecotypes to crown gall disease may result from a deficiency in T-DNA integration. Plant Cell 8, 873-886 (1997).

Narasimhulu, S. B., Deng, X.-B. Sarria, R. & Gelvin, S. B. Early transcription of *Agrobacterium* T-DNA genes in tobacco and maize. Plant Cell 8, 873-886 (1996).

Ni, M. et al. Strength and tissue specificity of chimeric promoters derived from the octopine and mannopine synthase genes. Plant J. 7, 661-676 (1995).

Sambrook, M. A., Fritsch, E. F., & Maniatis, T. (1982) in Molecular cloning: A laboratory manual. 1 st ed. (Cold Spring Harbor Laboratory Press, Cold Spring Harbor, N.Y.)

Sambrook J, Fritsch E F, eds (1989) Molecular Cloning: A Laboratory Manual, Ed 2. Cold Spring Harbor Laboratory Press, Cold Spring Harbor, N.Y.

Vancanneyt G, Schmidt R, O'Connor-Sanchez A, Willmitzer L, Rocha-Sosa M (1990) Construction of an intron-containing marker gene: splicing of the intron in transgenic plants and its use in monitoring early events in *Agrobacterium*-mediated plant transformation. Mol Gen Genet 220: 245-250

Zhao Z Y, Gu W, Cai T, Pierce D A, inventors. Nov. 9, 1999. Methods for *Agrobacterium*-mediated transformation. U.S. Pat. No. 5,981,840

Zhao Z Y, Gu W, Cai T, Tagliani L A, Hondred D A, Bond D, Krell S, Rudert M L, Bruce W B, Pierce D A (1998) Molecular analysis of T0 plants transformed by *Agrobacterium* and comparison of *Agrobacterium*-mediated transformation with bombardment transformation in maize. Maize Genet Coop Newslett 72: 34-37.

SEQUENCE LISTING

<160> NUMBER OF SEQ ID NOS: 40

<210> SEQ ID NO 1
<211> LENGTH: 1684
<212> TYPE: DNA
<213> ORGANISM: Arabidopsis thaliana

<400> SEQUENCE: 1

```
tcaaaaggaa agacattaaa ttagaaattg aattttgaaa catgttgata gatcatgtcc      60
ttcttctggg ttacccagtt ttgccctaaa acctaaaacc aacaggacca tcatttcgac     120
cacaccacat tgactggtct gccccaatct agctatgata tatcttaatt tccgtatgac     180
ttggatccat aaatattgaa atagatttgg tgaacacaaa ttactcttaa aacttcttct     240
ctttcatgca tgttctttt ctcactttaa catttttata tagtgacatt tttagtaatc      300
caacgttatt tatatgatta gtaattcatc aaatttatat agtgataaaa ttccacaatg     360
gttgttcaat aaaaatatga acaacacaat agaattagta aaagtgacta tgttaaatca     420
ttttcttcgc tggggtttgg tgggcgagtt ctaaacccat aagcggccca tttacttcgt     480
aaactcaatt cgatttgttc agcgttccaa gcccataata ttattttcaa gggcataaaa     540
taaattgagg tttatatgga aaatttggaa attccctcgt ccagaagaaa ccaacaaaaa     600
actgcaaaag ttcaagcggt gggagaaaaa acttcagatc gtagccattc attaaattat     660
aatcaacggt ttaaacctct tcgatccgcg tactctattc cttatggtca aataacttaa     720
tcctccacat atataacaac aatcagattt ctctctgtta atttcgtcaa gaaaaaaatt     780
cgattttttt gcgctctttg tgggttgttg ttgttgaaaa tggctggtcg tggaaaaact     840
cttggatccg gtggggcgaa gaaagctaca tctcggagta gcaaagccgg tcttcaattc     900 ccgtgggtc gtatcgctcg tttcttaaaa gccggtaaat acgccgaacg tgttggtgcc      960
ggtgctccgg tttatctcgc cgccgttctc gaatatttgg ccgccgaggt aaaattacat    1020
cgtcttttct ctctttccca ttccgtttcc gatcttattc gtctgactct gttttttgcgt    1080 gatcgattac gaatctaggg ttcttacatt ttccgaattt gacatgcaaa aattgaatta    1140
gattcgtgtt tgaattgaat tgttgtagtt ctgtaattga cctaattttg ggtttgttct    1200
gattggttga tggtaatcga gatcatatga atcgttgtag ttttctcgca agattctaaa    1260 ttttttttcaa ttatggtaac caatttgatt tgagttgtta aagttctcaa atttggaaag    1320
tttgatcatg aattgtgtgt tttgaatttg ttcaggttct tgaattagct ggaaacgcag    1380
```

-continued

```
caagagacaa caagaagaca cgtattgttc ctcgtcacat tcagcttgcg gtcagaaacg   1440
atgaggagct aagcaagctt cttggagatg tgacgattgc taatggagga gtgatgccta   1500
acatccacaa tctccttctc cctaagaagg ctggtgcttc aaagcctcag gaagattagg   1560
tcttttaaca caatgatata gaacacgtct ctcttttgca tttttcagga tatattgtgg   1620
tgtaaacaaa ttgacgctta gacaacttaa taacacattg cggacgtttt taatgtactg   1680
aatt                                                                 1684

<210> SEQ ID NO 2
<211> LENGTH: 638
<212> TYPE: DNA
<213> ORGANISM: Arabidopsis thaliana

<400> SEQUENCE: 2
taatttcgtc aagaaaaaaa ttcgattttt ttgcgctctt tgtgggttgt tgttgttgaa     60
aatggctggt cgtggaaaaa ctcttggatc cggtggggcg aagaaagcta catctcggag    120
tagcaaagcc ggtcttcaat tcccggtggg tcgtatcgct cgtttcttaa aagccggtaa    180
atacgccgaa cgtgttggtg ccggtgctcc ggtttatctc gccgccgttc tcgaatattt    240
ggccgccgag gttcttgaat tagctggaaa cgcagcaaga gacaacaaga agacacgtat    300
tgttcctcgt cacattcagc ttgcggtcag aaacgatgag gagctaagca agcttcttgg    360
agatgtgacg attgctaatg gaggagtgat gcctaacatc cacaatctcc ttctccctaa    420
gaaggctggt gcttcaaagc tcaggaagat taggtctttt aacacaatg atatagaaca    480 cgtctctctt ttggctttag atctaataac ctaataacta gctagatgtt ttcactttt    540 gtatctttgc tttttttaat tcctttaggg atttgtttct ttccgtttct gtttcgacat    600
gttgtttctg tttttgtgaa tatatgaaag tattttgc                            638

<210> SEQ ID NO 3
<211> LENGTH: 639
<212> TYPE: DNA
<213> ORGANISM: Arabidopsis thaliana

<400> SEQUENCE: 3
gagaaatttc tcagttacgc ttcatcctcc tctaagagat ctttttttcta tcttgggtag    60 tagagagaaa tggcgggtcg gggaaaaacaa cttggatctg gtgcagcgaa gaagtctact   120
tctcgtagta gcaaggctgg gcttcaattc cctgttggtc gtatcgctcg atttttgaaa   180
gccggtaagt acgccgagcg tgttggtgcc ggagctccgg tctatctcgc cgccgttctt   240
gaatacctcg ccgctgaggt acttgagctt gctgggaacg cagcgagaga caacaagaag   300
acccgtatag ttccacgaca cattcagctt gctgtgagga atgatgagga gctaagcaag   360
ttgcttggag atgtgacaat tgctaatgga ggagtgatgc ctaacatcca caatctcctt   420
ctccccaaga aggctggttc atctaagcct actgaagaag attaggttca ttacgaagat   480
agggaaagct ggaaactggt tgatatcaga taatgcttag gattgttttt tttttcattt    540
gcttttcctc tgcagcaatg gaagctgtgt ggttgtacta gttgttaagg ttacctttgt    600
ttcactttat gtgaatatat gaagaaattg ttctatttc                            639

<210> SEQ ID NO 4
<211> LENGTH: 801
<212> TYPE: DNA
<213> ORGANISM: Arabidopsis thaliana

<400> SEQUENCE: 4
```

```
aaatcactcc actcacaaaa tcctcagcca tctctaatca catttacaa tcgcctcttc      60 aaatttcccg ataaacaaaa aatgagttcc ggcgccggca gtggaacaac taaaggtggc     120
agaggaaagc caaagctac aaagtccgtc tctcgatctt ctaaagctgg tcttcaattt      180
cccgttggaa gaatcgctag attccttaaa gccggtaaat acgccgaacg tgttggtgcc    240
ggtgctcccg tttatctctc cgccgttctc gaatacctcg ccgctgaggt attggagcta    300
gctggaaatg cagcaagaga taacaagaag acacgtatcg taccacggca cattcagctt     360
gcagtgagga acgatgaaga gcttagtaaa cttcttggaa gtgtaacaat tgctaatgga    420
ggagttttgc ccaacattca tcagactctt ctcccatcaa aggttggaaa gaacaaaggc    480
gatatcggat ctgcttctca agagttttaa ttttattttt tagcttgtaa catagacatg    540
gctctctgtt ccacaatagt tttggtattt tcatgttact caaaaactgt gtttgcaaat    600
ccagtaatga attcggtttg aagaagtgaa atagttaaat ttgatgtgtt gaaatagcgg    660
attcaatggc ttcaatacaa gtgctaatag gtttggcttt agccatggtt tctgcaagtg    720
agactcttgc ttcttttgtga gaatgtaata atgagacagt gttggaaaca gcccatttga    780
tatgagcctc cttttctgat t                                              801

<210> SEQ ID NO 5
<211> LENGTH: 357
<212> TYPE: DNA
<213> ORGANISM: Arabidopsis thaliana

<400> SEQUENCE: 5
atggtgtgca acacgaatat actaaaagat gtgtcgacga agataagtgc ttttgaaaat     60
gttcggatga ttatggtgga gggagagatg tttcaagtgg ctcgtattca caagcaactt    120
aagaacagag tttctgcaca tagtagtgtt ggtgcgactg atgttgtcta catgacttca    180
atccttgaat acctaactac agaggttctt cagttggccg aaaacactag caaagattta    240
aaagtgaaga ggataactcc aaggcatttg cagttggcga tcagaggaga tgaagagctt    300
gacacactca tcaaaggaac aattattgga ggaagtgtga tccctcacat ccactag       357

<210> SEQ ID NO 6
<211> LENGTH: 739
<212> TYPE: DNA
<213> ORGANISM: Arabidopsis thaliana

<400> SEQUENCE: 6
catatagaga agagcaaaac cctaaagccc actcatcttc tcaattccca gatcatctac     60
aatagtcatt tctcttcgat ttcttcaaac tctcatcaaa tcgtttatct gttctaaatt    120
tcgaagaaga cgatgagtac aggcgcagga agcggaacaa ccaaaggtgg cagaggaaag    180
ccaaaggcca ccaaatccgt ctctcgatca tctaaagccg tcttcaatt ccccgtcgga    240 agaatcgcta gattcctcaa atccggtaaa tacgccgagc gtgtcggtgc cggagctccg    300
gtctatctct ccgctgttct cgagtacctc gccgccgagg tgttggagct ggcgggaaac    360
gcagcaaggg ataacaagaa gacacgtata gtaccaagac acattcagct tgcagtgagg    420
aacgatgaag agttaagcaa acttctggga agtgtgacga ttgcgaatgg aggagttttg    480
ccaaatattc atcagactct tttgccatcc aaggttggca gaacaaagg agatattgga    540 tctgcttctc aggagttctg aggttcttag acttcttagt tcagttctct tgtttggatt    600
cggaacttgt aaaatagacc ctgatggtgt ttttgggga tcaaattagg ttttaaagct    660
```

```
aagtatattt ggcttttgcc taagtatgtt taattagtga atgatatgat atttcggaac    720
gaatcatgta tcaatggaa                                                 739
```

<210> SEQ ID NO 7
<211> LENGTH: 699
<212> TYPE: DNA
<213> ORGANISM: Arabidopsis thaliana

<400> SEQUENCE: 7

```
ttaaatcaca aatcttcaac ttccgatact ttcaatctct ctaaactctc aatttcagta     60
atcgataacc gtagcaatgg aatccaccgg aaaagtgaag aaagctttcg gaggaagaaa    120
accacctggt gccccaaaaa ccaaatcggt ttcgaaatcg atgaaagccg gtcttcaatt    180
cccagtggga agaatcactc gtttcctgaa gaaaggacga tacgctcaga gacttggtgg    240
tggtgctccg gtttacatgg ccgccgttct tgaataccct gccgcagaag ttctggagct    300
tgctggtaac gctgcgagag ataacaagaa atcaaggata attccgaggc atcttcttct    360
cgcgataagg aacgatgaag aattggggaa acttctgagt ggtgtcacaa tcgctcacgg    420
tggtgttttg cctaacatca actctgttct attgcctaag aagtctgcca ctaaaccagc    480
tgaagaaaag gctaccaaat caccagtcaa gtctccaaag aaagcttaat ctgctagagt    540
tttcgttgct agtttgtgtt tgagctctgg tgaatgtaga aatttgaagc ttttggatct    600
tagtttctat gtatttggtg atttagaatg ttgttcaaaa tcctttttcct aatcataaga    660 atttatgatc tatctattat acgcttcgtc taatctttt                           699
```

<210> SEQ ID NO 8
<211> LENGTH: 759
<212> TYPE: DNA
<213> ORGANISM: Arabidopsis thaliana

<400> SEQUENCE: 8

```
caaatcgtaa accgccacaa aaccgaaaaa aacactaatt gtgctttccc tttagattca     60
tttgtatttt cttttggagc ttttgaacaa tggagtcatc acaagcaacg acgaagccaa    120
cgagaggagc aggaggaagg aaaggtggag ataggaagaa gagtgttagt aaatctgtta    180
aagctggtct tcaatttccc gttggtcgta tcgctcgtta cttgaagaaa ggtcggtacg    240
ctctccgata cggttccggt gctccggttt acctcgccgc cgttctcgaa tacctagccg    300
ccgaggtact tgagctagct gggaacgcag cgagagataa taagaagaac aggataaaacc    360 ctaggcatct atgtttagcg ataaggaacg atgaggaatt ggggagattg cttcatggag    420
ttactattgc tagtggtggt gttcttccaa acattaatcc agttcttctt cctaagaaat    480
caacagcttc ttcttctcaa gcggagaaag cttctgctac caaatctcct aagaaggctt    540
gataaagaat agtatcgatg ttgcttttttg gttatattcg gatcttagat gaagaagaag    600
aagaagaaga acaacttgt tttttgtttt agaggattg tgtaggtatc tgaaatcttc       660
ttctctttgt tttggtttgt cttatgtaaa aaccatggga agatgattat gtttgttaac    720
gcaatttgta atggaaaata attaagttct gggattagt                           759
```

<210> SEQ ID NO 9
<211> LENGTH: 674
<212> TYPE: DNA
<213> ORGANISM: Arabidopsis thaliana

<400> SEQUENCE: 9

```
aattcgacgt ctctcttttg tctctgtatc gattttctcg ccgcgaattt cgaataggtt     60
```

-continued

```
cttcaccata agcttgagat cttatttctc tactgttctt tgcttcttct ctatcgatat      120
ggctggtaaa ggtgggaaag ggcttctagc tgcgaagacg acggcagcag ctgcaaacaa      180
agacagtgtt aagaagaaat ccatctctcg ctcttctcgt gctggtattc agtttccagt     240
gggtcgtatt catcgtcaac tcaagcaaag agtttcagca catggaagag ttggtgccac     300
tgctgctgtt tacactgcat caattctaga atacttgact gctgaagtac tcgagttagc     360
tggaaatgcg agcaaggatc tcaaagtgaa gagaattaca ccaagacatt gcagcttgc      420 aatcagagga gatgaggaac ttgacactct catcaaagga accattgcag gaggaggtgt     480
gatccctcac atccacaagt cccttgtcaa caaagtcacc aaggattgag tttcgctctc     540
tgagtcctaa gtctctatta tactatgtgc tcttttctag acgccctcat gtgtatatgg     600
gttcattgta tctcttaggt ctctcgtttt agactcatac tcttgttatt ttgctaatgc     660
ttacatgatt gagg                                                       674

<210> SEQ ID NO 10
<211> LENGTH: 726
<212> TYPE: DNA
<213> ORGANISM: Arabidopsis thaliana

<400> SEQUENCE: 10
atcgggagac tcctcttcga gctcatcttc ttctctctct ttttatcttt ggttgtgcga      60
tctcctttct ctttcaatct ccaaggattt tactgtgaga tatttggcgg gaaaatgtcg     120
gggaaaggtg ctaaaggttt gattatgggg aaacccagcg gtagcgacaa ggataaggac     180
aagaagaagc ctatcactcg ttcttctcga gctggtctcc agttcccagt tggtagggtg     240
catcgtctgt taaagacaag gtccactgct catggaaggg ttggagcaac tgcagctgtt     300
tacacagcag caatattgga gtatctgact gcagaagttt tggagttggc tggtaacgcc     360
agcaaggact tgaaggtgaa acgtatctcg ccgaggcatt tgcagcttgc gattcgtgga     420
gatgaggagc tcgatactct catcaaagga actatagctg gtggtggagt catccctcat     480
atccacaaga gtctcatcaa caaatccgcc aaggaatagg acttttttag ttacccgctt     540
tgttctgtgt tgcttttctg ttttctaaat gttttaagaa gttgttgttt gataagatgc     600
tagagaagct cttttagga tcgtttgcta ttgttcgttc gatcagcgta ctttgtgtta     660
gagacgccag tcgatttatc tatctttaaa aatgtattcg aatgattatc caaaaccat     720 ttctga                                                               726

<210> SEQ ID NO 11
<211> LENGTH: 635
<212> TYPE: DNA
<213> ORGANISM: Arabidopsis thaliana

<400> SEQUENCE: 11
aacaacaaat tcgattctta taactgtttc cctctcatct ttacacaaaa gtattctaat      60
cgatttcaat ggcgggtcgt ggtaaaacac tcggatctgg gtctgcgaag aaggcaacaa     120
caagaagcag caaagccggt ctccaattcc ctgtgggtcg tatcgctcgt ttcttgaaga     180
aaggcaaata cgccgaacgt gttggtgccg gagctccggt ttacttagcc gccgttctcg     240
aatacctcgc cgctgaggta ttggaattgg ctggaaacgc agcgagggat aacaagaaga     300
cgaggattgt tccaaggcat attcaattgg cggtgaggaa cgatgaagaa ttgagcaaat     360
tgcttggaga tgtgactatt gctaatggag gtgtgatgcc taacattcac aatcttcttc     420
```

```
ttcctaagaa gaccggtgct tccaagccat ctgctgaaga cgattgatta atcaaccaaa    480
tccactctct tgtgttttttt gagttttaa ggcttttaa gagtaattta gattagatct    540
atggtgaaga aagaatctat cttctgtgtt ttttgaattg aattgaatgt tcatatgctt    600
tcaatttctt atggaatcaa gattttaact tttct                              635

<210> SEQ ID NO 12
<211> LENGTH: 615
<212> TYPE: DNA
<213> ORGANISM: Arabidopsis thaliana

<400> SEQUENCE: 12 cctttttgcat tctctcgtcg tcgtctcaag atctagaaga aggaaacaac aatttcaaga    60
gacatggcag gcaaaggtgg aaaaggactc gtagctgcga agacgatggc tgctaacaag   120
gacaaagaca aggacaagaa gaaacccatc tctcgctctg ctcgtgctgg tattcagttt   180
ccagttggac gaattcacag gcaactgaag acccgagtct cggcacatgg cagagttggt   240
gccactgcag ccgtctacac agcttcaatc ctggagtatc tgacagcaga ggttcttgag   300
ttggctggga atgcgagcaa ggatctcaaa gtgaagagga taacgccaag gcatctgcag   360
ttggcgatta gaggagatga ggagctggac acactcatca agggaacgat tgctggaggt   420
ggtgtgatcc ctcacatcca caagtctctc atcaacaaaa ccaccaagga gtgatgtgta   480 gcttttatg gtgtttgtat ttctgtagtc ttggactcat tttcctttat ccttttctta   540
gttctttgac tagtgttgac ctcttctgga catcctcagg tgtacattag ttaatttgaa   600 ctcttttaggt tcctt                                                   615

<210> SEQ ID NO 13
<211> LENGTH: 612
<212> TYPE: DNA
<213> ORGANISM: Arabidopsis thaliana

<400> SEQUENCE: 13
atggattccg gaaccaaagt gaagaaagga gccgctggaa gaagaagtgg tggaggtcct    60
aagaagaaac cggtttcccg ttcggttaaa tccggtctac agtttcctgt cggtaggatc   120
ggtcggtatc ttaagaaagg tcgttattcg aagcgtgtcg gaaccggagc tccggtctat   180
ctcgccgccg tcctcgagta tcttgctgct gaggttctcg agcttgctgg taacgctgca   240
agagataaca aaaagaaccg tattatacca cgccatgttc tattagcggt gaggaacgac   300
gaggagctag gacactact caaaggcgta accattgcac acggcggtgt tttaccaaac   360
ataaacccaa tactcctccc aaagaagtct gagaaagcag cttcaactac aaaaacaccc   420
aaatcaccat caaaggcaac caaatcccct aagaatctt agtacttctt tcttcattcc   480
tctgtataac ctactgtttc tatctctctg tacgtttctc tgtaaagaca gaacagaata   540
tctctttgtt gttgtgagaa agcttagttt ctctgatcgt cgttgtgaaa taaaaaatgc   600
aacgtttcat at                                                       612

<210> SEQ ID NO 14
<211> LENGTH: 592
<212> TYPE: DNA
<213> ORGANISM: Arabidopsis thaliana

<400> SEQUENCE: 14
atcttaattt ccctcgcatt gagaatttc aacttttct atctctcttc ccaaatcaca    60
aatggcgggt cgcggcaaaa ctctcggatc tggcgttgct aagaaatcaa catcgagaag   120
```

-continued

```
cagcaaagcc ggtctccaat tccccgttgg tcgtatcgct cgttttctaa agaacggcaa    180
gtacgcaaca cgtgttggtg ccggagctcc ggtttactta gccgccgttc tcgaataacct   240 cgccgctgag gtattggaat tggctggaaa cgcagctagg gataacaaga agactaggat    300
tgtgccacgt cacattcagc tcgcggtgag aaacgatgag gagctgagta aactgcttgg    360
agatgtgacg attgctaatg gaggtgtgat gcctaacatt cacagtcttc ttcttcccaa    420
gaaagctggt gcttcaaaac cttccgctga tgaagattag attagggatt tgtgttgtgg    480
ttgtttagct aattaatgtg tagcttagtc tttcattaga ttagatctga attagttttc    540
attaatggtg ttgtgtagtc tctcttttgc ttcaaaaaca agtattaaaa tc            592
```

```
<210> SEQ ID NO 15
<211> LENGTH: 130
<212> TYPE: PRT
<213> ORGANISM: Arabidopsis thaliana

<400> SEQUENCE: 15
```

Met Ala Gly Arg Gly Lys Thr Leu Gly Ser Gly Ala Lys Lys Ala
1               5                   10                  15

Thr Ser Arg Ser Ser Lys Ala Gly Leu Gln Phe Pro Val Gly Arg Ile
                20                  25                  30

Ala Arg Phe Leu Lys Ala Gly Lys Tyr Ala Glu Arg Val Gly Ala Gly
            35                  40                  45

Ala Pro Val Tyr Leu Ala Ala Val Leu Glu Tyr Leu Ala Ala Glu Val
        50                  55                  60

Leu Glu Leu Ala Gly Asn Ala Ala Arg Asp Asn Lys Lys Thr Arg Ile
65                  70                  75                  80

Val Pro Arg His Ile Gln Leu Ala Val Arg Asn Asp Glu Glu Leu Ser
                85                  90                  95

Lys Leu Leu Gly Asp Val Thr Ile Ala Asn Gly Gly Val Met Pro Asn
            100                 105                 110

Ile His Asn Leu Leu Pro Lys Lys Ala Gly Ala Ser Lys Pro Gln
        115                 120                 125

Glu Asp
    130

```
<210> SEQ ID NO 16
<211> LENGTH: 131
<212> TYPE: PRT
<213> ORGANISM: Arabidopsis thaliana

<400> SEQUENCE: 16
```

Met Ala Gly Arg Gly Lys Gln Leu Gly Ser Gly Ala Ala Lys Lys Ser
1               5                   10                  15

Thr Ser Arg Ser Ser Lys Ala Gly Leu Gln Phe Pro Val Gly Arg Ile
                20                  25                  30

Ala Arg Phe Leu Lys Ala Gly Lys Tyr Ala Glu Arg Val Gly Ala Gly
            35                  40                  45

Ala Pro Val Tyr Leu Ala Ala Val Leu Glu Tyr Leu Ala Ala Glu Val
        50                  55                  60

Leu Glu Leu Ala Gly Asn Ala Ala Arg Asp Asn Lys Lys Thr Arg Ile
65                  70                  75                  80

Val Pro Arg His Ile Gln Leu Ala Val Arg Asn Asp Glu Glu Leu Ser
                85                  90                  95

Lys Leu Leu Gly Asp Val Thr Ile Ala Asn Gly Gly Val Met Pro Asn

-continued

```
                100                 105                 110
Ile His Asn Leu Leu Pro Lys Lys Ala Gly Ser Ser Lys Pro Thr
        115                 120                 125

Glu Glu Asp
    130
```

<210> SEQ ID NO 17
<211> LENGTH: 142
<212> TYPE: PRT
<213> ORGANISM: Arabidopsis thaliana

<400> SEQUENCE: 17

```
Met Ser Ser Gly Ala Gly Ser Gly Thr Thr Lys Gly Arg Gly Lys
  1               5                  10                  15

Pro Lys Ala Thr Lys Ser Val Ser Arg Ser Ser Lys Ala Gly Leu Gln
             20                  25                  30

Phe Pro Val Gly Arg Ile Ala Arg Phe Leu Lys Ala Gly Lys Tyr Ala
         35                  40                  45

Glu Arg Val Gly Ala Gly Ala Pro Val Tyr Leu Ser Ala Val Leu Glu
     50                  55                  60

Tyr Leu Ala Ala Glu Val Leu Glu Leu Ala Gly Asn Ala Ala Arg Asp
 65                  70                  75                  80

Asn Lys Lys Thr Arg Ile Val Pro Arg His Ile Gln Leu Ala Val Arg
                 85                  90                  95

Asn Asp Glu Glu Leu Ser Lys Leu Leu Gly Ser Val Thr Ile Ala Asn
            100                 105                 110

Gly Gly Val Leu Pro Asn Ile His Gln Thr Leu Leu Pro Ser Lys Val
        115                 120                 125

Gly Lys Asn Lys Gly Asp Ile Gly Ser Ala Ser Gln Glu Phe
    130                 135                 140
```

<210> SEQ ID NO 18
<211> LENGTH: 118
<212> TYPE: PRT
<213> ORGANISM: Arabidopsis thaliana

<400> SEQUENCE: 18

```
Met Val Cys Asn Thr Asn Ile Leu Lys Asp Val Ser Thr Lys Ile Ser
  1               5                  10                  15

Ala Phe Glu Asn Val Arg Met Ile Met Val Glu Gly Glu Met Phe Gln
             20                  25                  30

Val Ala Arg Ile His Lys Gln Leu Lys Asn Arg Val Ser Ala His Ser
         35                  40                  45

Ser Val Gly Ala Thr Asp Val Val Tyr Met Thr Ser Ile Leu Glu Tyr
     50                  55                  60

Leu Thr Thr Glu Val Leu Gln Leu Ala Glu Asn Thr Ser Lys Asp Leu
 65                  70                  75                  80

Lys Val Lys Arg Ile Thr Pro Arg His Leu Gln Leu Ala Ile Arg Gly
                 85                  90                  95

Asp Glu Glu Leu Asp Thr Leu Ile Lys Gly Thr Ile Ile Gly Gly Ser
            100                 105                 110

Val Ile Pro His Ile His
        115
```

<210> SEQ ID NO 19
<211> LENGTH: 142
<212> TYPE: PRT

<213> ORGANISM: Arabidopsis thaliana

<400> SEQUENCE: 19

Met Ser Thr Gly Ala Gly Ser Gly Thr Thr Lys Gly Arg Gly Lys
1               5                   10                  15

Pro Lys Ala Thr Lys Ser Val Ser Arg Ser Ser Lys Ala Gly Leu Gln
            20                  25                  30

Phe Pro Val Gly Arg Ile Ala Arg Phe Leu Lys Ser Gly Lys Tyr Ala
        35                  40                  45

Glu Arg Val Gly Ala Gly Ala Pro Val Tyr Leu Ser Ala Val Leu Glu
    50                  55                  60

Tyr Leu Ala Ala Glu Val Leu Glu Leu Ala Gly Asn Ala Ala Arg Asp
65                  70                  75                  80

Asn Lys Lys Thr Arg Ile Val Pro Arg His Ile Gln Leu Ala Val Arg
                85                  90                  95

Asn Asp Glu Glu Leu Ser Lys Leu Leu Gly Ser Val Thr Ile Ala Asn
            100                 105                 110

Gly Gly Val Leu Pro Asn Ile His Gln Thr Leu Leu Pro Ser Lys Val
        115                 120                 125

Gly Lys Asn Lys Gly Asp Ile Gly Ser Ala Ser Gln Glu Phe
    130                 135                 140

<210> SEQ ID NO 20
<211> LENGTH: 150
<212> TYPE: PRT
<213> ORGANISM: Arabidopsis thaliana

<400> SEQUENCE: 20

Met Glu Ser Thr Gly Lys Val Lys Lys Ala Phe Gly Gly Arg Lys Pro
1               5                   10                  15

Pro Gly Ala Pro Lys Thr Lys Ser Val Ser Lys Ser Met Lys Ala Gly
            20                  25                  30

Leu Gln Phe Pro Val Gly Arg Ile Thr Arg Phe Leu Lys Lys Gly Arg
        35                  40                  45

Tyr Ala Gln Arg Leu Gly Gly Gly Ala Pro Val Tyr Met Ala Ala Val
    50                  55                  60

Leu Glu Tyr Leu Ala Ala Glu Val Leu Glu Leu Ala Gly Asn Ala Ala
65                  70                  75                  80

Arg Asp Asn Lys Lys Ser Arg Ile Ile Pro Arg His Leu Leu Leu Ala
                85                  90                  95

Ile Arg Asn Asp Glu Glu Leu Gly Lys Leu Leu Ser Gly Val Thr Ile
            100                 105                 110

Ala His Gly Gly Val Leu Pro Asn Ile Asn Ser Val Leu Leu Pro Lys
        115                 120                 125

Lys Ser Ala Thr Lys Pro Ala Glu Glu Lys Ala Thr Lys Ser Pro Val
    130                 135                 140

Lys Ser Pro Lys Lys Ala
145                 150

<210> SEQ ID NO 21
<211> LENGTH: 150
<212> TYPE: PRT
<213> ORGANISM: Arabidopsis thaliana

<400> SEQUENCE: 21

Met Glu Ser Ser Gln Ala Thr Thr Lys Pro Thr Arg Gly Ala Gly Gly
1               5                   10                  15

```
Arg Lys Gly Gly Asp Arg Lys Ser Val Ser Lys Val Lys Ala
             20                  25                  30

Gly Leu Gln Phe Pro Val Gly Arg Ile Ala Arg Tyr Leu Lys Lys Gly
         35                  40                  45

Arg Tyr Ala Leu Arg Tyr Gly Ser Gly Ala Pro Val Tyr Leu Ala Ala
     50                  55                  60

Val Leu Glu Tyr Leu Ala Ala Glu Val Leu Glu Leu Ala Gly Asn Ala
 65                  70                  75                  80

Ala Arg Asp Asn Lys Lys Asn Arg Ile Asn Pro Arg His Leu Cys Leu
                 85                  90                  95

Ala Ile Arg Asn Asp Glu Glu Leu Gly Arg Leu Leu His Gly Val Thr
             100                 105                 110

Ile Ala Ser Gly Gly Val Leu Pro Asn Ile Asn Pro Val Leu Leu Pro
         115                 120                 125

Lys Lys Ser Thr Ala Ser Ser Ser Gln Ala Glu Lys Ala Ser Ala Thr
    130                 135                 140

Lys Ser Pro Lys Lys Ala
145                 150

<210> SEQ ID NO 22
<211> LENGTH: 136
<212> TYPE: PRT
<213> ORGANISM: Arabidopsis thaliana

<400> SEQUENCE: 22

Met Ala Gly Lys Gly Lys Gly Leu Leu Ala Ala Lys Thr Thr Ala
  1               5                  10                  15

Ala Ala Ala Asn Lys Asp Ser Val Lys Lys Ser Ile Ser Arg Ser
                 20                  25                  30

Ser Arg Ala Gly Ile Gln Phe Pro Val Gly Arg Ile His Arg Gln Leu
         35                  40                  45

Lys Gln Arg Val Ser Ala His Gly Arg Val Gly Ala Thr Ala Ala Val
     50                  55                  60

Tyr Thr Ala Ser Ile Leu Glu Tyr Leu Thr Ala Glu Val Leu Glu Leu
 65                  70                  75                  80

Ala Gly Asn Ala Ser Lys Asp Leu Lys Val Lys Arg Ile Thr Pro Arg
                 85                  90                  95

His Leu Gln Leu Ala Ile Arg Gly Asp Glu Glu Leu Asp Thr Leu Ile
             100                 105                 110

Lys Gly Thr Ile Ala Gly Gly Val Ile Pro His Ile His Lys Ser
         115                 120                 125

Leu Val Asn Lys Val Thr Lys Asp
    130                 135

<210> SEQ ID NO 23
<211> LENGTH: 134
<212> TYPE: PRT
<213> ORGANISM: Arabidopsis thaliana

<400> SEQUENCE: 23

Met Ser Gly Lys Gly Ala Lys Gly Leu Ile Met Gly Lys Pro Ser Gly
  1               5                  10                  15

Ser Asp Lys Asp Lys Asp Lys Lys Pro Ile Thr Arg Ser Ser Arg
                 20                  25                  30

Ala Gly Leu Gln Phe Pro Val Gly Arg Val His Arg Leu Leu Lys Thr
         35                  40                  45
```

-continued

```
Arg Ser Thr Ala His Gly Arg Val Gly Ala Thr Ala Ala Val Tyr Thr
 50                  55                  60

Ala Ala Ile Leu Glu Tyr Leu Thr Ala Glu Val Leu Glu Leu Ala Gly
 65                  70                  75                  80

Asn Ala Ser Lys Asp Leu Lys Val Lys Arg Ile Ser Pro Arg His Leu
                 85                  90                  95

Gln Leu Ala Ile Arg Gly Asp Glu Glu Leu Asp Thr Leu Ile Lys Gly
                100                 105                 110

Thr Ile Ala Gly Gly Val Ile Pro His Ile His Lys Ser Leu Ile
                115                 120                 125

Asn Lys Ser Ala Lys Glu
            130
```

<210> SEQ ID NO 24
<211> LENGTH: 132
<212> TYPE: PRT
<213> ORGANISM: Arabidopsis thaliana

<400> SEQUENCE: 24

```
Met Ala Gly Arg Gly Lys Thr Leu Gly Ser Gly Ser Ala Lys Lys Ala
 1               5                  10                  15

Thr Thr Arg Ser Ser Lys Ala Gly Leu Gln Phe Pro Val Gly Arg Ile
                 20                  25                  30

Ala Arg Phe Leu Lys Lys Gly Lys Tyr Ala Glu Arg Val Gly Ala Gly
             35                  40                  45

Ala Pro Val Tyr Leu Ala Ala Val Leu Glu Tyr Leu Ala Ala Glu Val
         50                  55                  60

Leu Glu Leu Ala Gly Asn Ala Ala Arg Asp Asn Lys Lys Thr Arg Ile
 65                  70                  75                  80

Val Pro Arg His Ile Gln Leu Ala Val Arg Asn Asp Glu Glu Leu Ser
                 85                  90                  95

Lys Leu Leu Gly Asp Val Thr Ile Ala Asn Gly Gly Val Met Pro Asn
                100                 105                 110

Ile His Asn Leu Leu Leu Pro Lys Lys Thr Gly Ala Ser Lys Pro Ser
             115                 120                 125

Ala Glu Asp Asp
        130
```

<210> SEQ ID NO 25
<211> LENGTH: 136
<212> TYPE: PRT
<213> ORGANISM: Arabidopsis thaliana

<400> SEQUENCE: 25

```
Met Ala Gly Lys Gly Lys Gly Leu Val Ala Ala Lys Thr Met Ala
 1               5                  10                  15

Ala Asn Lys Asp Lys Asp Lys Asp Lys Lys Pro Ile Ser Arg Ser
                 20                  25                  30

Ala Arg Ala Gly Ile Gln Phe Pro Val Gly Arg Ile His Arg Gln Leu
             35                  40                  45

Lys Thr Arg Val Ser Ala His Gly Arg Val Gly Ala Thr Ala Ala Val
         50                  55                  60

Tyr Thr Ala Ser Ile Leu Glu Tyr Leu Thr Ala Glu Val Leu Glu Leu
 65                  70                  75                  80

Ala Gly Asn Ala Ser Lys Asp Leu Lys Val Lys Arg Ile Thr Pro Arg
                 85                  90                  95
```

```
His Leu Gln Leu Ala Ile Arg Gly Asp Glu Glu Leu Asp Thr Leu Ile
            100                 105                 110
Lys Gly Thr Ile Ala Gly Gly Val Ile Pro His Ile His Lys Ser
        115                 120                 125
Leu Ile Asn Lys Thr Thr Lys Glu
    130                 135

<210> SEQ ID NO 26
<211> LENGTH: 153
<212> TYPE: PRT
<213> ORGANISM: Arabidopsis thaliana

<400> SEQUENCE: 26

Met Asp Ser Gly Thr Lys Val Lys Lys Gly Ala Gly Arg Arg Ser
 1               5                  10                  15
Gly Gly Gly Pro Lys Lys Pro Val Ser Arg Ser Val Lys Ser Gly
                20                  25                  30
Leu Gln Phe Pro Val Gly Arg Ile Gly Arg Tyr Leu Lys Lys Gly Arg
            35                  40                  45
Tyr Ser Lys Arg Val Gly Thr Gly Ala Pro Val Tyr Leu Ala Ala Val
 50                  55                  60
Leu Glu Tyr Leu Ala Ala Glu Val Leu Glu Leu Ala Gly Asn Ala Ala
 65                  70                  75                  80
Arg Asp Asn Lys Lys Asn Arg Ile Ile Pro Arg His Val Leu Leu Ala
                85                  90                  95
Val Arg Asn Asp Glu Glu Leu Gly Thr Leu Leu Lys Gly Val Thr Ile
            100                 105                 110
Ala His Gly Gly Val Leu Pro Asn Ile Asn Pro Ile Leu Leu Pro Lys
        115                 120                 125
Lys Ser Glu Lys Ala Ala Ser Thr Thr Lys Thr Pro Lys Ser Pro Ser
130                 135                 140
Lys Ala Thr Lys Ser Pro Lys Lys Ser
145                 150

<210> SEQ ID NO 27
<211> LENGTH: 132
<212> TYPE: PRT
<213> ORGANISM: Arabidopsis thaliana

<400> SEQUENCE: 27

Met Ala Gly Arg Gly Lys Thr Leu Gly Ser Gly Val Ala Lys Lys Ser
 1               5                  10                  15
Thr Ser Arg Ser Ser Lys Ala Gly Leu Gln Phe Pro Val Gly Arg Ile
                20                  25                  30
Ala Arg Phe Leu Lys Asn Gly Lys Tyr Ala Thr Arg Val Gly Ala Gly
            35                  40                  45
Ala Pro Val Tyr Leu Ala Ala Val Leu Glu Tyr Leu Ala Ala Glu Val
     50                  55                  60
Leu Glu Leu Ala Gly Asn Ala Ala Arg Asp Asn Lys Lys Thr Arg Ile
 65                  70                  75                  80
Val Pro Arg His Ile Gln Leu Ala Val Arg Asn Asp Glu Glu Leu Ser
                85                  90                  95
Lys Leu Leu Gly Asp Val Thr Ile Ala Asn Gly Gly Val Met Pro Asn
            100                 105                 110
Ile His Ser Leu Leu Leu Pro Lys Lys Ala Gly Ala Ser Lys Pro Ser
        115                 120                 125
```

Ala Asp Glu Asp
    130

<210> SEQ ID NO 28
<211> LENGTH: 1677
<212> TYPE: DNA
<213> ORGANISM: Arabidopsis thaliana

<400> SEQUENCE: 28

| | | | | | |
|---|---|---|---|---|---|
| ctcacttttaa | cattttttata | tagtgacatt | tttagtaatc | caacgttatt | tatatgatta | 60 |
| gtaattcatc | aaatttatat | agtgataaaa | ttccacaatg | gttgttcaat | aaaaatatga | 120 |
| acaacacaat | agaattagta | aaagtgacta | tgttaaatca | ttttcttcgc | tggggtttgg | 180 |
| tgggcgagtt | ctaaacccat | aagcggccca | tttacttcgt | aaactcaatt | cgatttgttc | 240 |
| agcgttccaa | gcccataata | ttattttcaa | gggcataaaa | taaattgagg | tttatatgga | 300 |
| aaatttggaa | attccctcgt | ccagaagaaa | ccaacaaaaa | ctgcaaaagt | tcaagcggtg | 360 |
| ggagaaaaaa | cttcagatcg | tagccattca | ttaaattata | atcaacggtt | taaacctctt | 420 |
| cgatccgcgt | actctattct | tattggtcaa | ataacttaat | cctccaacat | atataaacaa | 480 |
| caatcagatt | tctctctgtt | aatttcgtca | agaaaaaaat | tcgatttttt | tgcgctcttt | 540 |
| gtgggttgtt | gttgttgaaa | atggctggtc | gtggaaaaac | tcttggatcc | ggtggggcga | 600 |
| agaaagctac | atctcggagt | agcaaagccg | gtcttcaatt | cccggtgggt | cgtatcgctc | 660 |
| gtttcttaaa | agccggtaaa | tacgccgaac | gtgttggtgc | cggtgctccg | gtttatctcg | 720 |
| ccgccgttct | cgaatatttg | gccgccgagg | taaaattaca | tcgtcttttc | tctctttccc | 780 |
| attccgtttc | cgatcttatt | cgtctgactc | tgttttttgcg | tgatcgatta | cgaatctagg | 840 |
| gttcttacat | tttccgaatt | tgacatgcaa | aaattgaatt | agattcgtgt | ttgaattgaa | 900 |
| ttgttgtagt | tctgtaattg | acctaatttt | gggtttgttc | tgattggttg | atggtaatcg | 960 |
| agatcatatg | aatcgttgta | gttttctcgc | aagattctaa | attttttttca | attatggtaa | 1020 |
| ccaatttgat | ttgagttgtt | aaagttctca | aatttggaaa | gtttgatcat | gaattgtgtg | 1080 |
| ttttgaattt | gttcaggttc | ttgaattagc | tggaaacgca | gcaagagaca | caagaagac | 1140 |
| acgtattgtt | cctcgtcaca | ttcagcttgc | ggtcagaaac | gatgaggagc | taagcaagct | 1200 |
| tcttggagat | gtgacgattg | ctaatggagg | agtgatgcct | aacatccaca | atctccttct | 1260 |
| ccctaagaag | gctggtgctt | caaagcctca | ggaagattag | gtcttttaac | acaatgatat | 1320 |
| agaacacgtc | tctcttttgg | ctttagatct | aataacctaa | taactagcta | gatgttttca | 1380 |
| cttttttgtat | ctttgctttt | tttaattcct | ttagggattt | gtttctttcc | gtttctgttt | 1440 |
| cgacatgttg | tttctgtttt | tgtgaatata | tgaaagtatt | ttgcgaaata | tgaatgataa | 1500 |
| tgtctttcaa | aaatgctgat | gccttattca | acaagcaaac | actgcacttt | gtagaagtat | 1560 |
| aaagattttc | tttgttgttg | atagtaatag | tacaagaaag | aaaaaaacac | aaaggattat | 1620 |
| tattctatgg | ccaacaagat | tgaaaaaata | tgaaagaaa | gtatttctaa | gactaaa | 1677 |

<210> SEQ ID NO 29
<211> LENGTH: 1903
<212> TYPE: DNA
<213> ORGANISM: Arabidopsis thaliana

<400> SEQUENCE: 29

| | | | | | |
|---|---|---|---|---|---|
| tgtggctttt | cagccaccac | aatatgtcat | acaacttgca | actgttatta | tccaaattta | 60 |
| aacccacata | aagaatacgt | ctaaaaagca | aacaataatc | attacaacac | ttagtaagtt | 120 |

-continued

```
ataacttctc cctaacttct ttgaaatttt gataaaaagg aaaatacata tgtacaagaa      180
gtgaagaaac aatttatttg ggccgaacag tgttaaattt tgggccagat aacgttaaaa      240
taaaaaggag tatttctatt taacaagccc aatatagccc atataacaat ccattgaaat      300
catcggagaa ccaaaaaaag gacaaagcag gtgggcgcac gaatctcaaa tcacgtccct      360
taaacttgta acaatctgac ggtgtagatt atcgatccat gcagtgtcat atcattggtc      420
agaaatattt tctatctcgc cactatatta atcatcatgg cgggtttcgc tgatactcat      480
tattgttatt tttgacagag agaaatttct cagttacgct tcatcctcct ctaagagatc      540 tttttctat cttgggtagt agagagaaat ggcgggtcgg ggaaaacaac ttggatctgg       600
tgcagcgaag aagtctactt ctcgtagtag caaggctggg cttcaattcc ctgttggtcg      660
tatcgctcga ttttttgaaag ccggtaagta cgccgagcgt gttggtgccg gagctccggt    720
ctatctcgcc gccgttcttg aatacctcgc cgctgaggta atcagtctct tctatttatc     780
acctgtttaa tttactcttt ttaccgaatt aaatggttat agcttgcatc tagggttctg     840
gattttagat tttcttaccc ctttcgttaa attatgcgaa atttggaata ttttagaatg     900
cattagttcc ttagtttgtt tttttcttgg gaaaaattgt ccattttttt tgtgtagttt     960
tgagctcaat ttgtgtttct ttgtgctcat catgcttatc gaaattaggg ttaaatttgt    1020
tccttactac tttgagttat catagttggc actgattgat actgtcaatt gtgttctcaa   1080
attcgaaaaa tgttgttgtt cacttagttt tgtctttgga tatgtgaaca tgtctgcttg    1140
ggaactgaat ttggtgcgct cactttctat aggtacttga gcttgctggg aacgcagcga   1200
gagacaacaa gaagacccgt atagttccac gacacattca gcttgctgtg aggaatgatg   1260
aggagctaag caagttgctt ggagatgtga caattgctaa tggaggagtg atgcctaaca   1320
tccacaatct ccttctcccc aagaaggctg gttcatctaa gcctactgaa gaagattagg   1380
ttcattacga agatagggaa agctggaaac tggttgatat cagataatgc ttaggattgt   1440 ttttttttc atttgctttt cctctgcagc aatggaagct gtgtggttgt actagttgtt    1500
aaggttacct ttgtttcact ttatgtgaat atatgaagaa attgttctat ttcagtcttg   1560
actccacttc tttagcattg ttcactgatt catttgttgt tcctgaaagt caatttaaat    1620
tccttcgata agctacacga aactgcacac atagtcacat gtaacttgtt tttaaacttt    1680
ttgttttgtt ttgttttttgg ttgaaaactc gagaaaaaaa gaatcagtag acccataatc  1740
acagaaaagt caagccacca agcgattcga catagacagt ggagaagtga cgagattgag   1800
agaatcgagg cgagagagag agagagacag ggacgattcg gtttagagct ctcgtatgag   1860
gtatatttca atttcgtttt cggcgatatc ttgtgtcgca aat                      1903
```

<210> SEQ ID NO 30
<211> LENGTH: 1609
<212> TYPE: DNA
<213> ORGANISM: Arabidopsis thaliana

<400> SEQUENCE: 30

```
gtttgacttt ataaaaacat gcagaaatgt acaagaata tatacatata attatcttaa       60
ttaatttaat aactatcaat ctgtcatact acaccactat caatctatca tcatcaccac     120
cattatgctt gacagtcact ttttagttgg cccatgttaa agctgtttgt gttatttgtt    180
attgggctta tccttcacta ccatttgatt gaaatttatc tcatgaccca acaaattgag    240
ctaatttcgg ttcaacattg gatgttaatt ttttttcaaa ccgaaccgaa ttatagtttt    300
```

| | |
|---|---|
| ggtgcatttt ttctaaaccg aattttaaca caaatagtaa tcgtcttaaa aaattcaccg | 360 |
| acttgttaaa aagaggcgga aaaaaaaacc cgcgagaact tacaatggtg ccacgctggc | 420 |
| aatccgcgtg actcacaact aaccaatcaa atccattat ctcaacgcta tatatttcag | 480 |
| aaatcacaac ctaaacccta atcactcca ctcacaaaat cctcagccat ctctaatcac | 540 |
| attttacaat cgcctcttca aatttcccga taaacaaaaa atgagttccg gcgccggcag | 600 |
| tggaacaact aaaggtggca gaggaaagcc aaaagctaca aagtccgtct ctcgatcttc | 660 |
| taaagctggt cttcaatttc ccgttggaag aatcgctaga ttccttaaag ccggtaaata | 720 |
| cgccgaacgt gttggtgccg gtgctcccgt ttatctctcc gccgttctcg aatacctcgc | 780 |
| cgctgaggta acaaacaatc ttctgtttgg tatttagtct tttagtctct atgatgagaa | 840 |
| tcactcgtaa ttgatatatc actagattt tcgatgttta ccgaatcttt gattttgatt | 900 |
| tgatgttaag gtgtcttcta gagtctgatc tcttatatga tgttgatata atcattaggt | 960 |
| attggagcta gctggaaatg cagcaagaga taacaagaag acacgtatcg taccacggca | 1020 |
| cattcagctt gcagtgagga acgatgaaga gcttagtaaa cttcttggaa gtgtaacaat | 1080 |
| tgctaatgga ggagttttgc ccaacattca tcagactctt ctcccatcaa aggttggaaa | 1140 |
| gaacaaaggc gatatcggat ctgcttctca agagtttttaa ttttattttt tagcttgtaa | 1200 |
| catagacatg gctctctgtt ccacaatagt tttggtattt tcatgttact caaaaactgt | 1260 |
| gtttgcaaat ccagtaatga attcggtttg aagaagtgaa atagttaaat ttgatgtgtt | 1320 |
| gaaatagcgg attcaatggc ttcaatacaa gtgctaatag gtttggcttt agccatggtt | 1380 |
| tctgcaagtg agactcttgc ttctttgtga gaatgtaata atgagacagt gttggaaaca | 1440 |
| gcccatttga tatgagcctc cttttctgat tctgtgaagc cgagccaccg cagaacatcg | 1500 |
| ttcaactgca acactcaaat ctcaaaaaat acattagaag attatagtct catgactatg | 1560 |
| agtggaagga gacttgagtt tgtattacct tgacaatatc tgagtatag | 1609 |

<210> SEQ ID NO 31
<211> LENGTH: 2148
<212> TYPE: DNA
<213> ORGANISM: Arabidopsis thaliana

<400> SEQUENCE: 31

| | |
|---|---|
| ttaagactga taagtatcaa caagcgaagt tttgatttgc ttgttgaagc tagtctcgga | 60 |
| cttcaaatga cacttgatat gttcatacat gtaacatgtg aagaagaact tattttggaa | 120 |
| cccaaagaca tgaatagttt gaaaaccttt ctcatgagaa tatgcaatgt taagatcttt | 180 |
| tacttgtctt atgacactct ataggtcagt cccatctttt ttgttaaagt ttacaattga | 240 |
| caattagtta gtgatgatat agttaacttg gttttttgttt cacgaactta atgactgaag | 300 |
| ttaaacaata caggtattca acaacctgat tcagttaact attttgccat gtatagagag | 360 |
| ggaatcactg ccaaatctac tcaagaattt tccaaatcta gaaaccttct tctatgaagt | 420 |
| aacatacaca ttcttgatat taacaactga catgatttta cacagtaata aattttgaaa | 480 |
| cggtctcatt ttatgtttca tggtgtgcaa cacgaatata ctaaaagatg tgtcgacgaa | 540 |
| gataagtgct tttgaaaatg ttcggatgat tatggtggag ggagagatgg tatgatagga | 600 |
| gaagtctttt gctcatagaa gtagagtgct aacagttcac aatgacttta caatctatgt | 660 |
| ggctccttga aacaataaac tatggatgtg cataactaat ggacaatctt catatttagg | 720 |
| aatgactaaa atatccttaac taatgcttaa acactcatgt gtcaccaaat aacaatacat | 780 |
| ggaacatgag tgtcaataat gaccttgtat tgtaatgggt cgctggttta gttgaagttc | 840 |

-continued

| | | | |
|---|---|---|---|
| cagtagcaca taccgaaact acattccttt tttatggagt aattctgttt taggatattt | 900 |
| ttagggtttt tggattttgt ataagacaaa aaaaaacaca aacacaataa gctacttaac | 960 |
| tagaaaataa catcatcata taatttgact aaataaacaa atcacttctt cgtggttttg | 1020 |
| ttgatgagag acatgtggat gtgagagact actccttatc caccaattgt tactttgata | 1080 |
| aatggatcaa gatccctatc tcctgcgatc accaactata aatgcattag agtaatcctc | 1140 |
| tttattttct tatcattgat tgtgttttc ggtaactcaa taacctatga agttaggcac | 1200 |
| tctaggattag aagccatgta gtcaacaaca atagcaccaa gtcgaccatg ttgtagatac | 1260 |
| tctagtcttg agttgcatgt gaatacgacc cactagaaat tgaaataaac aaagaaattt | 1320 |
| cattttttgt agtataattt gataaaattt tatactgata ttgtttcttt gtttctttca | 1380 |
| gtttcaagtg gctcgtattc acaagcaact taagaacaga gtttctgcac atagtagtgt | 1440 |
| tggtgcgact gatgttgtct acatgacttc aatccttgaa tacctaacta cagaggttct | 1500 |
| tcagttggcc gaaaacacta gcaaagattt aaaagtgaag aggataactc caaggcattt | 1560 |
| gcagttggcg atcagaggag atgaagagct tgacacactc atcaaaggaa caattattgg | 1620 |
| aggaagtgtg atccctcaca tccactagtc tcatcaacaa aacaaccaag gagtgatttg | 1680 |
| tttcttaagt taactaatat gatgtgatat gctagttaag tagcttatgg tgtttcagtt | 1740 |
| actctagttt tggatcggag aagtagttta agtgttaagt cttgagacat cataattta | 1800 |
| cgtctcatct cgtaaacgat aggagaagtt ctttgctcct agagttttgg tgctaaacaa | 1860 |
| ttcacagtga tatgcattcc atgtggctcc ttaaaaacact caaccatgca tgcacaagca | 1920 |
| gtggaccatc ttcatattca tgactgacta aaatattgtc atcaatgctt actaatatgt | 1980 |
| caaattgtag taactcggtg gtttaattga agtttcattg ttatatatat ggcgtatagg | 2040 |
| cctaaagttg tatgaagttt tgattgatga gttaagacat cgtattatat aaagtaggat | 2100 |
| tttcaagtta ctaactcaac tgattaagac acaagtcaag tactttga | 2148 |

<210> SEQ ID NO 32
<211> LENGTH: 1621
<212> TYPE: DNA
<213> ORGANISM: Arabidopsis thaliana

<400> SEQUENCE: 32

| | |
|---|---|
| agtaaaagga gatgtacgaa ccatagatca cataataatt gaaagggtag atgatctgcc | 60 |
| acgttggcaa tccgtgtgat ctaaagtcta acaaatcaca atcaatctta gtagcctata | 120 |
| tattgattta ttcttgttgc ttgatcaata aaggttacat catagaacta aaatcatatg | 180 |
| aaaccgaatc gatcaaccct ggccatcttt taaataacca tcaatacatt gggatgatca | 240 |
| atccacaata aatgtattga tgtaaattaa aaatatgaac ttgtaacaga tcaagattca | 300 |
| gggtctaaaa ttatagaaag cttaataatg gaggactatt tcactaaaat cacttttcgt | 360 |
| ttgtacatta ttttcaaaaa gtaaaaggag atgtacgaac catagatcac ataataattg | 420 |
| aaagggtaga tgatctgcca cgttggcaat ccgtgtgatc taaagtctaa caaatcacaa | 480 |
| tcaatcttag tagcctatac atatagagaa gagcaaaacc ctaaagccca ctcatcttct | 540 |
| caattcccag atcatctaca atagtcattt ctcttcgatt tcttcaaact ctcatcaaat | 600 |
| cgtttatctg ttctaaattt cgaagaagac gatgagtaca ggcgcaggaa gcggaacaac | 660 |
| caaaggtggc agaggaaagc caaaggccac caaatccgtc tctcgatcat ctaaagccgg | 720 |
| tcttcaattc cccgtcggaa gaatcgctag attcctcaaa tccggtaaat acgccgagcg | 780 |

```
tgtcggtgcc ggagctccgg tctatctctc cgctgttctc gagtacctcg ccgccgaggt    840
aatttatttt tcttgtcttc caatttggtt ttcaatttcg atttggtcac atctgaattg    900
gatcttgtac tgatttgatt ttgatttggt ttgggttgat aggtgttgga gctggcggga    960
aacgcagcaa gggataacaa gaagacacgt atagtaccaa gacacattca gcttgcagtg   1020
aggaacgatg aagagttaag caaacttctg ggaagtgtga cgattgcgaa tggaggagtt   1080
ttgccaaata ttcatcagac tcttttgcca tccaaggttg gcaagaacaa aggagatatt   1140
ggatctgctt ctcaggagtt ctgaggttct tagacttctt agttcagttc tcttgtttgg   1200
attcggaact tgtaaaatag accctgatgg tgttttttgg ggatcaaatt aggttttaaa   1260
gctaagtata tttggctttt gcctaagtat gtttaattag tgaatgatat gatatttcgg   1320
aacgaatcat gtatcaatgg aactgaatta atcgatatat caacccagaa acattttgaa   1380
acacaaacta tgcatacttg attctttatt gcagatacat gcaactcatg gagcctaata   1440
ctaaacattg ctttgatcat gtttcaattt aaccagactc attttttaat tcacccaggg   1500
agtaaaactc attaggtttt gggcctaact gcctcagtca tggtaatcct gaattaactt   1560
cactaagtta ccctcatctg ttggttcgca cctgaattag ctcgctaaat taccttcatc   1620
t                                                                   1621

<210> SEQ ID NO 33
<211> LENGTH: 1487
<212> TYPE: DNA
<213> ORGANISM: Arabidopsis thaliana

<400> SEQUENCE: 33
gtctataaac tattaaactc tagggtttaa tatgtacaaa ttctcttagg ctacttttga     60
ttaggactcc cttgtgaatg tcaaaacata atgcgacccc aaaatatctt tataagtata    120
attgttaatc ttttgattct aaaatattgt tcattgtttt ccaattaggg cttcaaagac    180
tcttgagaag catcattaaa catttaaatg tcaatgacta actttacatt taacatataa    240
ttaatctacc gaaaattagt gtaagttgca agaaattatc caaaacccca aaataaaagca   300 agcgctaaac ttttaaaatg ctacaaaaaa actggcgccg tttcaaaaag catacctctt    360
tttgattggt taatacatag tcacgcggat cgtgctttat ttgaacatcc accgtcgata    420
gactaaatcc aacggataat aatcctctcc cttctttttt tttcatttac ctataaatat    480
cacagagtac ccttcaactt taaatcacaa atcttcaact tccgatactt tcaatctctc    540
taaactctca atttcagtaa tcgataaccg tagcaatgga atccaccgga aaagtgaaga    600
aagctttcgg aggaagaaaa ccacctggtg ccccaaaaac caaatcggtt tcgaaatcga    660
tgaaagccgg tcttcaattc ccagtgggaa gaatcactcg tttcctgaag aaaggacgat    720
acgctcagag acttggtggt ggtgctccgg tttacatggc cgccgttctt gaatacctcg    780
ccgcagaagt aagtgtttcc cgatctggat tttctagtaa gattttttt ttacatttca    840 aaatcaattt tctgattcga atttattgat ctcaggttct ggagcttgct ggtaacgctg    900
cgagagataa caagaaatca aggataattc cgaggcatct tcttctcgcg ataaggaacg    960
atgaagaatt ggggaaactt ctgagtggtg tcacaatcgc tcacggtggt gttttgccta   1020
acatcaactc tgttctattg cctaagaagt ctgccactaa accagctgaa gaaaaggcta   1080
ccaaatcacc agtcaagtct ccaaagaaag cttaatctgc tagagttttc gttgctagtt   1140
tgtgtttgag ctctggtgaa tgtagaaatt tgaagctttt ggatcttagt ttctatgtat   1200
ttggtgattt agaatgttgt tcaaaatcct tttcctaatc ataagaattt atgatctatc   1260
```

```
tattatacgc ttcgtctaat cttttggtcc actcgtcgta atgtcattag tgaatattta      1320
ataaacaact tgtcatcga cattaacgaa ccctttatt cgctgtgcta aattttcctt        1380
ttaggtgaag ccaaatctaa catgttctct ctctctttg ttcgttgtaa ttccataaca       1440
tctccattac gatgttttgc gattcgagga tcttgttcta aattatt                    1487

<210> SEQ ID NO 34
<211> LENGTH: 1740
<212> TYPE: DNA
<213> ORGANISM: Arabidopsis thaliana

<400> SEQUENCE: 34
cgtggtatat acatacacgt cgttctttcc tcattttaag tcttcatttg tcatggagct      60
tagaagatta cagttgaata tcttaaactc tctttcttaa tcacattttt tgtacttatt     120
acactaatta aaaccagagt ttgggtaata atttttgttt ccttaatttt ccgaattatc     180
cgctaatttt ctactctaat tctctggata ttttaaataa tagtaataat ctgctgtcaa     240
aataagataa gaaaaagaca taaagctgat tatcttgtag aacgtgtggg gaatgaatct     300
aacggctgat atcactcaag tgttcttttc caccttcctt ttacaacacc cacgtgtaat     360
gtcatacaaa gaagtcatta cgaccgttag atcaaagcca acaagatcca atcttaacgg     420
ctaagataaa ttactacacg gatcgccaac gtggcaatac gtggtatata catacacgtc     480
gttctttcct cattttaagc aaatcgtaaa ccgccacaaa accgaaaaaa acactaattg     540 tgcttttccct ttagattcat ttgtattttc ttttggagct tttgaacaat ggagtcatca     600
caagcaacga cgaagccaac gagaggagca ggaggaagga aggtggaga taggaagaag      660 agtgttagta aatctgttaa agctggtctt caatttcccg ttggtcgtat cgctcgttac     720
ttgaagaaag gtcggtacgc tctccgatac ggttccggtg ctccggttta cctcgccgcc     780
gttctcgaat acctagccgc cgaggtatat tcaatctcag atctcgttgc attttgaatc     840
gatttatttt gtgtatctat tagatctgtt taattttgaa gttctaatga attgaaccgg     900
tttggtttag gtacttgagc tagctgggaa cgcagcgaga gataataaga gaacaggat     960 aaaccctagg catctatgtt tagcgataag gaacgatgag gaattgggga gattgcttca     1020
tggagttact attgctagtg gtggtgttct tccaaacatt aatccagttc ttcttcctaa     1080
gaaatcaaca gcttcttctt ctcaagcgga gaaagcttct gctaccaaat ctcctaagaa     1140
ggcttgataa agaatagtat cgatgttgct ttttggttat attcggatct tagatgaaga     1200
agaagaagaa gaagaaacaa cttgttttt gttttagagg atttgtgtag gtatctgaaa      1260
tcttcttctc tttgttttgg tttgtcttat gtaaaaacca tgggaagatg attatgtttg     1320
ttaacgcaat ttgtaatgga aaataattaa gttctgggat tagtaacttc atctgtctaa     1380
ttaatttctg ggtttcgtac ttgttgattt aaacaattta ggtggattaa ttgaaatggt     1440
tttggtatac acatggaaag attcagtaca gttaatgaca ttaattaaag tagataataa     1500
tcacgaaaaa catgacatta attaagaaaa tgattgttca aattgggctt tgtttgggct     1560
tagttgatag gcccgttaga atttatgttc ttggttcatc tacgagattc tggaaaaggg     1620
gttttggttt tccggtgggg tttagaattt aaacaagacg cgatttcgaa tttcgttctt     1680
gtagaatcaa attgtttggt ttcaatcctt gatttgcgat gatgaatttt ctggttcgat     1740

<210> SEQ ID NO 35
<211> LENGTH: 2151
<212> TYPE: DNA
```

<210> SEQ ID NO 35
<211> LENGTH: 2151
<212> TYPE: DNA
<213> ORGANISM: Arabidopsis thaliana

<400> SEQUENCE: 35

```
cacacttaaa tctttctttg tttaataaaa agtataatca aaaatttgaa agagagaata        60
cgtttcatta ttttttttaa ataccatcat gagaggtggt atgaatatcc actatatttt       120
aactacaaat cttcttttga ataatttgca attttatgtg atataaattt ttagtaaaat       180
aattattttc caacaacaca agatttgaac gaattttgta aagatatcta aatataaatt       240
taacatgttg acccaaaaaa tgaagaatta taacaattta gaaaagccgg cccaacaaga       300
tccacaagag ctaaacaaaa tccggcccaa caataagtcc aaactttaaa agctctcccg       360
cacaattttc gagcatcccg ctctcgtttt caggtacttc cctctctgag ctagggtttt       420
aattcgacgt ctctcttttg tctctgtatc gattttctcg ccgcgaattt cgaataggtt       480
cttcaccata agcttgagat cttatttctc tactgttctt tgcttcttct ctatcggtta       540
attatcttct ttgatttcga cgacggatct ggaaattctg aaattttgtg aagctctttt       600
cttttgttt ggtttctgta gatatggctg gtaaaggtgg gaaagggctt ctagctgcga       660
agacgacggc agcagctgca aacaaagaca gtgttaagaa gaaatccatc tctcgctctt       720
ctcgtgctgg tattcaggta tccctcaaac cctagctcct tttttgagaa tcgagtggct       780
cggagtttga atgtgcgtta ggttttttg attatgttca attgtgaatt gggaaccaga       840
tttgtatttc gttctgtgtt taatgcattt ttgggaaatt gcttcctctc tgatttctgg       900
aaatatgttt tactctgtgt ttcttcatta aagttacaat gtgtgcttga tactggactt       960
ttattgtctc tatgactcta tgccaagtag cattattttt ggtgtgtctc attttatgac      1020
tgtgatatgg tagcttgcat gttctatacg gttgatacac acaagcttga tttctctgtg      1080
tgcacttctt gtagttgcgt atgaagaaaa acagtgctat ctatctagat tctagagtaa      1140
tttgtataca atagagtact accaattgat actgagcctt aatgggagca tctacttgtc      1200
ctctctgtgt gtgtgttctg gaaatctaag ccaaacattg tcctgttatt gtcattagtt      1260
tacttttggg attcttcctt gttaaagccg aattgtacat atcattgaat ccatgttact      1320
tatatggctt attgctgcag tgtctttttat tatgataatc acttgatacg ttgtaatatc      1380
tatctataag atgtagtaag tgaatgatca agcaaattaa aggactgtgt ggttagttta      1440
agtgtcttat taatatatat ctatctacaa gaagatctgt ctcagtctga ttaatgggaa      1500
gcctttctct gtgccctaaa gttatgtgct tattttgttt tctcaatgtg gtattctttc      1560
agtttccagt gggtcgtatt catcgtcaac tcaagcaaag agtttcagca catggaagag      1620
ttggtgccac tgctgctgtt tacactgcat caattctaga atacttgact gctgaagtac      1680
tcgagttagc tggaaatgcg agcaaggatc tcaaagtgaa gagaattaca ccaagacatt      1740
tgcagcttgc aatcagagga gatgaggaac ttgacactct catcaaagga accattgcag      1800
gaggaggtgt gatccctcac atccacaagt cccttgtcaa caaagtcacc aaggattgag      1860
tttcgctctc tgagtcctaa gtctctatta tactatgtgc tcttttctag acgccctcat      1920
gtgtatatgg gttcattgta tctcttaggt ctctcgtttt agactcatac tcttgttatt      1980
ttgctaatgc ttacatgatt gaggatgatg gttcttgctt tcttggtttc ctatactgtt      2040
gcatgccct cttctagcta accccggaca atagaaatcc tcgattagat gatgaaaacc      2100
attcaacatc tatgtagcaa ctgatgacaa cagcgtttga ttgtttcaca a              2151
```

<210> SEQ ID NO 36
<211> LENGTH: 1883

```
<212> TYPE: DNA
<213> ORGANISM: Arabidopsis thaliana

<400> SEQUENCE: 36
ttagggacga atttgtgatt tatgattatt tgactttaga ttgggcttgg gcttttttcg      60
caggttgggg tataagggta aaatcgtcat ttgacagacc gacttgtctc tctctatctg     120
gggaaaacgt cttttcacat caacaaagaa ggaaaaaccg cagagaaacc atctgatact     180
taagctaaac tgagcgtaca aaaagcctct atatgtctta gttcatgatt tgctatgttt     240
tgtttccaga ctgaatgatt atacagagaa aacaaacaaa gatctccctc tcttcttttg     300
aatcaaaaca tgggtgttaa aatttaatag ttttctttca agtgtctttt tcaatattga     360
actaaattta gggacgaatt tgtgatttat gattatttga ctttagattg ggcttgggct     420
tttttcgcag gttgggtat aagggtaaaa tcgtcatttg acagaccgac ttgtctctct     480
ctatctgggg aaaacgtcta tcgggagact cctcttcgag ctcatcttct tctctctctt     540
tttatctttg gttgtgcgat ctcctttctc tttcaatctc caaggatttt actgtgagat     600
atttggcggg aaaatgtcgg ggaaaggtgc taaaggtttg attatgggga aacccagcgg     660
tagcgacaag gataaggaca agaagaagcc tatcactcgt tcttctcgag ctggtctcca     720
ggtagattat aatctccctc acactctaag tcttccgtgt ctgtttcttt gggaatcgaa     780
atggtcttat acacctgaac gattagtaga tcgcgtttaa gtggtagatc gatgagattc     840
tgagctagat ttggtaattt cagctgagaa ttagagacat tgggatgcga gatttggttt     900
tctattgtgt tatctgctgg agaattgttt cattaagctt ttatggttga tattgaaccc     960
gatctttgat ttcacggagt cttgttgtta cagctaccct tgtgaattgaa ttcggagttt    1020
tttttgtaga gatttattgt catatatgaa atgtttctgg gagcaattga gatttgagta    1080
ttcatttagg ttccattgtt gtggctaatt gaatttacat tgtgtgcagt tcccagttgg    1140
tagggtgcat cgtctgttaa agacaaggtc cactgctcat ggaagggttg gagcaactgc    1200
agctgtttac acagcagcaa tattggagta tctgactgca gaagttttgg agttggctgg    1260
taacgccagc aaggacttga aggtgaaacg tatctcgccg aggcatttgc agcttgcgat    1320
tcgtggagat gaggagctcg atactctcat caaaggaact atagctggtg gtggagtcat    1380
ccctcatatc cacaagagtc tcatcaacaa atccgccaag gaataggact ttttagtta    1440
cccgctttgt tctgtgttgc ttttctgttt tctaaatgtt tttaagagtt gttgtttgat    1500
aagatgctag agaagctctt tttaggatcg tttgctattg ttcgttcgat cagcgtactt    1560
tgtgttagag acgccagtcg atttatctat ctttaaaaat gtattcgaat gattatccaa    1620
aaaccatttc tgactaccta ccttgctggt tgttcgctg gagaagcttg aaagcaaatt     1680
cattgggaag gatttgtatt atctctaaat agaattcata tatacatcat acataagtaa    1740
aaatcacagg tttgtgttta agaaaattag gctgataata ttcacttggc ctagttgacg    1800
tcgatgtgat tctgaagcaa agttctttgt agcaaatctg gtgggagttt taatcccttt    1860
aagaatacac tgatgcctga ttt                                            1883

<210> SEQ ID NO 37
<211> LENGTH: 1438
<212> TYPE: DNA
<213> ORGANISM: Arabidopsis thaliana

<400> SEQUENCE: 37
attcgaatta tgaaaatcaa aaaggaatga agcgggaaca aaaccttggg gatttagttt      60
```

```
gaatcgtgat gaagaaggaa gatcagagct tgagggagat tcgaaatttc ctcgcttcat      120
aacaaaatct gagaaataga tttgaaaaac agacaacact aggttacaaa aactgttact      180
cgatgaataa aaaagagga cttttcaaa tcttcacaca caaatttcac aaagaacccg      240
gattcaattt ttgaaaattg ggctctttgg taaaatgtaa aacgtttggg ccgaaaaaag      300
aagaaaaaaa caaaactgta aagaggcaaa gaggatattt tggtaattca ctctgacgcg      360
gatcctgaat ctcgaattat tcaccgttga ttataacatt atctaacggt gataaacagc      420
gatccgcgta gtttcttctt attggttaag acgaatctaa aacagtatat aaactctgga      480
gaagatggag agagtccata acaacaaatt cgattcttat aactgtttcc ctctcatctt      540
tacacaaaag tattctaatc gatttcaatg gcgggtcgtg gtaaaacact cggatctggg      600
tctgcgaaga aggcaacaac aagaagcagc aaagccggtc tccaattccc tgtgggtcgt      660
atcgctcgtt tcttgaagaa aggcaaatac gccgaacgtg ttggtgccgg agctccggtt      720
tacttagccg ccgttctcga atacctcgcc gctgaggtaa ttcctcttcc ctattcttca      780
aattttcgat cttttagttc aatttctata accctaatt ttgactgatt tggggaaat      840 tttgaaaaat taggtattgg aattggctgg aaacgcagcg agggataaca agaagacgag      900
gattgttcca aggcatattc aattggcggt gaggaacgat gaagaattga gcaaattgct      960
tggagatgtg actattgcta atggaggtgt gatgcctaac attcacaatc ttcttcttcc     1020
taagaagacc ggtgcttcca agccatctgc tgaagacgat tgattaatca accaaatcca     1080
ctctcttgtg ttttttgagt ttttaaggct tttaagagt aatttagatt agatctatgg     1140
tgaagaaaga atctatcttc tgtgtttttt gaattgaatt gaatgttcat atgctttcaa     1200
tttcttatgg aatcaagatt ttaacttttc taggttttcg agttatgatg atgaaattct     1260
tagtcttata aatcactaaa gacttgggat ttttgattgg ttgacataaa gaatggactt     1320
ttgagttaaa tttgggaaag ctactgggaa tgacatcatg agaggtgtat aattgagcaa     1380
ctatgacata tattaaaaga gatctgaagg attgatgatg attggtgggc caataatg       1438
```

<210> SEQ ID NO 38
<211> LENGTH: 1901
<212> TYPE: DNA
<213> ORGANISM: Arabidopsis thaliana

<400> SEQUENCE: 38

```
tcttaacaat caaaccaaag catataatat tctcttacca tttagtttta ccacaagcat       60
agtgcctaca acctttctca tgaaaaatgg atctttctgt tacaaaagaa aaaaaaaagc      120
tgattttaaa cgtttctaag aaatagaggg cttaatggca aaatgttgaa acatttaag       180 gctccaaagc gaaaaattta accgccaaag cgtaggtttc ccccaagat tttgaaaata       240 tttaaaaact cccaccaaac tttttaattt taaaactcta atcccattct attcaaccag      300
atttcgtttc tttcgtcctt tttttccttt tgcattctct cgtcgtcgtc tcaaggtact      360
ttacttctct ttttctctct tccaatattc gagatctgtt tctgtctttc ttggatcgat      420
tctcgattct gttcttcgat ttagtcttct ttcgaataga tctggtagat ttaagcatta      480
tactcttctt tttctgattt cgttttgtt tgactgtgta cggttagatc tagaagaagg      540
aaacaacaat ttcagagac atggcaggca aaggtggaaa aggactcgta gctgcgaaga      600
cgatggctgc taacaaggac aaagacaagg acaagaagaa acccatctct cgctctgctc      660
gtgctggtat tcagtcatc tcttaaaccc taatttcgac gaccttgttt gactctgatt      720
ctttcctaat tcatcagtac catttacatt tttaggaata gatttgtttt tttggttcta      780
```

-continued

| | |
|---|---|
| tgtaaaagca tgaggaagta aacttgctgg atatgtgtaa tttcttttac tcggtaccat | 840 |
| gttgatgttt ttgtcaatgt ttgtgctaat tatacaaatt tgtgttgctt gctcactggt | 900 |
| tgcttggtca tctgagaata catgttgttg ttgttttgt ctccccattg tttaggtagt | 960 |
| gtcttatggt atgtgcccaa atgttccctt actctgtagc ttactattga tattgatgag | 1020 |
| tcatgagggt tttaatatgt tttgtttggt tctagtatgt gcaatgttct gttttttatt | 1080 |
| aagttatact attttaatgg aactatttgg tgtgcgctga tactgttttg acattgatgc | 1140 |
| tgtgcatagc catacaagta gagagattgg tcacaccgat actgtttttt ttttcagtt | 1200 |
| tccagttgga cgaattcaca ggcaactgaa gacccgagtc tcggcacatg cagagttgg | 1260 |
| tgccactgca gccgtctaca cagcttcaat cctggagtat ctgacagcag aggttcttga | 1320 |
| gttggctggg aatgcgagca aggatctcaa agtgaagagg ataacgccaa ggcatctgca | 1380 |
| gttggcgatt agaggagatg aggagctgga cacactcatc aagggaacga ttgctggagg | 1440 |
| tggtgtgatc cctcacatcc acaagtctct catcaacaaa accaccaagg agtgatgtgt | 1500 |
| agctttttat ggtgtttgta tttctgtagt cttggactca ttttcctta tccttttctt | 1560 |
| agttctttga ctagtgttga cctcttctgg acatcctcag gtgtacatta gttaatttga | 1620 |
| actctttagg ttccttgttc aatcatatgt tctctttcta tgctattgtg atttgcttat | 1680 |
| tatgttttca agtgaaccgt tttctgtttt aaacaactga ggaaatcatt tactcgcatg | 1740 |
| ctctctggta accggactta caagtatctt ttagatatag aacttgttat caaacatcat | 1800 |
| cagtatttta tcaagtcaca tattccaaat caggcgcaaa tagcccaatc acaagtcaaa | 1860 |
| gactcaatat taaaaaaaaa agagtacatc attcattcac t | 1901 |

<210> SEQ ID NO 39
<211> LENGTH: 1733
<212> TYPE: DNA
<213> ORGANISM: Arabidopsis thaliana

<400> SEQUENCE: 39

| | |
|---|---|
| gatttagtgt ccaatagaaa gcatccaagt ttttgccaaa aaaaagaaa gaaagcatcc | 60 |
| aagcaataca tataagtttc atttgcatta tattcaacag taccattttc atatcttgtt | 120 |
| tcaaaaaata catcaaatta ttttccaaac cttcacatat aatttgagaa gaaatattac | 180 |
| aaatttaata taggttcagc ataatttaga aaatattatt caatgtttaa aacttctcct | 240 |
| aaattttgga gtattgctat taatcctttt aatgtgaaca aaacattgaa gcgaaggttg | 300 |
| ccagatcagc aaatcatagc cgttgattca cttccaatcc aaaagctaac attcatcaac | 360 |
| tgacaaaacc aaccaaccaa ccaacttctt tcgctatctt acgccaaagc tctcttaatt | 420 |
| cctccgtttg catattttcc ggtcagatca aaatcagaat cagaatcaaa tttctcgtcg | 480 |
| tgtcggagta aatcaagcca tggattccgg aaccaaagtg aagaaggag ccgctggaag | 540 |
| aagaagtggt ggaggtccta agaagaaacc ggtttcccgt tcggttaaat ccggtctaca | 600 |
| gtttcctgtc ggtaggatcg gtcggtatct taagaaaggt cgttattcga agcgtgtcgg | 660 |
| aaccggagct ccggtctatc tcgccgccgt cctcgagtat cttgctgctg aggtaataaa | 720 |
| gttctgaatt cagatcagct aatcatttca tcggaattat cgcagtttca tcgatttcac | 780 |
| tagaattctt gtgggttttg ttctgttgct tcgttgacca tctataggtg tagaatgtct | 840 |
| tcttctgatt ttagggtaaa ttgataatca tctgaggttg taaaattgaa tttgttagat | 900 |
| actatatcac gagtagatca acctcaagac atggtttcac tttcaattag gtttaacatc | 960 |

```
tttgctttgc aaatctcaaa atcttagata gagatatatt agcgttacat aaaaactaaa      1020
gttgcatagt caataaaacc taaataaaac atctgcaagt aaacttcatt gagaatctat      1080
catcatgtaa caccgttttg agaatctgaa taccttggac tgatgtgcat gttacatgta      1140
actcttgtca acaaatctct gagtaactag gatatgcaaa tattgcatac taatcttttt      1200
gatcgaatgt gacaaaaccc cattttaaag tttacaagtc tgatccgtta tatatatgtt      1260
gtcgatttag gttctcgagc ttgctggtaa cgctgcaaga gataacaaaa agaaccgtat      1320
tataccacgc catgttctat tagcggtgag gaacgacgag gagctaggga cactactcaa      1380
aggcgtaacc attgcacacg gcggtgtttt accaaacata aacccaatac tcctcccaaa      1440
gaagtctgag aaagcagctt caactacaaa aacacccaaa tcaccatcaa aggcaaccaa      1500
atcccctaag aaatcttagt acttctttct tcattcctct gtataaccta ctgtttctat      1560
ctctctgtac gtttctctgt aaagacagaa cagaatatct ctttgttgtt gtgagaaagc      1620
ttagtttctc tgatcgtcgt tgtgaaataa aaaatgcaac gtttcatata gattttgcac      1680
aatcaaaaag tattcatata aacaatgtat tattattcga ctatcatcat atg            1733

<210> SEQ ID NO 40
<211> LENGTH: 1438
<212> TYPE: DNA
<213> ORGANISM: Arabidopsis thaliana

<400> SEQUENCE: 40
ttaatacgac atgctaaaaa ttgattaatc atgtttagaa aaatatatac tatgataaac       60
ctgaaattgt gtcacacaat tttgatgaat gtatataccc catttccata ttatacgttt      120
taaaagtaag attttcataa attttaaaat tattcataac attcactaaa attagatgtg      180
tataattaac aaactaaaaa tatcattaat ctactatttt agtagttatt ttgcgaaaat      240
atgtttgagt tacaaaatat tttcactatt taaatcatgt cgattatacc cactgaaggg      300
tatttccgtc aatcccaatt ctaacaatga attcaggagt ataaaaacgt aaattcaagc      360
gtgccaatta taaccgtcg atcataatct aatccaacgg cagtaacatc gatccgcgtg      420
attgtttatt attggataag aatcactcaa ccgtctctac acagtatata taataaccaa      480
agagcgtcct cttacgctta tcttaatttc cctcgcattg agaattttca acttttcta       540 tctctcttcc caaatcacaa atggcgggtc gcggcaaaac tctcggatct ggcgttgcta      600
agaaatcaac atcgagaagc agcaaagccg gtctccaatt ccccgttggt cgtatcgctc      660
gttttctaaa gaacggcaag tacgcaacac gtgttggtgc cggagctccg gtttacttag      720
ccgccgttct cgaatacctc gccgctgagg taattatccc cttctctccc tatatctctt      780
tactctttcg atcttcaatt tcgtaaaacc ctaatttcta aattggatct gttgtgttgt      840
aggtattgga attggctgga aacgcagcta gggataacaa gaagactagg attgtgccac      900
gtcacattca gctcgcggtg agaaacgatg aggagctgag taaactgctt ggagatgtga      960
cgattgctaa tggaggtgtg atgcctaaca ttcacagtct tcttcttccc aagaaagctg     1020
gtgcttcaaa accttccgct gatgaagatt agattaggga tttgtgttgt ggttgtttag     1080
ctaattaatg tgtagcttag tctttcatta gattagatct gaattagttt tcattaatgg     1140
tgttgtgtag tctctctttt gcttcaaaaa caagtattaa aatcttatta ttttgaattg     1200
aatccacaat caatacacat tgaagtccta acaaactact tcttcccagt gatatttgaa     1260
```

```
accaaatcac taagaaactt agctgatttg gtaataggag aattcatagc catcaagtta    1320
tacagaacaa gctcaacttc ttcgattgat ggtcgagaat tgaattgtga aacaactttc    1380
aaagtaccat taccttcttc ttcttcaacg agaacattcc atctttctcc actcacaa     1438
```

We claim:

1. A method for increasing *Agrobacterium* transformation efficiency in a host plant, said method comprising:
   a. increasing histone levels in the host plant compared to normal levels of histone in the host plant by expressing an exogenous copy of a plant histone gene; and
   b. transforming the host plant with *Agrobacterium*;
   wherein the transformation efficiency of the host plant expressing the exogenous plant histone gene is increased compared to that of a plant not comprising the exogenous plant histone gene.

2. The method of claim 1, wherein the histone is an H2A histone.

3. The method of claim 2 wherein the H2A histone is encoded by *Arabidopsis* RAT5.

4. The method of claim 1 wherein transformation frequencies are measured by the number of tumors produced in the host plant.

5. The method of claim 2, wherein the H2A histone is H2A-1.

6. A method of increasing *Agrobacterium* transformation efficiency in a host plant, the method comprising:
   (a) introducing at least one copy of a polynucleotide sequence encoding a plant histone protein to the host plant;
   (b) selecting a host plant expressing the polynucleotide sequence encoding a plant histone protein; and
   (c) transforming the host plant expressing the polynucleotide sequence encoding a plant histone protein with a DNA molecule of interest using *Agrobacterium*;
   wherein the transformation efficiency of the host plant expressing the polynucleotide sequence encoding the plant histone protein is increased compared to that of a plant not transformed with the polynucleotide encoding the plant histone protein.

7. The method of claim 6, wherein the host plant is a monocot plant.

8. The method of claim 7, wherein the monocot plant is maize.

9. The method of claim 6, wherein the polynucleotide sequence encoding a plant histone protein is a member of an H2A gene family of *Arabidopsis*.

10. The method of claim 9, wherein the member of the H2A gene family of *Arabidopsis* is RAT5.

11. The method of claim 7 further comprising adding L-cysteine at a concentration between about 100 mg/L and about 400 mg/L to media used in cultivating the host plant, wherein the host plant is monocot.

12. A method of increasing *Agrobacterium* transformation efficiency in a monocot host plant, the method comprising:
   (a) introducing a nucleic acid sequence encoding a plant histone H2A into a host plant;
   (b) selecting a host plant material expressing the plant histone H2A protein;
   (c) infecting the host plant material with a DNA molecule of interest by infection with an *Agrobacterium* strain;
   (d) providing at least one antioxidant in a cocultivation medium, wherein the antioxidant is L-cysteine at a concentration between about 100 mg/L and about 400 mg/L of cocultivation media; and
   (e) selecting the infected material for transformants expressing the DNA molecule of interest;
   wherein the transformation efficiency of the monocot host plant expressing the nucleic acid sequence encoding the plant histone H2A protein is increased compared to that of a plant not transformed with the nucleic acid encoding the plant histone H2A protein.

13. The method of claim 12, wherein the monocot plant is maize.

14. The method of claim 12, wherein the infecting of the host plant in the cocultivation medium is for about 3 days.

15. The method of claim 12 wherein the host plant material is an embryo.

* * * * *

UNITED STATES PATENT AND TRADEMARK OFFICE
CERTIFICATE OF CORRECTION

| | | |
|---|---|---|
| PATENT NO. | : 7,279,336 B2 | Page 1 of 1 |
| APPLICATION NO. | : 10/664658 | |
| DATED | : October 9, 2007 | |
| INVENTOR(S) | : Gelvin et al. | |

It is certified that error appears in the above-identified patent and that said Letters Patent is hereby corrected as shown below:

On the title page, item (73), the Assignee names should read:

--(73) Assignee: PURDUE RESEARCH FOUNDATION, West Lafayette, IN (US); and IOWA STATE UNIVERSITY RESEARCH FOUNDATION, INC., Ames, IA (US)--

Signed and Sealed this

Third Day of March, 2009

JOHN DOLL
*Acting Director of the United States Patent and Trademark Office*